US012807969B2

(12) United States Patent
Gillmeister et al.

(10) Patent No.: US 12,807,969 B2
(45) Date of Patent: Nov. 24, 2026

(54) PRODUCTION OF RECOMBINANT POLYPEPTIDES AND VIRUSES

(71) Applicant: REGENXBIO Inc., Rockville, MD (US)

(72) Inventors: Michael Gillmeister, Rockville, MD (US); Stephen Vaughn, Rockville, MD (US)

(73) Assignee: REGENXBIO Inc., Rockville, MD (US)

( * ) Notice: Subject to any disclaimer, the term of this patent is extended or adjusted under 35 U.S.C. 154(b) by 581 days.

(21) Appl. No.: 18/261,551

(22) PCT Filed: Jan. 21, 2022

(86) PCT No.: PCT/US2022/013250
§ 371 (c)(1),
(2) Date: Jul. 14, 2023

(87) PCT Pub. No.: WO2022/159662
PCT Pub. Date: Jul. 28, 2022

(65) Prior Publication Data

US 2024/0084329 A1 Mar. 14, 2024

Related U.S. Application Data

(60) Provisional application No. 63/139,992, filed on Jan. 21, 2021.

(51) Int. Cl.
*C12N 15/87* (2006.01)
*C08G 73/02* (2006.01)
(Continued)

(52) U.S. Cl.
CPC ............ *C12N 15/87* (2013.01); *C08G 73/02* (2013.01); *C12N 1/38* (2013.01); *C12P 21/00* (2013.01); *C12N 2750/14151* (2013.01)

(58) Field of Classification Search
CPC ................................ C12N 15/87; C12N 1/38; C12N 2750/14151; C08G 73/02; C12P 21/00
See application file for complete search history.

(56) References Cited

U.S. PATENT DOCUMENTS

2008/0254512 A1* 10/2008 Capon ................ A61K 47/6875 435/69.6
2015/0079659 A1 3/2015 Gorfien et al.

FOREIGN PATENT DOCUMENTS

WO WO-2020219897 A1 * 10/2020 ............ C12N 15/86

OTHER PUBLICATIONS

Park JY, et al. Scalable production of adeno-associated virus type 2 vectors via suspension transfection. Biotechnol Bioeng. Jun. 20, 2006;94(3):416-30. (Year: 2006).*
(Continued)

*Primary Examiner* — Neil P Hammell
*Assistant Examiner* — Delphinus Dou Yi Yu
(74) *Attorney, Agent, or Firm* — Nixon & Vanderhye, PC

(57) ABSTRACT

Provided herein are improved methods for producing a recombinant polypeptide or virus particle. In some embodiments, a method for producing a recombinant polypeptide or virus particle disclosed herein comprises providing a cell culture comprising cells capable of producing the recombinant polypeptide or virus particle and dextran sulfate, and transfecting the cells by adding to the culture a composition comprising one or more polynucleotides and a transfection reagent. In some embodiments, the recombinant virus particle is a recombinant AAV (rAAV) particle.

20 Claims, 12 Drawing Sheets

(51) Int. Cl.
*C12N 1/38* (2006.01)
*C12P 21/00* (2006.01)

(56) References Cited

OTHER PUBLICATIONS

NPL_Agilent_rAAV_helper_free_system (Year: 2015).*
Hyoung Park J, et al. The molecular weight and concentration of dextran sulfate affect cell growth and antibody production in CHO cell cultures. Biotechnol Prog. Sep. 2016;32(5):1113-1122. (Year: 2016).*
NPL_Merten_2014_Virus-Production-under-Suspension-Conditions (Year: 2014).*
Tiyaboonchai_2003_Formulation_and_characterization_of_DNA-PEI-dextran_sulfate_nanoparticles (Year: 2003).*
Hess_2007_Cellular_binding_motion_and_internalization_of_synthetic_gene_delivery_polymers (Year: 2007).*
Sompayrac-danna-1981-efficient-infection-of-monkey-cells-with-dna-of-simian-virus-40 (Year: 1981).*
Gutlerrez-Granados et al., Sonia Gutierrez-Granados et al: Advancements in mammalian cell transient gene expression (TGE) technology for accelerated production of biologics, Critical Reviews in Biotechnology, Jan. 2, 2018, pp. 918-940, vol. 38, No. 6.
Merten et al., Virus Production Under Suspension Conditions "In:" Industrial Scale Suspension Culture of Living Cells, Wiley-VCH Verlag Gmbh & Co. KGaA, Jun. 18, 2014, pp. 503-554.
Park J H et al., The molecular weight and concentration of dextran sulfate affect cell growth and antibody production in CHO cell cultures, Biotechnology Progress, Sep. 1, 2016, pp. 1113-1122, vol. 32, No. 5.
Park J Y et al., Scalable production of adeno-associated virus type 2 vectors via suspension transfection, Biotechnology and Bioengineering,, Jun. 20, 2006, pp. 416-430, vol. 94, No. 3.
International Search Report for PCT/US2022/013250 mailed May 11, 2022, 4 pages.
Written Opinion of the ISA for PCT/US2022/013250 mailed May 11, 2022, 8 pages.
Unknown, "Guide for DNA Transfection in iCELLis® 500 and iCELLis 500+ Bioreactors for Large Scale Gene Therapy Vector Manufacturing", Polyplus Transfection, Pall Biotech, 21 pages.
Geng et al., "Optimizing Medium for Transient Transfection", Cell Technology for Cell Products, 53-55, 3 pages, 2007.

* cited by examiner

PRODUCTION OF RECOMBINANT POLYPEPTIDES AND VIRUSES

CROSS-REFERENCE TO RELATED APPLICATIONS

This application is the U.S. national phase of International Application No. PCT/US2022/013250 filed Jan. 21, 2022 which designated the U.S. and claims priority to U.S. 63/139,992 filed Jan. 21, 2021, the entire contents of each of which are hereby incorporated by reference.

TECHNICAL FIELD

The present disclosure relates to a method comprising transfecting a host cell in a culture medium comprising dextran sulfate.

BACKGROUND

Recombinant adeno-associated virus (AAV)-based vectors are currently the most widely used gene therapy products in development. The preferred use of rAAV vector systems is due, in part, to the lack of disease associated with the wild-type virus, the ability of AAV to transduce non-dividing as well as dividing cells, and the resulting long-term robust transgene expression observed in clinical trials and that indicate great potential for delivery in gene therapy indications. Additionally, different naturally occurring and recombinant rAAV vector serotypes, specifically target different tissues, organs, and cells, and help evade any pre-existing immunity to the vector, thus expanding the therapeutic applications of AAV-based gene therapies. Before replication defective virus, for example, AAV based gene therapies can be more widely adopted for late clinical stage and commercial use, new methods for large scale production of recombinant virus particles need to be developed.

Thus, there is a need in the art to improve the productivity and yield of methods for the large scale production of rAAV particles.

BRIEF SUMMARY

In one aspect, the disclosure provides a method of transfecting cells, comprising (a) providing a cell culture comprising the cells, wherein the culture comprises between about 0.1 mg/L and about 10 mg/L dextran sulfate; and (b) transfecting the cells by adding to the culture a composition comprising one or more polynucleotides and a transfection reagent. In some embodiments, the cell culture is a suspension culture. In some embodiments, the cell culture is a suspension culture comprising suspension-adapted HEK cells. In some embodiments, the transfection reagent comprises polyethylenimine (PEI).

In a further aspect, the disclosure provides a method of producing a recombinant polypeptide, comprising (a) providing a cell culture comprising cells suitable for producing the recombinant polypeptide, wherein the culture comprises between about 0.1 mg/L and about 10 mg/L dextran sulfate; (b) transfecting the cells by adding to the culture of (a) a composition comprising one or more polynucleotides encoding the polypeptide and a transfection reagent; and (c) maintaining the cell culture comprising the transfected cells under conditions that allow the production of the recombinant polypeptide. In some embodiments, the recombinant polypeptide is an antibody or antigen-binding fragment thereof, bispecific antibody, enzyme, fusion protein or Fc fusion protein.

In a further aspect, the disclosure provides a method of producing a recombinant virus particle, comprising (a) providing a cell culture comprising cells suitable for producing the recombinant virus particle, wherein the culture comprises between about 0.1 mg/L and about 10 mg/L dextran sulfate; (b) transfecting the cells by adding to the culture of (a) a composition comprising one or more polynucleotides containing genes necessary for producing the recombinant virus particle and a transfection reagent; and (c) maintaining the cell culture comprising the transfected cells under conditions that allow the production of the recombinant virus particle. In some embodiments, the recombinant virus is recombinant adeno-associated virus (rAAV). In some embodiments, the rAAV comprises a capsid protein of the AAV1, AAV2, AAV3, AAV4, AAV5, AAV6, AAV7, AAV8, AAV9, AAV10, AAV11, AAV12, AAV13, AAV14, AAV15, AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 serotype. In some embodiments, the rAAV comprises a capsid protein of the AAV8 or AAV9 serotype. In some embodiments, the cell culture is a suspension culture comprising suspension-adapted HEK cells. In some embodiments, the transfection reagent comprises polyethylenimine (PEI).

In one aspect, the disclosure provides a method of transfecting cells, comprising (a) culturing the cells in a cell culture, wherein the culture comprises a starting dextran sulfate concentration of between about 1 mg/L and about 20 mg/L and a final dextran sulfate concentration of between about 0.1 mg/L and about 10 mg/L; and (b) transfecting the cells by adding to the culture of (a) a composition comprising one or more polynucleotides and a transfection reagent. In some embodiments, the cell culture is a suspension culture. In some embodiments, the cell culture is a suspension culture comprising suspension-adapted HEK cells. In some embodiments, the transfection reagent comprises polyethylenimine (PEI).

In a further aspect, the disclosure provides a method of producing a recombinant polypeptide, comprising (a) culturing cells suitable for producing the recombinant polypeptide in a cell culture, wherein the culture comprises a starting dextran sulfate concentration of between about 1 mg/L and about 20 mg/L and a final dextran sulfate concentration of between about 0.1 mg/L and about 10 mg/L; (b) transfecting the cells by adding to the culture of (a) a composition comprising one or more polynucleotides encoding the polypeptide and a transfection reagent; and (c) maintaining the cell culture comprising the transfected cells under conditions that allow the production of the recombinant polypeptide. In some embodiments, the recombinant polypeptide is an antibody or antigen-binding fragment thereof, bispecific antibody, enzyme, fusion protein or Fc fusion protein.

In a further aspect, the disclosure provides a method of producing a recombinant virus particle, comprising (a) culturing cells suitable for producing the recombinant virus particle in a cell culture for between about 1 day and about 5 days, wherein the culture comprises a starting dextran sulfate concentration of between about 1 mg/L and about 20 mg/L and a final dextran sulfate concentration of between about 0.1 mg/L and about 10 mg/L; (b) transfecting the cells by adding to the culture of (a) a composition comprising one or more polynucleotides containing genes necessary for producing the recombinant virus particle and a transfection reagent; and (c) maintaining the cell culture comprising the transfected cells under conditions that allow the production of the recombinant virus particle. In some embodiments, the recombinant virus is recombinant adeno-associated virus (rAAV). In some embodiments, the rAAV comprises a capsid protein of the AAV1, AAV2, AAV3, AAV4, AAV5, AAV6, AAV7, AAV8, AAV9, AAV10, AAV11, AAV12, AAV13, AAV14, AAV15, AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 serotype. In some embodiments, the rAAV comprises a capsid protein of the AAV8 or AAV9 serotype. In some embodiments, the cell culture is a suspension culture comprising suspension-adapted HEK cells. In some embodiments, the transfection reagent comprises polyethylenimine (PEI).

In a further aspect, the disclosure provides a method of improving the production of a recombinant polypeptide, comprising (a) providing a cell culture comprising cells suitable for producing the recombinant polypeptide, wherein the culture comprises between about 0.1 mg/L and about 10 mg/L dextran sulfate; (b) transfecting the cells by adding to the culture of (a) a composition comprising one or more polynucleotides encoding the polypeptide and a transfection reagent; and (c) maintaining the cell culture comprising the transfected cells under conditions that allow the production of the recombinant polypeptide. In some embodiments, a method disclosed herein produces more polypeptide than a method comprising transfecting the cells in a culture that does not comprise dextran sulfate. In some embodiments, the recombinant polypeptide is an antibody or antigen-binding fragment thereof, bispecific antibody, enzyme, fusion protein or Fc fusion protein.

In a further aspect, the disclosure provides a method of improving the production of a recombinant virus particle, comprising (a) providing a cell culture comprising cells suitable for producing the recombinant virus particle, wherein the culture comprises between about 0.1 mg/L and about 10 mg/L dextran sulfate; (b) transfecting the cells by adding to the culture of (a) a composition comprising one or more polynucleotides containing genes necessary for producing the recombinant virus particle and a transfection reagent; and (c) maintaining the cell culture comprising the transfected cells under conditions that allow the production of the recombinant virus particle. In some embodiments, a method disclosed herein produces more recombinant virus particles than a method comprising transfecting the cells in a culture that does not comprise dextran sulfate. In some embodiments, the recombinant virus is recombinant adeno-associated virus (rAAV). In some embodiments, the rAAV comprises a capsid protein of the AAV1, AAV2, AAV3, AAV4, AAV5, AAV6, AAV7, AAV8, AAV9, AAV10, AAV11, AAV12, AAV13, AAV14, AAV15, AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 serotype. In some embodiments, the rAAV comprises a capsid protein of the AAV8 or AAV9 serotype. In some embodiments, the cell culture is a suspension culture comprising suspension-adapted HEK cells. In some embodiments, the transfection reagent comprises polyethylenimine (PEI).

In some embodiments, the disclosure provides:

[1.] A method of transfecting cells, comprising:
- a) providing a cell culture comprising the cells, wherein the culture comprises between about 0.1 mg/L and about 10 mg/L dextran sulfate; and
- b) transfecting the cells by adding to the culture of (a) a composition comprising one or more polynucleotides and a transfection reagent.

[2.] A method of producing a recombinant polypeptide, comprising:
- a) providing a cell culture comprising cells suitable for producing the recombinant polypeptide, wherein the culture comprises between about 0.1 mg/L and about 10 mg/L dextran sulfate;
- b) transfecting the cells by adding to the culture of a) a composition comprising one or more polynucleotides encoding the polypeptide and a transfection reagent; and
- c) maintaining the cell culture comprising the transfected cells under conditions that allow the production of the recombinant polypeptide.

[3.] The method of [2], wherein the polypeptide is an antibody or antigen-binding fragment thereof, bispecific antibody, enzyme, fusion protein or Fc fusion protein.

[4.] A method of producing a recombinant virus particle, comprising:
- a) providing a cell culture comprising cells suitable for producing the recombinant virus particle, wherein the culture comprises between about 0.1 mg/L and about 10 mg/L dextran sulfate;
- b) transfecting the cells by adding to the culture of a) a composition comprising one or more polynucleotides containing genes necessary for producing the recombinant virus particle and a transfection reagent; and
- c) maintaining the cell culture comprising the transfected cells under conditions that allow the production of the recombinant virus particle.

[5.] The method of any one of [1] to [4], wherein the culture of a) comprises between about 0.5 mg/L and about 10 mg/L, between about 0.5 mg/L and about 5 mg/L, between about 0.5 mg/L and about 3 mg/L, between about 1 mg/L and about 10 mg/L, between about 1 mg/L and about 5 mg/L, between about 1 mg/L and about 4 mg/L, or between about 1 mg/L and about 3 mg/L dextran sulfate.

[6.] The method of any one of [1] to [4], wherein the culture of a) comprises about 0.5 mg/L, about 1 mg/L, about 1.5 mg/L, about 2 mg/L, about 2.5 mg/L, about 3 mg/L, about 4 mg/L, or about 5 mg/L dextran sulfate.

[7.] The method of any one of [1] to [4], wherein the culture of a) comprises about 2 mg/L dextran sulfate.

[8.] A method of transfecting cells, comprising:
- a) culturing the cells in a cell culture, wherein the culture comprises a starting dextran sulfate concentration of between about 1 mg/L and about 20 mg/L and a final dextran sulfate concentration of between about 0.1 mg/L and about 10 mg/L; and b) transfecting the cells by adding to the culture of a) a composition comprising one or more polynucleotides and a transfection reagent.

[9.] A method of producing a recombinant polypeptide, comprising:

a) culturing cells suitable for producing the recombinant polypeptide in a cell culture, wherein the culture comprises a starting dextran sulfate concentration of between about 1 mg/L and about 20 mg/L and a final dextran sulfate concentration of between about 0.1 mg/L and about 10 mg/L;

b) transfecting the cells by adding to the culture of a) a composition comprising one or more polynucleotides encoding the polypeptide and a transfection reagent; and c) maintaining the cell culture comprising the transfected cells under conditions that allow the production of the recombinant polypeptide.

[10.] The method of [9], wherein the polypeptide is an antibody or antigen-binding fragment thereof, bispecific antibody, enzyme, fusion protein or Fc fusion protein.

[11.] A method of producing a recombinant virus particle, comprising:

a) culturing cells suitable for producing the recombinant virus particle in a cell culture for between about 1 day and about 5 days, wherein the culture comprises a starting dextran sulfate concentration of between about 1 mg/L and about 20 mg/L and a final dextran sulfate concentration of between about 0.1 mg/L and about 10 mg/L;

b) transfecting the cells by adding to the culture of a) a composition comprising one or more polynucleotides containing genes necessary for producing the recombinant virus particle and a transfection reagent; and c) maintaining the cell culture comprising the transfected cells under conditions that allow the production of the recombinant virus particle.

[12.] The method of any one of [8] to [11], wherein the starting dextran sulfate concentration is between about 1 mg/L and about 10 mg/L, between about 1 mg/L and about 5 mg/L, between about 2 mg/L and about 10 mg/L, between about 3 mg/L and about 10 mg/L, or between about 3 mg/L and about 5 mg/L.

[13.] The method of any one of [8] to [11], wherein the starting dextran sulfate concentration is about 2 mg/L, about 3 mg/L, about 4 mg/L, about 5 mg/L, about 6 mg/L, about 7 mg/L, about 8 mg/L, about 9 mg/L, or about 10 mg/L.

[14.] The method of any one of [8] to [11], wherein the starting dextran sulfate.concentration is about 4 mg/L.

[15.] The method of any one of [8] to [14], wherein the final dextran sulfate concentration is between about 0.5 mg/L and about 10 mg/L, between about 0.5 mg/L and about 5 mg/L, between about 0.5 mg/L and about 5 mg/L, between about 0.5 mg/L and about 3 mg/L, between about 1 mg/L and about 10 mg/L, between about 1 mg/L and about 5 mg/L, between about 1 mg/L and about 4 mg/L, or between about 1 mg/L and about 3 mg/L.

[16.] The method of any one of [8] to [14], wherein the final dextran sulfate concentration is about 0.5 mg/L, about 1 mg/L, about 1.5 mg/L, about 2 mg/L, about 2.5 mg/L, about 3 mg/L, about 4 mg/L, or about 5 mg/L.

[17.] The method of any one of [8] to [14], wherein the final dextran sulfate concentration is about 2 mg/L.

[18.] The method of any one of [8] to [11], wherein the starting dextran sulfate concentration is about 4 mg/L and the final dextran sulfate concentration is about 2 mg/L.

[19.] The method of any one of [4] to [7] and to [18], wherein the recombinant virus particle is a recombinant adeno-associated virus (rAAV) particle or a recombinant lentivirus particle.

[20.] The method of any one of [4] to [7] and to [18], wherein the recombinant virus particle is an rAAV particle.

[21.] The method of [20], wherein the rAAV particle comprises a capsid protein of the AAV1, AAV2, AAV3, AAV4, AAV5, AAV6, AAV7, AAV8, AAV9, AAV10, AAV11, AAV12, AAV13, AAV14, AAV15, AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 serotype.

[22.] The method of [20], wherein the rAAV particle comprises a capsid protein of the AAV8, AAV9, AAV.rh10, AAV.rh20, AAV.rh39, AAV.Rh74, AAV.RHM4-1, or AAV.hu37 serotype.

[23.] The method of [20], wherein the rAAV particles comprise a capsid protein of the AAV8 or AAV9 serotype.

[24.] The method of any one of to [23], wherein the rAAV particle comprises a genome comprising a transgene.

[25.] The method of [24], wherein the transgene comprises a regulatory element operatively connected to a polynucleotide encoding a polypeptide.

[26.] The method of [25], wherein the regulatory element comprises one or more of an enhancer, promoter, and polyA region.

[27.] The method of or [25], wherein the regulatory element and polynucleotide encoding a polypeptide are heterologous.

[28.] The method of any one of to [27], wherein the transgene encodes an anti-VEGF Fab, iduronidase (IDUA), iduronate 2-sulfatase (IDS), low-density lipoprotein receptor (LDLR), tripeptidyl peptidase 1 (TPP1), or non-membrane associated splice variant of VEGF receptor 1 (sFlt-1).

[29.] The method of any one of to [27], wherein the transgene encodes an gamma-sarcoglycan, Rab Escort Protein 1 (REP1/CHM), retinoid isomerohydrolase (RPE65), cyclic nucleotide gated channel alpha 3 (CNGA3), cyclic nucleotide gated channel beta 3 (CNGB3), aromatic L-amino acid decarboxylase (AADC), lysosome-associated membrane protein 2 isoform B (LAMP2B), Factor VIII, Factor IX, retinitis pigmentosa GTPase regulator (RPGR), retinoschisin (RS1), sarcoplasmic reticulum calcium ATPase (SERCA2a), aflibercept, battenin (CLN3), transmembrane ER protein (CLN6), glutamic acid decarboxylase (GAD), Glial cell line-derived neurotrophic factor (GDNF), aquaporin 1 (AQP1), dystrophin, minidystrophin, microdystrophin, myotubularin 1 (MTM1), follistatin (FST), glucose-6-phosphatase (G6Pase), apolipoprotein A2 (APOA2), uridine diphosphate glucuronosyl transferase 1A1 (UGT1A1), arylsulfatase B (ARSB), N-acetyl-alpha-glucosaminidase (NAGLU), alpha-glucosidase (GAA), alpha-galactosidase (GLA), beta-galactosidase (GLB1), lipoprotein lipase (LPL), alpha 1-antitrypsin (AAT), phosphodiesterase 6B (PDE6B), ornithine carbamoyltransferase 90TC), survival motor neuron (SMN1), survival motor neuron (SMN2), neurturin (NRTN), Neurotrophin-3 (NT-3/NTF3), porphobilinogen deaminase (PBGD), nerve growth factor (NGF), mitochondrially encoded NADH: ubiquinone oxidoreductase core subunit 4 (MT-ND4), protective protein cathepsin A (PPCA), dysferlin, MER proto-oncogene, tyrosine kinase (MERTK), cystic fibrosis transmembrane conductance regulator (CFTR), or tumor necrosis factor receptor (TNFR)-immunoglobulin (IgG1) Fc fusion.

[30.] The method of any one of to [29], wherein the one or more polynucleotide encode
a) an rAAV genome to be packaged,
b) adenovirus helper functions necessary for packaging,
c) an AAV rep protein sufficient for packaging, and
d) an AAV cap proteins sufficient for packaging.

[31.] The method of [30], wherein the one or more polynucleotide comprises a polynucleotide encoding the rAAV genome, a polynucleotide encoding the AAV rep protein and the AAV cap proteins, and a polynucleotide encoding the adenovirus helper functions.

[32.] The method of or [31], wherein the adenovirus helper functions comprise at least one of an adenovirus E1a gene, E1b gene, E4 gene, E2a gene, and VA gene.

[33.] The method of any one of to [28], further comprising recovering the rAAV particles.

[34.] The method of any one of to [33], wherein the cell culture produces between about 5x10e+10 GC/ml and about 1x10e+12 GC/ml rAAV particles.

[35.] The method of any one of to [33], wherein the cell culture produces at least about 1.1 times, 1.2 times, 1.3 times, 1.4 times, 1.5 times, 1.6 times, 1.7 times, 1.8 times, 1.9 times or 2 times as many rAAV particles measured as GC/ml than a reference method in which the culture of a) does not comprises dextran sulfate.

[36.] The method of any one of [1] to [35], wherein the cell culture is a suspension cell culture.

[37.] The method of [36], wherein the cell culture comprises suspension adapted cells.

[38.] The method of or [37], wherein the cells comprise HEK293 cells, HEK derived cells, CHO cells, CHO derived cells, HeLa cells, SF-9 cells, BHK cells, Vero cells, and/or PerC6 cells, or combinations thereof.

[39.] The method of or [37], wherein the cells comprise HEK293 cells.

[40.] The method of or [37], wherein the cells comprise CHO cells or CHO-K1 cells.

[41.] The method of anyone of [1] to [40], wherein the transfection reagent comprises a lipid, polymer, peptide, or a combination thereof.

[42.] The method of [41], wherein the transfection reagent comprises a lipid, wherein the lipid comprises DOTMA, DOTAP, DOSPA, DOGS or a combination thereof.

[43.] The method of [41], wherein the transfection reagent comprises a polymer, wherein the polymer comprises poly (L-Lysine) (PLL), polyethylenimine (PEI), a polysaccharide, Poly [2-(dimethylamino)ethyl methacrylate] (PDMAEMA), a dendrimer, or a combination thereof.

[44.] The method of [41], wherein the transfection reagent comprises polyethylenimine (PEI).

[45.] The method of anyone of [1] to [44], wherein the cell culture has a volume of between about 50 liters and about 20,000 liters.

[46.] The method of [45], wherein the cell culture has a volume between about 50 liters and about 5,000 liters.

[47.] The method of [45], wherein the cell culture has a volume between about 50 liters and about 2,000 liters.

[48.] The method of [45], wherein the cell culture has a volume between about 50 liters and about 1,000 liters.

[49.] The method of [41], wherein the cell culture has a volume between about 50 liters and about 500 liters.

[50.] A composition comprising isolated rAAV particles that were produced by the method of any one of [20] to [49].

Still other features and advantages of the compositions and methods described herein will become more apparent from the following detailed description when read in conjunction with the accompanying drawings.

DETAILED DESCRIPTION

Figure 1:
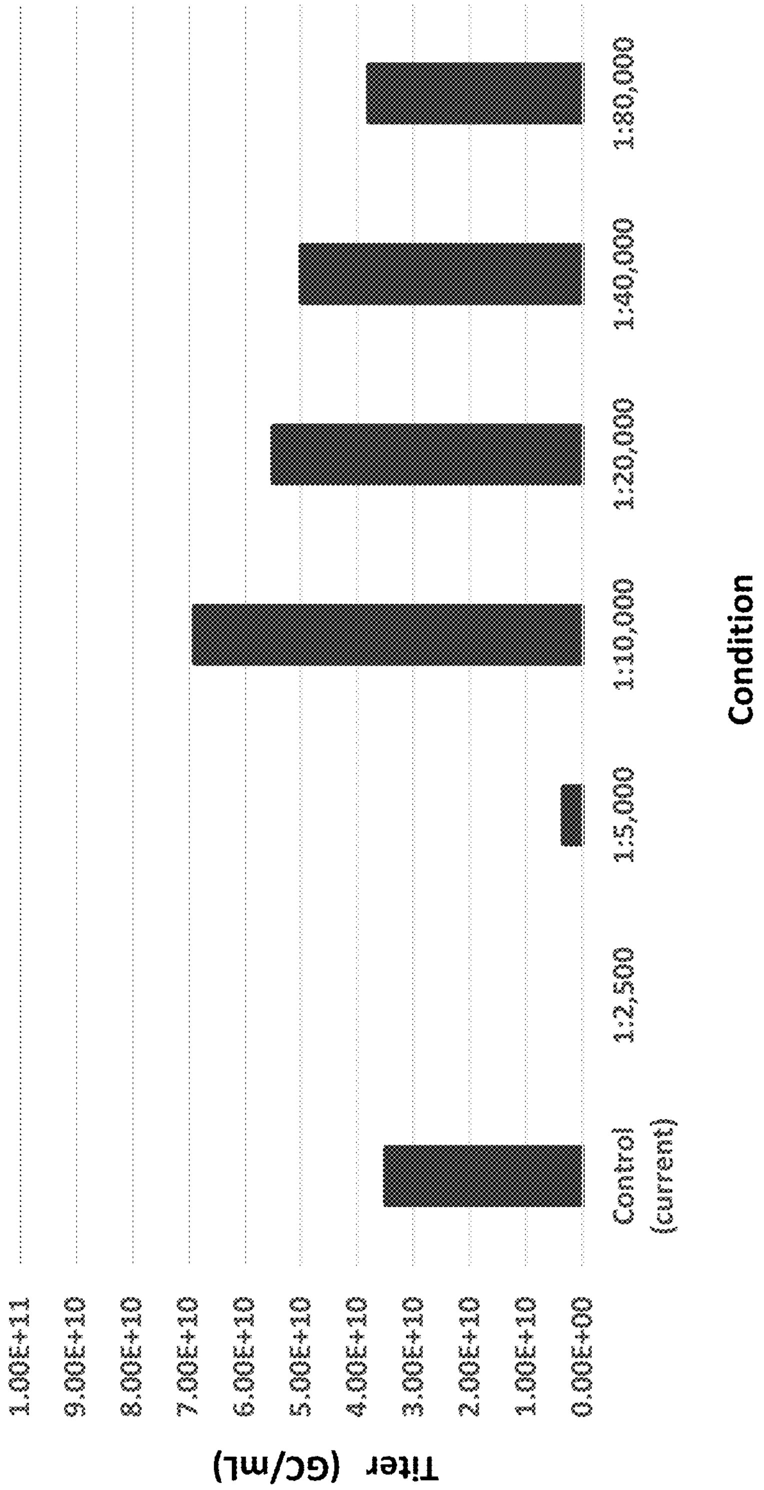
FIG. 1. Initial shake flask screen of dextran sulfate for use prior to and during transfection. 1:2,500, 1:500, 1:10,000, 1:20,000, 1:40,000 and 1:80,000 indicate the dilution factor of 25 g/L dextran sulfate stock solution present at the time of transfection and correspond to a concentration of 10 mg/L, 5 mg/L, 2.5 mg/L, 1.25 mg/L, 625 □g/L, and 313 □g/L, respectively.

It was surprisingly found that dextran sulfate is capable of increasing rAAV titers in a transient transfection based production method. This finding was unexpected because dextran sulfate was known to interfere with transient transfection. For example, Geng et al. (2007) at page 55 concludes that dextran sulfate completely inhibits PEI mediated transfection. Similarly, a recently published "Guide for DNA Transfection in iCELLis® 500 and iCELLis 500+ Bioreactors for Large Scale Gene Therapy Vector Manufacturing" by PALL® Biotech ("2020 Guide") teaches at page 9 that dextran sulfate inhibits PEI mediated transfection. A skilled artisan considering, for example, the teachings of Geng et al. (2007) and the 2020 Guide would have reasonably expected that rAAV production by a transient transfection-based method would be inhibited, or at least made less productive by the presence of dextran sulfate in the cell culture during transfection. In contrast, as discussed in the Examples, the presence of dextran sulfate to presence of dextran sulfate in the transfection medium surprisingly increased rAAV production. Increased rAAV production was observed in processes for the production of rAAV particles comprising different capsid serotypes or transgenes using different cell culture medium, host cell clones and production volumes.

These surprising findings were used to develop methods of transfecting cells, producing a recombinant polypeptide, producing a recombinant virus particle (e.g., recombinant adeno-associated virus (rAAV) particle), improving the production of a recombinant polypeptide, and improving the production of a recombinant virus particle (e.g., rAAV particle) described herein. In some embodiments, the methods comprise transfecting cells by adding to a culture comprising cells and dextran sulfate a composition comprising one or more polynucleotides and a transfection reagent. In some embodiments, the cell culture is a suspension cell culture. In some embodiments, the cell culture comprises adherent cells growing attached to microcarriers or macrocarriers in stirred bioreactors. In some embodiments, the cell culture is a suspension cell culture comprising suspension-adapted HEK293 cells. In some embodiments, the recombinant virus particles are recombinant adeno-associated virus (rAAV) particles. In some embodiments, the rAAV comprises a capsid protein of the AAV1, AAV2, AAV3, AAV4, AAV5, AAV6, AAV7, AAV8, AAV9, AAV10, AAV11, AAV12, AAV13, AAV14, AAV15, AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 serotype. In some embodiments, the rAAV comprises a capsid protein of the AAV8 or AAV9 serotype.

Given the very high number of rAAV particles needed to prepare a single therapeutic unit dose, any increase in rAAV yield provides a reduction in the cost of goods per unit dose. Increased virus yield allows a corresponding reduction not only in the cost of consumables needed to produce rAAV particles, but also in the cost of capital expenditure in connection with building industrial virus purification facilities.

Definitions

Unless defined otherwise, all technical and scientific terms used herein have the same meaning as commonly understood by one of ordinary skill in the art to which this disclosure is related. To facilitate an understanding of the disclosed methods, a number of terms and phrases are defined below.

"About" modifying, for example, the quantity of an ingredient in the compositions, concentration of an ingredient in the compositions, flow rate, rAAV particle yield, feed volume, salt concentration, and like values, and ranges thereof, employed in the methods provided herein, refers to variation in the numerical quantity that can occur, for example, through typical measuring and handling procedures used for making concentrates or use solutions; through inadvertent error in these procedures; through differences in the manufacture, source, or purity of the ingredients employed to make the compositions or carry out the methods; and like considerations. The term "about" also encompasses amounts that differ due to aging of a composition with a particular initial concentration or mixture. The term "about" also encompasses amounts that differ due to mixing or processing a composition with a particular initial concentration or mixture. Whether or not modified by the term "about" the claims include equivalents to the quantities. In some embodiments, the term "about" refers to ranges of approximately 10-20% greater than or less than the indicated number or range. In further embodiments, "about" refers to plus or minus 10% of the indicated number or range. For example, "about 10%" indicates a range of 9% to 11%.

The term "dextran sulfate" refers to a sulfated polysaccharide, comprising a polymer main chain of α-1,6 glycosidic linkages between glucose monomers, and branches from α-1,3 linkages. Dextran sulfate can be obtained commercially, for example from MilliporeSigma (Saint Louis, Mo.). It is understood that "dextran sulfate" encompasses both the free acid and salts thereof. In some embodiments, dextran sulfate is a salt. In some embodiments, dextran sulfate is a free acid. In some embodiments, dextran sulfate is a salt comprising a monovalent cation. In some embodiments, dextran sulfate is a Li, Na, K, Rb, or Cs salt. In some embodiments, dextran sulfate is a Na salt. In some embodiments, dextran sulfate contains about 10% to about 25% sulfur. In some embodiments, dextran sulfate contains about 15% to about 20% sulfur. In some embodiments, each glucosyl residue of dextran sulfate contains on average from 1 to 3 sulfate groups. In some embodiments, each glucosyl residue of dextran sulfate contains on average from 2 to 3 sulfate groups. In some embodiments, dextran sulfate contains about 17% sulfur which is equivalent to approximately 2.3 sulfate groups per glucosyl residue. In some embodiments, the average molecular weight of dextran sulfate is about 3 kDa to about 500 kDa, about 3 kDa to about 250 kDa, about 3 kDa to about 100 kDa, about 3 kDa to about 50 kDa, about 3 kDa to about 25 kDa, or about 3 kDa to about 10 kDa. In some embodiments, the average molecular weight of dextran sulfate is about 5 kDa to about 500 kDa, about 5 kDa to about 250 kDa, about 5 kDa to about 100 kDa, about 5 kDa to about 50 kDa, about 5 kDa to about 25 kDa, or about 5 kDa to about 10 kDa. In some embodiments, the average molecular weight of dextran sulfate is about 3 kDa to about 25 kDa. In some embodiments, the average molecular weight of dextran sulfate is about 3 kDa to about 10 kDa. In some embodiments, the average molecular weight of dextran sulfate is about 4 kDa to about 25 kDa. In some embodiments, the average molecular weight of dextran sulfate is about 4 kDa to about 10 kDa. In some embodiments, the average molecular weight of dextran sulfate is about 5 kDa to about 25 kDa. In some embodiments, the average molecular weight of dextran sulfate is about 5 kDa to about 10 kDa. In some embodiments, the average molecular weight of dextran sulfate is about 5 kDa. In some embodiments, dextran sulfate is a sodium salt with an average molecular weight of between about 3 kDa and 10 kDa. In some embodiments, dextran sulfate is a sodium salt with an average molecular weight of about 5 kDa. In some embodiments, dextran sulfate is a sodium salt, contains about 15% to 20% sulfur, and has an average molecular weight of between about 3 kDa and 10 kDa. In some embodiments, dextran sulfate is a sodium salt, contains about 17% sulfur, and has an average molecular weight of about 5 kDa.

"AAV" is an abbreviation for adeno-associated virus, and may be used to refer to the virus itself or modifications, derivatives, or pseudotypes thereof. The term covers all subtypes and both naturally occurring and recombinant forms, except where required otherwise. The abbreviation "rAAV" refers to recombinant adeno-associated virus. The term "AAV" includes AAV type 1 (AAV1), AAV type 2 (AAV2), AAV type 3 (AAV3), AAV type 4 (AAV4), AAV type 5 (AAV5), AAV type 6 (AAV6), AAV type 7 (AAV7), AAV type 8 (AAV8), AAV type 9 (AAV9), avian AAV, bovine AAV, canine AAV, equine AAV, primate AAV, non-primate AAV, and ovine AAV, and modifications, derivatives, or pseudotypes thereof. "Primate AAV" refers to AAV that infect primates, "non-primate AAV" refers to AAV that infect non-primate mammals, "bovine AAV" refers to AAV that infect bovine mammals, etc.

"Recombinant", as applied to an AAV particle means that the AAV particle is the product of one or more procedures that result in an AAV particle construct that is distinct from an AAV particle in nature.

A recombinant adeno-associated virus particle "rAAV particle" refers to a viral particle composed of at least one AAV capsid protein and an encapsidated polynucleotide rAAV vector genome comprising a heterologous polynucleotide (i.e. a polynucleotide other than a wild-type AAV genome such as a transgene to be delivered to a mammalian cell). The rAAV particle may be of any AAV serotype, including any modification, derivative or pseudotype (e.g., AAV1, AAV2, AAV3, AAV4, AAV5, AAV6, AAV7, AAV8, AAV9, or AAV10, or derivatives/modifications/pseudotypes thereof). Such AAV serotypes and derivatives/modifications/pseudotypes, and methods of producing such serotypes/derivatives/modifications/pseudotypes are known in the art (see, e.g., Asokan et al., Mol. Ther. 20 (4): 699-708 (2012).

The rAAV particles of the disclosure may be of any serotype, or any combination of serotypes, (e.g., a population of rAAV particles that comprises two or more serotypes, e.g., comprising two or more of rAAV2, rAAV8, and rAAV9 particles). In some embodiments, the rAAV particles are rAAV1, rAAV2, rAAV3, rAAV4, rAAV5, rAAV6, rAAV7, rAAV8, rAAV9, rAAV10, or other rAAV particles, or combinations of two or more thereof). In some embodiments, the rAAV particles are rAAV8 or rAAV9 particles.

In some embodiments, the rAAV particles have an AAV capsid protein of a serotype selected from the group consisting of AAV1, AAV2, AAV3, AAV4, AAV5, AAV6, AAV7, AAV8, AAV9, AAV10, AAV11, AAV12, AAV13, AAV14, AAV15, AAV16 or a derivative, modification, or pseudotype thereof. In some embodiments, the rAAV particles have an AAV capsid protein of a serotype of AAV8, AAV9, or a derivative, modification, or pseudotype thereof.

The term "cell culture," refers to cells grown adherent or in suspension, bioreactors, roller bottles, hyperstacks, microspheres, macrospheres, flasks and the like, as well as the components of the supernatant or suspension itself, including but not limited to rAAV particles, cells, cell debris, cellular contaminants, colloidal particles, biomolecules, host cell proteins, nucleic acids, and lipids, and flocculants. Large scale approaches, such as bioreactors, including suspension cultures and adherent cells growing attached to microcarriers or macrocarriers in stirred bioreactors, are also encompassed by the term "cell culture." Cell culture procedures for both large and small-scale production of proteins are encompassed by the present disclosure. In some embodiments, the term "cell culture" refers to cells grown in suspension. In some embodiments, the term "cell culture" refers to adherent cells grown attached to microcarriers or macrocarriers in stirred bioreactors. In some embodiments, the term "cell culture" refers to cells grown in a perfusion culture. In some embodiments, the term "cell culture" refers to cells grown in an alternating tangential flow (ATF) supported high-density perfusion culture.

The terms "purifying", "purification", "separate", "separating", "separation", "isolate", "isolating", or "isolation", as used herein, refer to increasing the degree of purity of a target product, e.g., rAAV particles and rAAV genome from a sample comprising the target product and one or more impurities. Typically, the degree of purity of the target product is increased by removing (completely or partially) at least one impurity from the sample. In some embodiments, the degree of purity of the rAAV in a sample is increased by removing (completely or partially) one or more impurities from the sample by using a method described herein.

As used in the present disclosure and claims, the singular forms "a", "an" and "the" include plural forms unless the context clearly dictates otherwise.

It is understood that wherever embodiments are described herein with the language "comprising" otherwise analogous embodiments described in terms of "consisting of" and/or "consisting essentially of" are also provided. It is also understood that wherever embodiments are described herein with the language "consisting essentially of" otherwise analogous embodiments described in terms of "consisting of" are also provided.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Where embodiments of the disclosure are described in terms of a Markush group or other grouping of alternatives, the disclosed method encompasses not only the entire group listed as a whole, but also each member of the group individually and all possible subgroups of the main group, and also the main group absent one or more of the group members. The disclosed methods also envisage the explicit exclusion of one or more of any of the group members in the disclosed methods.

Methods of Transfecting Cells

In one aspect, the disclosure provides a method of transfecting cells, comprising (a) providing a cell culture comprising the cells, wherein the culture comprises between about 0.1 mg/L and about 10 mg/L dextran sulfate; and (b) transfecting the cells by adding to the culture of (a) a composition comprising one or more polynucleotides and a transfection reagent.

In some embodiments, the culture of a) comprises between about 0.5 mg/L and about 10 mg/L, between about 0.5 mg/L and about 5 mg/L, between about 0.5 mg/L and about 3 mg/L, between about 1 mg/L and about 10 mg/L, between about 1 mg/L and about 5 mg/L, between about 1 mg/L and about 4 mg/L, or between about 1 mg/L and about 3 mg/L dextran sulfate. In some embodiments, the culture of a) comprises between about 0.5 mg/L and about 5 mg/L dextran sulfate. In some embodiments, the culture of a) comprises between about 1 mg/L and about 5 mg/L dextran sulfate. In some embodiments, the culture of a) comprises between about 1 mg/L and about 3 mg/L dextran sulfate.

In some embodiments, the culture of a) comprises about 0.5 mg/L, about 1 mg/L, about 1.5 mg/L, about 2 mg/L, about 2.5 mg/L, about 3 mg/L, about 4 mg/L, or about 5 mg/L dextran sulfate. In some embodiments, the culture of a) comprises about 1 mg/L dextran sulfate. In some embodiments, the culture of a) comprises about 1.5 mg/L dextran sulfate. In some embodiments, the culture of a) comprises about 2 mg/L dextran sulfate. In some embodiments, the culture of a) comprises about 2.5 mg/L dextran sulfate. In some embodiments, the culture of a) comprises about 3 mg/L dextran sulfate. In some embodiments, the culture of a) comprises about 3.5 mg/L dextran sulfate. In some embodiments, the culture of a) comprises about 4 mg/L dextran sulfate.

In some embodiments, the culture of a) comprises about 2 mg/L dextran sulfate.

In some embodiments, the disclosure provides a method of transfecting cells, comprising (a) culturing the cells in a cell culture, wherein the culture comprises a starting dextran sulfate concentration of between about 1 mg/L and about 20 mg/L and a final dextran sulfate concentration of between about 0.1 mg/L and about 10 mg/L; and (b) transfecting the cells by adding to the culture of a) a composition comprising one or more polynucleotides and a transfection reagent.

In some embodiments, the starting dextran sulfate concentration is between about 1 mg/L and about 10 mg/L, between about 1 mg/L and about 5 mg/L, between about 2 mg/L and about 10 mg/L, between about 3 mg/L and about 10 mg/L, or between about 3 mg/L and about 5 mg/L dextran sulfate. In some embodiments, the starting dextran sulfate concentration is between about 1 mg/L and about 10 mg/L dextran sulfate. In some embodiments, the starting dextran sulfate concentration is between about 2 mg/L and about 10 mg/L dextran sulfate. In some embodiments, the starting dextran sulfate concentration is between about 3 mg/L and about 6 mg/L dextran sulfate.

In some embodiments, the starting dextran sulfate concentration is about 2 mg/L, about 3 mg/L, about 4 mg/L, about 5 mg/L, about 6 mg/L, about 7 mg/L, about 8 mg/L, about 9 mg/L, or about 10 mg/L dextran sulfate. In some embodiments, the starting dextran sulfate concentration is about 2 mg/L dextran sulfate. In some embodiments, the starting dextran sulfate concentration is about 3 mg/L dextran sulfate. In some embodiments, the starting dextran sulfate concentration is about 4 mg/L dextran sulfate. In some embodiments, the starting dextran sulfate concentration is about 5 mg/L dextran sulfate. In some embodiments, the starting dextran sulfate concentration is about 6 mg/L dextran sulfate. In some embodiments, the starting dextran sulfate concentration is about 7 mg/L dextran sulfate. In some embodiments, the starting dextran sulfate concentration is about 8 mg/L dextran sulfate.

In some embodiments, the starting dextran sulfate concentration is about 4 mg/L dextran sulfate.

In some embodiments, the final dextran sulfate concentration is between about 0.5 mg/L and about 10 mg/L, between about 0.5 mg/L and about 5 mg/L, between about 0.5 mg/L and about 3 mg/L, between about 1 mg/L and about 10 mg/L, between about 1 mg/L and about 5 mg/L, between about 1 mg/L and about 4 mg/L, or between about 1 mg/L and about 3 mg/L dextran sulfate. In some embodiments, the final dextran sulfate concentration is between about 0.5 mg/L and about 5 mg/L dextran sulfate. In some embodiments, the final dextran sulfate concentration is between about 1 mg/L and about 5 mg/L dextran sulfate. In some embodiments, the final dextran sulfate concentration is between about 1 mg/L and about 3 mg/L dextran sulfate.

In some embodiments, the final dextran sulfate concentration is about 0.5 mg/L, about 1 mg/L, about 1.5 mg/L, about 2 mg/L, about 2.5 mg/L, about 3 mg/L, about 4 mg/L, or about 5 mg/L dextran sulfate. In some embodiments, the final dextran sulfate concentration is about 1 mg/L dextran sulfate. In some embodiments, the final dextran sulfate concentration is about 1.5 mg/L dextran sulfate. In some embodiments, the final dextran sulfate concentration is about 2 mg/L dextran sulfate. In some embodiments, the final dextran sulfate concentration is about 2.5 mg/L dextran sulfate. In some embodiments, the final dextran sulfate concentration is about 3 mg/L dextran sulfate. In some embodiments, the final dextran sulfate concentration is about 3.5 mg/L dextran sulfate. In some embodiments, the final dextran sulfate concentration is about 4 mg/L dextran sulfate.

In some embodiments, the final dextran sulfate concentration is about 2 mg/L dextran sulfate.

In some embodiments, the starting dextran sulfate concentration is between about 1 mg/L and about 10 mg/L, between about 1 mg/L and about 5 mg/L, between about 2 mg/L and about 10 mg/L, between about 3 mg/L and about 10 mg/L, or between about 3 mg/L and about 5 mg/L dextran sulfate, and the final dextran sulfate concentration is between about 0.5 mg/L and about 10 mg/L, between about 0.5 mg/L and about 5 mg/L, between about 0.5 mg/L and about 3 mg/L, between about 1 mg/L and about 10 mg/L, between about 1 mg/L and about 5 mg/L, between about 1 mg/L and about 4 mg/L, or between about 1 mg/L and about 3 mg/L dextran sulfate. In some embodiments, the starting dextran sulfate concentration is between about 3 mg/L and about 6 mg/L dextran sulfate, and the final dextran sulfate concentration is between about 1 mg/L and about 3 mg/L dextran sulfate.

In some embodiments, the starting dextran sulfate concentration is about 2 mg/L, about 3 mg/L, about 4 mg/L, about 5 mg/L, about 6 mg/L, about 7 mg/L, about 8 mg/L, about 9 mg/L, or about 10 mg/L dextran sulfate, and the final dextran sulfate concentration is about 0.5 mg/L, about 1 mg/L, about 1.5 mg/L, about 2 mg/L, about 2.5 mg/L, about 3 mg/L, about 4 mg/L, or about 5 mg/L dextran sulfate.

In some embodiments, the starting dextran sulfate concentration is about 4 mg/L dextran sulfate, and the final dextran sulfate concentration is about 2 mg/L dextran sulfate.

In some embodiments, the one or more polynucleotides comprise a transgene. In some embodiments, the transgene comprises a regulatory element operatively connected to a polynucleotide encoding a polypeptide. In some embodiments, the polypeptide comprises an antibody or antigen-binding fragment thereof, bispecific antibody, enzyme, fusion protein or Fc fusion protein. In some embodiments, the polypeptide comprises an antibody or antigen-binding fragment thereof.

In some embodiments, the one or more polynucleotides comprise genes necessary for producing a recombinant virus particle. In some embodiments, the recombinant virus particle is a recombinant adeno virus particle. In some embodiments, the recombinant virus particle is a recombinant adeno-associated virus (rAAV) particle.

Any suitable transfection reagent known in the art for transfecting a cell may be used. In some embodiments, the transfection reagent comprises a cationic organic carrier. See, e.g., Gigante et al., Medchemcomm 10 (10): 1692-1718 (2019); Damen et al. Medchemcomm 9 (9): 1404-1425 (2018), each of which is incorporated herein by reference in its entirety. In some embodiments, the cationic organic carrier comprises a lipid, for example, DOTMA, DOTAP, helper lipids (Dope, cholesterol), and combinations thereof. In some embodiments, the cationic organic carrier comprises a multivalent cationic lipid, for example, DOSPA, DOGS, and mixtures thereof. In some embodiments, the cationic organic carrier comprises bipolar lipids, or bolaamphiphiles (bolas). In some embodiments, the cationic organic carrier comprises bioreducible and/or dimerizable lipids. In some embodiments, the cationic organic carrier comprises gemini surfactants. In some embodiments, the cationic organic carrier comprises Lipofectin™, Transfectam™, Lipofectamine™, Lipofectamine 2000™, or Lipofectamin PLUS 2000™. In some embodiments, the cationic organic carrier comprises a polymer, for example, poly (L-Lysine) (PLL), polyethylenimine (PEI), polysaccharides (chitosan, dextran, cyclodextrine (CD)), Poly [2-(dimethylamino)ethyl methacrylate] (PDMAEMA), and dendrimers (polyamidoamine (PAMAM), poly(propylene imine) (PPI)). In some embodiments, the cationic organic carrier comprises a peptide, for example, peptides rich in basic amino-acids (CWL18), cell penetrating peptides (CPPs) (Arg-rich peptides (octaarginine, TAT)), nuclear localization signals (NLS) (SV40) and targeting (RGD). In some embodiments, the cationic organic carrier comprises a polymers (e.g., PEI) combined with a cationic liposome. Paris et al., Molecules 25 (14): 3277 (2020), which is incorporated herein by reference in its entirety. In some embodiments, the transfection reagent comprises calcium phosphate, highly branched organic compounds (dendrimers), cationic polymers (e.g., DEAE dextran or polyethylenimine (PEI)), lipofection.

In some embodiments, the transfection reagent comprises poly (L-Lysine) (PLL), polyethylenimine (PEI), linear PEI, branched PEI, dextran, cyclodextrine (CD), Poly [2-(dimethylamino) ethyl methacrylate] (PDMAEMA), polyamidoamine (PAMAM), poly(propylene imine) (PPI)), or mixtures thereof. In some embodiments, the transfection reagent comprises polyethylenimine (PEI), linear PEI, branched PEI, or mixtures thereof. In some embodiments, the transfection reagent comprises polyethylenimine (PEI). In some embodiments, the transfection reagent comprises linear PEI. In some embodiments, the transfection reagent comprises branched PEI. In some embodiments, the transfection reagent comprises polyethylenimine (PEI) having a molecular weight between about 5 and about 25 kDa. In some embodiments, the transfection reagent comprises PEGylated polyethylenimine (PEI). In some embodiments, the transfection reagent comprises modified polyethylenimine (PEI) to which hydrophobic moieties such cholesterol, choline, alkyl groups and some amino acids were attached.

Any cell culture system known in the art can be used. In some embodiments, the cell culture is a suspension cell culture. In some embodiments, the cell culture is an adherent cell culture. In some embodiments, the cell culture comprises adherent cells grown attached to microcarriers or macrocarriers in stirred bioreactors. In some embodiments, the cell culture is a perfusion culture. In some embodiments, the cell culture is an alternating tangential flow (ATF) supported high-density perfusion culture.

In some embodiments, the cells comprise mammalian cells or insect cells. In some embodiments, the cells comprise mammalian cells. In some embodiments, the cells comprise HEK293 cells, HEK derived cells, CHO cells, CHO derived cells, HeLa cells, SF-9 cells, BHK cells, Vero cells, and/or PerC6 cells. In some embodiments, the cells comprise HEK293 cells.

In some embodiments, the cells comprise suspension-adapted cells. In some embodiments, the cells comprise suspension-adapted HeLa cells, HEK293 cells, HEK293 derived cells (e.g., HEK293T cells, HEK293F cells), Vero cells, CHO cells, CHO-K1 cells, CHO derived cells, EB66 cells, BSC cells, HepG2 cells, LLC-MK cells, CV-1 cells, COS cells, MDBK cells, MDCK cells, CRFK cells, RAF cells, RK cells, TCMK-1 cells, LLCPK cells, PK15 cells, LLC-RK cells, MDOK cells, BHK cells, BHK-21 cells, NS-1 cells, MRC-5 cells, WI-38 cells, BHK cells, 3T3 cells, 293 cells, RK cells, Per.C6 cells, chicken embryo cells or SF-9 cells. In some embodiments, the cells comprise suspension-adapted HEK293 cells, HEK293 derived cells (e.g., HEK293T cells, HEK293F cells), CHO cells, CHO-K1 cells, or CHO derived cells. In some embodiments, the cells comprise suspension-adapted HEK293 cells. In some embodiments, the cells comprise suspension-adapted CHO cells.

In some embodiments, the cell culture has a volume of between about 50 liters and about 20,000 liters. In some embodiments, the cell culture has a volume between about 50 liters and about 5,000 liters. In some embodiments, the cell culture has a volume between about 50 liters and about 2,000 liters. In some embodiments, the cell culture has a volume between about 50 liters and about 1,000 liters. In some embodiments, the cell culture has a volume between about 50 liters and about 500 liters.

Without being bound by any particular theory, methods disclosed herein increase the efficiency of transfection such that cells transfected according to a method disclosed herein are more likely to comprise the one or more polynucleotides than control cells transfected in a cell culture not comprising dextran sulfate. In some embodiments, a method disclosed herein provides at least about a 10%, at least about a 20%, at least about a 30%, at least about a 40%, or at least about a 50% increase in transfection efficiency compared to a control method using a cell culture that does not comprise dextran sulfate. Methods of measuring transfection efficiency are well known in the art. In some embodiments, transfection efficiency is measured using a reporter transgene construct, for example, a reporter transgene encoding a fluorescent protein (e.g., GFP).

Methods of Producing a Recombinant Viral Particle

In one aspect, the disclosure provides a method of producing a recombinant virus particle, comprising (a) providing a cell culture comprising cells suitable for producing the recombinant virus particle, wherein the culture comprises between about 0.1 mg/L and about 10 mg/L dextran sulfate;

(b) transfecting the cells by adding to the culture of a) a composition comprising one or more polynucleotides containing genes necessary for producing the recombinant virus particle and a transfection reagent; and (c) maintaining the cell culture comprising the transfected cells under conditions that allow the production of the recombinant virus particle. In some embodiments, the culture of a) comprises between about 1 mg/L and about 3 mg/L dextran sulfate. In some embodiments, the recombinant virus particle is a recombinant adeno-associated virus (rAAV) particle. In some embodiments, the one or more polynucleotides comprise one or more helper genes, rep genes, cap genes and transgenes (for example genes of interest or the rAAV genome to be packaged). In some embodiments, the one or more polynucleotides comprise a mixture of three polynucleotides: one encoding the cap and rep genes, one encoding adenovirus helper functions necessary for packaging (e.g., adenovirus E1a gene, E1b gene, E4 gene, E2a gene, and VA gene), and one encoding the rAAV genome to be packaged. In some embodiments, the rAAV particles are AAV8 or AAV9 particles. In some embodiments, the rAAV particles have an AAV capsid protein of a serotype selected from the group consisting of AAV.rh8, AAV.rh10, AAV.rh20, AAV.rh39, AAV.Rh74, AAV.RHM4-1, AAV.hu37, AAV.PHB, and AAV.7m8. In some embodiments, the rAAV particles have an AAV capsid protein with high sequence homology to AAV8 or AAV9 such as, AAV.rh10, AAV.rh20, AAV.rh39, AAV.Rh74, AAV.RHM4-1, and AAV.hu37. In some embodiments, the cell culture is a suspension culture. In some embodiments, the cell culture comprises HEK293 cells adapted for growth in suspension culture. In some embodiments, the cell culture has a volume of between about 400 liters and about 5,000 liters. In some embodiments, the transfection reagent comprises a cationic polymer. In some embodiments, the transfection reagent comprises PEI.

In some embodiments, the disclosure provides a method of increasing the production of a recombinant virus particle, comprising (a) providing a cell culture comprising cells suitable for producing the recombinant virus particle, wherein the culture comprises between about 0.1 mg/L and about 10 mg/L dextran sulfate; (b) transfecting the cells by adding to the culture of a) a composition comprising one or more polynucleotides containing genes necessary for producing the recombinant virus particle and a transfection reagent; and (c) maintaining the cell culture comprising the transfected cells under conditions that allow the production of the recombinant virus particle. In some embodiments, the culture of a) comprises between about 1 mg/L and about 3 mg/L dextran sulfate. In some embodiments, the culture of a) comprises about 2 mg/L dextran sulfate. In some embodiments, the recombinant virus particle is a recombinant adeno-associated virus (rAAV) particle. In some embodiments, the one or more polynucleotides comprise one or more helper genes, rep genes, cap genes and transgenes (for example genes of interest or the rAAV genome to be packaged). In some embodiments, the one or more polynucleotides comprise a mixture of three polynucleotides: one encoding the cap and rep genes, one encoding adenovirus helper functions necessary for packaging (e.g., adenovirus E1a gene, E1b gene, E4 gene, E2a gene, and VA gene), and one encoding the rAAV genome to be packaged. In some embodiments, the rAAV particles are AAV8 or AAV9 particles. In some embodiments, the rAAV particles have an AAV capsid protein of a serotype selected from the group consisting of AAV.rh8, AAV.rh10, AAV.rh20, AAV.rh39, AAV.Rh74, AAV.RHM4-1, AAV.hu37, AAV.PHB, and AAV.7m8.

In some embodiments, the rAAV particles have an AAV capsid protein with high sequence homology to AAV8 or AAV9 such as, AAV.rh10, AAV.rh20, AAV.rh39, AAV.Rh74, AAV.RHM4-1, and AAV.hu37. In some embodiments, the cell culture is a suspension culture. In some embodiments, the cell culture comprises HEK293 cells adapted for growth in suspension culture. In some embodiments, the cell culture has a volume of between about 400 liters and about 5,000 liters. In some embodiments, the transfection reagent comprises a cationic polymer. In some embodiments, the transfection reagent comprises PEI.

In some embodiments, the culture of a) comprises between about 0.5 mg/L and about 10 mg/L, between about 0.5 mg/L and about 5 mg/L, between about 0.5 mg/L and about 3 mg/L, between about 1 mg/L and about 10 mg/L, between about 1 mg/L and about 5 mg/L, between about 1 mg/L and about 4 mg/L, or between about 1 mg/L and about 3 mg/L dextran sulfate. In some embodiments, the culture of a) comprises between about 0.5 mg/L and about 5 mg/L dextran sulfate. In some embodiments, the culture of a) comprises between about 1 mg/L and about 5 mg/L dextran sulfate. In some embodiments, the culture of a) comprises between about 1 mg/L and about 3 mg/L dextran sulfate. In some embodiments, the culture of a) comprises about 2 mg/L dextran sulfate.

In some embodiments, the culture of a) comprises about 0.5 mg/L, about 1 mg/L, about 1.5 mg/L, about 2 mg/L, about 2.5 mg/L, about 3 mg/L, about 4 mg/L, or about 5 mg/L dextran sulfate. In some embodiments, the culture of a) comprises about 1 mg/L dextran sulfate. In some embodiments, the culture of a) comprises about 1.5 mg/L dextran sulfate. In some embodiments, the culture of a) comprises about 2 mg/L dextran sulfate. In some embodiments, the culture of a) comprises about 2.5 mg/L dextran sulfate. In some embodiments, the culture of a) comprises about 3 mg/L dextran sulfate. In some embodiments, the culture of a) comprises about 3.5 mg/L dextran sulfate. In some embodiments, the culture of a) comprises about 4 mg/L dextran sulfate.

In some embodiments, the culture of a) comprises about 2 mg/L dextran sulfate.

In some embodiments, the disclosure provides a method of producing a recombinant virus particle, comprising (a) culturing cells suitable for producing the recombinant virus particle in a cell culture for between about 1 day and about 5 days, wherein the culture comprises a starting dextran sulfate concentration of between about 1 mg/L and about 20 mg/L and a final dextran sulfate concentration of between about 0.1 mg/L and about 10 mg/L; (b) transfecting the cells by adding to the culture of a) a composition comprising one or more polynucleotides containing genes necessary for producing the recombinant virus particle and a transfection reagent; and (c) maintaining the cell culture comprising the transfected cells under conditions that allow the production of the recombinant virus particle. In some embodiments, the starting dextran sulfate concentration is between about 3 mg/L and about 6 mg/L dextran sulfate, and the final dextran sulfate concentration is between about 1 mg/L and about 3 mg/L dextran sulfate. In some embodiments, the starting dextran sulfate concentration is about 4 mg/L dextran sulfate, and the final dextran sulfate concentration is about 2 mg/L dextran sulfate. In some embodiments, the recombinant virus particle is a recombinant adeno-associated virus (rAAV) particle. In some embodiments, the one or more polynucleotides comprise one or more helper genes, rep genes, cap genes and transgenes (for example genes of interest or the rAAV genome to be packaged). In some embodiments, the one or more polynucleotides comprise a mixture of three polynucleotides: one encoding the cap and rep genes, one encoding adenovirus helper functions necessary for packaging (e.g., adenovirus E1a gene, E1b gene, E4 gene, E2a gene, and VA gene), and one encoding the rAAV genome to be packaged. In some embodiments, the rAAV particles are AAV8 or AAV9 particles. In some embodiments, the rAAV particles have an AAV capsid protein of a serotype selected from the group consisting of AAV.rh8, AAV.rh10, AAV.rh20, AAV.rh39, AAV.Rh74, AAV.RHM4-1, AAV.hu37, AAV.PHB, and AAV.7m8. In some embodiments, the rAAV particles have an AAV capsid protein with high sequence homology to AAV8 or AAV9 such as, AAV.rh10, AAV.rh20, AAV.rh39, AAV.Rh74, AAV.RHM4-1, and AAV.hu37. In some embodiments, the cell culture is a suspension culture. In some embodiments, the cell culture comprises HEK293 cells adapted for growth in suspension culture. In some embodiments, the cell culture has a volume of between about 400 liters and about 5,000 liters. In some embodiments, the transfection reagent comprises a cationic polymer. In some embodiments, the transfection reagent comprises PEI.

In some embodiments, the disclosure provides a method of increasing the production of a recombinant virus particle, comprising (a) culturing cells suitable for producing the recombinant virus particle in a cell culture for between about 1 day and about 5 days, wherein the culture comprises a starting dextran sulfate concentration of between about 1 mg/L and about 20 mg/L and a final dextran sulfate concentration of between about 0.1 mg/L and about 10 mg/L; (b) transfecting the cells by adding to the culture of a) a composition comprising one or more polynucleotides containing genes necessary for producing the recombinant virus particle and a transfection reagent; and (c) maintaining the cell culture comprising the transfected cells under conditions that allow the production of the recombinant virus particle. In some embodiments, the starting dextran sulfate concentration is between about 3 mg/L and about 6 mg/L dextran sulfate, and the final dextran sulfate concentration is between about 1 mg/L and about 3 mg/L dextran sulfate. In some embodiments, the starting dextran sulfate concentration is about 4 mg/L dextran sulfate, and the final dextran sulfate concentration is about 2 mg/L dextran sulfate. In some embodiments, the recombinant virus particle is a recombinant adeno-associated virus (rAAV) particle. In some embodiments, the one or more polynucleotides comprise one or more helper genes, rep genes, cap genes and transgenes (for example genes of interest or the rAAV genome to be packaged). In some embodiments, the one or more polynucleotides comprise a mixture of three polynucleotides: one encoding the cap and rep genes, one encoding adenovirus helper functions necessary for packaging (e.g., adenovirus E1a gene, E1b gene, E4 gene, E2a gene, and VA gene), and one encoding the rAAV genome to be packaged. In some embodiments, the rAAV particles are AAV8 or AAV9 particles. In some embodiments, the rAAV particles have an AAV capsid protein of a serotype selected from the group consisting of AAV.rh8, AAV.rh10, AAV.rh20, AAV.rh39, AAV.Rh74, AAV.RHM4-1, AAV.hu37, AAV.PHB, and AAV.7m8. In some embodiments, the rAAV particles have an AAV capsid protein with high sequence homology to AAV8 or AAV9 such as, AAV.rh10, AAV.rh20, AAV.rh39, AAV.Rh74, AAV.RHM4-1, and AAV.hu37. In some embodiments, the cell culture is a suspension culture. In some embodiments, the cell culture comprises HEK293 cells adapted for growth in suspension culture. In some embodiments, the cell culture has a volume of between about 400 liters and about 5,000 liters. In some embodiments, the transfection reagent comprises a cationic polymer. In some embodiments, the transfection reagent comprises PEI.

In some embodiments, the starting dextran sulfate concentration is between about 1 mg/L and about 10 mg/L, between about 1 mg/L and about 5 mg/L, between about 2 mg/L and about 10 mg/L, between about 3 mg/L and about 10 mg/L, or between about 3 mg/L and about 5 mg/L dextran sulfate. In some embodiments, the starting dextran sulfate concentration is between about 1 mg/L and about 10 mg/L dextran sulfate. In some embodiments, the starting dextran sulfate concentration is between about 2 mg/L and about 10 mg/L dextran sulfate. In some embodiments, the starting dextran sulfate concentration is between about 3 mg/L and about 6 mg/L dextran sulfate.

In some embodiments, the starting dextran sulfate concentration is about 2 mg/L, about 3 mg/L, about 4 mg/L, about 5 mg/L, about 6 mg/L, about 7 mg/L, about 8 mg/L, about 9 mg/L, or about 10 mg/L dextran sulfate. In some embodiments, the starting dextran sulfate concentration is about 2 mg/L dextran sulfate. In some embodiments, the starting dextran sulfate concentration is about 3 mg/L dextran sulfate. In some embodiments, the starting dextran sulfate concentration is about 4 mg/L dextran sulfate. In some embodiments, the starting dextran sulfate concentration is about 5 mg/L dextran sulfate. In some embodiments, the starting dextran sulfate concentration is about 6 mg/L dextran sulfate. In some embodiments, the starting dextran sulfate concentration is about 7 mg/L dextran sulfate. In some embodiments, the starting dextran sulfate concentration is about 8 mg/L dextran sulfate.

In some embodiments, the starting dextran sulfate concentration is about 4 mg/L dextran sulfate.

In some embodiments, the final dextran sulfate concentration is between about 0.5 mg/L and about 10 mg/L, between about 0.5 mg/L and about 5 mg/L, between about 0.5 mg/L and about 3 mg/L, between about 1 mg/L and about 10 mg/L, between about 1 mg/L and about 5 mg/L, between about 1 mg/L and about 4 mg/L, or between about 1 mg/L and about 3 mg/L dextran sulfate. In some embodiments, the final dextran sulfate concentration is between about 0.5 mg/L and about 5 mg/L dextran sulfate. In some embodiments, the final dextran sulfate concentration is between about 1 mg/L and about 5 mg/L dextran sulfate. In some embodiments, the final dextran sulfate concentration is between about 1 mg/L and about 3 mg/L dextran sulfate.

In some embodiments, the final dextran sulfate concentration is about 0.5 mg/L, about 1 mg/L, about 1.5 mg/L, about 2 mg/L, about 2.5 mg/L, about 3 mg/L, about 4 mg/L, or about 5 mg/L dextran sulfate. In some embodiments, the final dextran sulfate concentration is about 1 mg/L dextran sulfate. In some embodiments, the final dextran sulfate concentration is about 1.5 mg/L dextran sulfate. In some embodiments, the final dextran sulfate concentration is about 2 mg/L dextran sulfate. In some embodiments, the final dextran sulfate concentration is about 2.5 mg/L dextran sulfate. In some embodiments, the final dextran sulfate concentration is about 3 mg/L dextran sulfate. In some embodiments, the final dextran sulfate concentration is about 3.5 mg/L dextran sulfate. In some embodiments, the final dextran sulfate concentration is about 4 mg/L dextran sulfate.

In some embodiments, the final dextran sulfate concentration is about 2 mg/L dextran sulfate.

In some embodiments, the starting dextran sulfate concentration is between about 1 mg/L and about 10 mg/L, between about 1 mg/L and about 5 mg/L, between about 2 mg/L and about 10 mg/L, between about 3 mg/L and about 10 mg/L, or between about 3 mg/L and about 5 mg/L dextran sulfate, and the final dextran sulfate concentration is between about 0.5 mg/L and about 10 mg/L, between about 0.5 mg/L and about 5 mg/L, between about 0.5 mg/L and about 3 mg/L, between about 1 mg/L and about 10 mg/L, between about 1 mg/L and about 5 mg/L, between about 1 mg/L and about 4 mg/L, or between about 1 mg/L and about 3 mg/L dextran sulfate. In some embodiments, the starting dextran sulfate concentration is between about 3 mg/L and about 6 mg/L dextran sulfate, and the final dextran sulfate concentration is between about 1 mg/L and about 3 mg/L dextran sulfate.

In some embodiments, the starting dextran sulfate concentration is about 2 mg/L, about 3 mg/L, about 4 mg/L, about 5 mg/L, about 6 mg/L, about 7 mg/L, about 8 mg/L, about 9 mg/L, or about 10 mg/L dextran sulfate, and the final dextran sulfate concentration is about 0.5 mg/L, about 1 mg/L, about 1.5 mg/L, about 2 mg/L, about 2.5 mg/L, about 3 mg/L, about 4 mg/L, or about 5 mg/L dextran sulfate.

In some embodiments, the starting dextran sulfate concentration is about 4 mg/L dextran sulfate, and the final dextran sulfate concentration is about 2 mg/L dextran sulfate.

In some embodiments, the recombinant virus particle is a recombinant adeno-associated virus (rAAV) particle. In some embodiments, the recombinant virus particle is a recombinant adenovirus (e.g., a human adenovirus or a chimpanzee adenovirus) particle. In some embodiments, the recombinant virus particle is a recombinant lentivirus particle.

In some embodiments, the recombinant virus particle is an rAAV particle. In some embodiments, the rAAV particle comprises a capsid protein of the AAV1, AAV2, AAV3, AAV4, AAV5, AAV6, AAV7, AAV8, AAV9, AAV10, AAV11, AAV12, AAV13, AAV14, AAV15, AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 serotype. In some embodiments, the rAAV particle comprises a capsid protein of the AAV8, AAV9, AAV.rh10, AAV.rh20, AAV.rh39, AAV.Rh74, AAV.RHM4-1, or AAV.hu37 serotype. In some embodiments, the rAAV particles comprise a capsid protein of the AAV8 serotype. In some embodiments, the rAAV particles comprise a capsid protein of the AAV9 serotype.

In some embodiments, the recombinant virus particle comprises a transgene. Various viral transgene expression systems suitable for use in particular host cells are known to one of skill in the art. It is understood that any viral transgene expression systems can be used in accordance with a method disclosed herein. In some embodiments, the transgene comprises a regulatory element operatively connected to a polynucleotide encoding a polypeptide. In some embodiments, the regulatory element comprises one or more of an enhancer, promoter, and polyA region. In some embodiments, the regulatory element and polynucleotide encoding a polypeptide are heterologous.

In some embodiments, the transgene encodes an anti-VEGF Fab, iduronidase (IDUA), iduronate 2-sulfatase (IDS), low-density lipoprotein receptor (LDLR), tripeptidyl peptidase 1 (TPP1), or non-membrane associated splice variant of VEGF receptor 1 (sFlt-1). In some embodiments, the transgene encodes an gamma-sarcoglycan, Rab Escort Protein 1 (REP1/CHM), retinoid isomerohydrolase (RPE65), cyclic nucleotide gated channel alpha 3 (CNGA3), cyclic nucleotide gated channel beta 3 (CNGB3), aromatic L-amino acid decarboxylase (AADC), lysosome-associated membrane protein 2 isoform B (LAMP2B), Factor VIII, Factor IX, retinitis pigmentosa GTPase regulator (RPGR), retinoschisin (RS1), sarcoplasmic reticulum calcium ATPase (SERCA2a), aflibercept, battenin (CLN3), transmembrane ER protein (CLN6), glutamic acid decarboxylase (GAD), Glial cell line-derived neurotrophic factor (GDNF), aquaporin 1 (AQP1), dystrophin, minidystrophin, microdystrophin, myotubularin 1 (MTM1), follistatin (FST), glucose-6-phosphatase (G6Pase), apolipoprotein A2 (APOA2), uridine diphosphate glucuronosyl transferase 1A1 (UGT1A1), arylsulfatase B (ARSB), N-acetyl-alpha-glucosaminidase (NAGLU), alpha-glucosidase (GAA), alpha-galactosidase (GLA), beta-galactosidase (GLB1), lipoprotein lipase (LPL), alpha 1-antitrypsin (AAT), phosphodiesterase 6B (PDE6B), ornithine carbamoyltransferase 90TC), survival motor neuron (SMN1), survival motor neuron (SMN2), neurturin (NRTN), Neurotrophin-3 (NT-3/NTF3), porphobilinogen deaminase (PBGD), nerve growth factor (NGF), mitochondrially encoded NADH: ubiquinone oxidoreductase core subunit 4 (MT-ND4), protective protein cathepsin A (PPCA), dysferlin, MER proto-oncogene, tyrosine kinase (MERTK), cystic fibrosis transmembrane conductance regulator (CFTR), or tumor necrosis factor receptor (TNFR)-immunoglobulin (IgG1) Fc fusion. In some embodiments, the recombinant virus particle is an rAAV particle. In some embodiments, the rAAV particles comprise a capsid protein of the AAV8 serotype. In some embodiments, the rAAV particles comprise a capsid protein of the AAV9 serotype.

In some embodiments, the transgene encodes a heterologous viral polypeptide. In some embodiments, the viral polypeptide is a coronavirus polypeptide. In some embodiments, the coronavirus is SARS-COV1 or SARS-COV2. In some embodiments, the transgene encodes the spike protein of SARS-CoV1 or SARS-COV2 or an immunogenic fragment thereof. In some embodiments, the transgene encodes the spike protein of SARS-COV2 or an immunogenic fragment thereof. In some embodiments, the transgene encodes the receptor binding domain of the SARS-COV2 spike protein. In some embodiments, the recombinant virus particle is a rAAV particle. In some embodiments, the recombinant virus particle is a recombinant adenovirus particle. In some embodiments, the recombinant virus particle is a recombinant chimpanzee adenovirus particle.

Transfection based recombinant virus particle production systems are known to the skilled artisan. See, e.g., Reiser et al., Gene Ther 7 (11): 910-3 (2000); Dull et al., J Virol. 72 (11): 8463-8471 (1998); Hoffmann et al., PNAS 97 (11) 6108-6113 (2000); Milian et al., Vaccine 35 (26): 3423-3430 (2017), each of which is incorporated herein by reference in its entirety. A method disclosed herein can be used to produce a recombinant virus particle in a transfection based production system. In some embodiments, the recombinant viral particle is a recombinant Dengue virus, a recombinant Ebola virus, a recombinant human papillomavirus (HPV), a recombinant human immunodeficiency virus (HIV), a recombinant adeno-associated virus (AAV), a recombinant lentivirus, a recombinant influenza virus, a recombinant vesicular stomatitis virus (VSV), a recombinant poliovirus, a recombinant adenovirus, a recombinant retrovirus, a recombinant vaccinia, a recombinant reovirus, a recombinant measles, a recombinant Newcastle disease virus (NDV), a recombinant herpes zoster virus (HZV), a recombinant herpes simplex virus (HSV), or a recombinant baculovirus. In some embodiments, the recombinant viral particle is a recombinant adeno-associated virus (AAV), a recombinant lentivirus, or a recombinant influenza virus. In some embodiments, the recombinant viral particle is a recombinant lentivirus. In some embodiments, the recombinant viral particle is a recombinant influenza virus. In some embodiments, the recombinant viral particle is a recombinant baculovirus. In some embodiments, the recombinant viral particle is a recombinant adeno-associated virus (AAV). In some embodiments, the rAAV particles are AAV8 or AAV9 particles. In some embodiments, the rAAV particles have an AAV capsid protein of a serotype selected from the group consisting of AAV.rh8, AAV.rh10, AAV.rh20, AAV.rh39, AAV.Rh74, AAV.RHM4-1, AAV.hu37, AAV.PHB, and AAV.7m8. In some embodiments, the rAAV particles have an AAV capsid protein with high sequence homology to AAV8 or AAV9 such as, AAV.rh10, AAV.rh20, AAV.rh39, AAV.Rh74, AAV.RHM4-1, and AAV.hu37.

Any suitable transfection reagent known in the art for transfecting a cell can be used for the production of a recombinant virus particle (e.g., rAAV particle) according to a method disclosed herein. In some embodiments, the cell is a HEK293 cell, such as a HEK293 cell adapted for suspension culture. In some embodiments, a method disclosed herein comprises transfecting a cell using a chemical based transfection method. In some embodiments, a method disclosed herein comprises transfecting a cell using a cationic organic carrier. See, e.g., Gigante et al., Medchemcomm 10 (10): 1692-1718 (2019); Damen et al. Medchemcomm 9 (9): 1404-1425 (2018), each of which is incorporated herein by reference in its entirety. In some embodiments, the cationic organic carrier comprises a lipid, for example, DOTMA, DOTAP, helper lipids (Dope, cholesterol), and combinations thereof. In some embodiments, the cationic organic carrier comprises a multivalent cationic lipid, for example, DOSPA, DOGS, and mixtures thereof. In some embodiments, the cationic organic carrier comprises bipolar lipids, or bolaamphiphiles (bolas). In some embodiments, the cationic organic carrier comprises bioreducible and/or dimerizable lipids. In some embodiments, the cationic organic carrier comprises gemini surfactants. In some embodiments, the cationic organic carrier comprises Lipofectin™, Transfectam™, Lipofectamine™, Lipofectamine 2000™, or Lipofectamin PLUS 2000™. In some embodiments, the cationic organic carrier comprises a polymer, for example, poly (L-Lysine) (PLL), polyethylenimine (PEI), polysaccharides (chitosan, dextran, cyclodextrine (CD)), Poly [2-(dimethylamino)ethyl methacrylate] (PDMAEMA), and dendrimers (polyamidoamine (PAMAM), poly(propylene imine) (PPI)). In some embodiments, the cationic organic carrier comprises a peptide, for example, peptides rich in basic amino-acids (CWL18), cell penetrating peptides (CPPs) (Arg-rich peptides (octaarginine, TAT)), nuclear localization signals (NLS) (SV40) and targeting (RGD). In some embodiments, the cationic organic carrier comprises a polymers (e.g., PEI) combined with a cationic liposome. Paris et al., Molecules 25 (14): 3277 (2020), which is incorporated herein by reference in its entirety. In some embodiments, the transfection reagent comprises calcium phosphate, highly branched organic compounds (dendrimers), cationic polymers (e.g., DEAE dextran or polyethylenimine (PEI)), lipofection.

In some embodiments, the transfection reagent comprises poly (L-Lysine) (PLL), polyethylenimine (PEI), linear PEI, branched PEI, dextran, cyclodextrine (CD), Poly [2-(dimethylamino) ethyl methacrylate] (PDMAEMA), polyamidoamine (PAMAM), poly(propylene imine) (PPI)), or mixtures thereof. In some embodiments, the transfection reagent comprises polyethylenimine (PEI), linear PEI, branched PEI, or mixtures thereof. In some embodiments, the transfection reagent comprises polyethylenimine (PEI). In some embodiments, the transfection reagent comprises linear PEI. In some embodiments, the transfection reagent comprises branched PEI. In some embodiments, the transfection reagent comprises polyethylenimine (PEI) having a molecular weight between about 5 and about 25 kDa. In some embodiments, the transfection reagent comprises PEGylated polyethylenimine (PEI). In some embodiments, the transfection reagent comprises modified polyethylenimine (PEI) to which hydrophobic moieties such cholesterol, choline, alkyl groups and some amino acids were attached.

The composition comprising one or more polynucleotides and a transfection reagent can be prepared by any method known to one of skill in the art. In some embodiments, the composition is prepared by admixing one or more polynucleotides with at least one transfection reagent comprises diluting each of the transfection reagent and the one or more polynucleotides into a sterile liquid, for example, tissue culture media, and mixing the diluted transfection reagent and diluted one or more polynucleotides. In some embodiments, the tissue culture media used for diluting the transfection reagent and/or the one or more polynucleotides does not comprise dextran sulfate. One of skill understands that the dilution and mixing is conducted so as to produce a composition comprising the transfection reagent and polynucleotides at a desired ratio and concentration. In some embodiments, the dilution and mixing of the at least one transfection reagent and one or more polynucleotides produces a composition comprising the transfection reagent and the polynucleotide at a weight ratio between about 1:5 and 5:1. In some embodiments, the weight ratio of the transfection reagent and polynucleotide is between about 1:3 and 3:1. In some embodiments, the weight ratio of the transfection reagent and polynucleotide is between about 1:3 and 1:1. In some embodiments, the weight ratio of the transfection reagent and polynucleotide is between about 1:2 and 1:1.5. I In some embodiments, the weight ratio of the transfection reagent and polynucleotide is about 1:5, 1:4, 1:3, 1:2.5, 1:2, 1:1.75, 1:1.5, 1:1.25, 1:1, 1.25:1, 1.5:1, 1.75:1, 2:1, 2.5:1, 3:1, 4:1, or 5:1. In some embodiments, the weight ratio of the transfection reagent and polynucleotide is about 1:2. In some embodiments, the weight ratio of the transfection reagent and polynucleotide is about 1:1.75. In some embodiments, the weight ratio of the transfection reagent and polynucleotide is about 1:1.5. In some embodiments, the weight ratio of the transfection reagent and polynucleotide is about 1:1.25. In some embodiments, the weight ratio of the transfection reagent and polynucleotide is about 1:1. In some embodiments, the weight ratio of the transfection reagent and polynucleotide is about 1.25:1. In some embodiments, the weight ratio of the transfection reagent and polynucleotide is about 1.5:1. In some embodiments, the weight ratio of the transfection reagent and polynucleotide is about 1.75:1. In some embodiments, the weight ratio of the transfection reagent and polynucleotide is about 2:1. In some embodiments, the one or more polynucleotides comprise 3 plasmids. In some embodiments, the one or more polynucleotides comprise 2 plasmids. In some embodiments, the one or more polynucleotides comprise 1 plasmid. In some embodiments, the recombinant virus is a recombinant AAV and the one or more polynucleotides comprise a mixture of three polynucleotides: one encoding the cap and rep genes, one encoding adenovirus helper functions necessary for packaging (e.g., adenovirus E1a gene, E1b gene, E4 gene, E2a gene, and VA gene), and one encoding the rAAV genome to be packaged. In some embodiments, the rAAV particles are AAV8 or AAV9 particles. In some embodiments, the rAAV particles have an AAV capsid protein of a serotype selected from the group consisting of AAV.rh8, AAV.rh10, AAV.rh20, AAV.rh39, AAV.Rh74, AAV.RHM4-1, AAV.hu37, AAV.PHB, and AAV.7m8. In some embodiments, the rAAV particles have an AAV capsid protein with high sequence homology to AAV8 or AAV9 such as, AAV.rh10, AAV.rh20, AAV.rh39, AAV.Rh74, AAV.RHM4-1, and AAV.hu37. In some embodiments, the transfection reagent is PEI.

In some embodiments, the composition comprising the transfection reagent and one or more polynucleotides is incubated before adding to the culture to allow the formation of polynucleotide: transfection reagent complexes. In some embodiments, the incubation is at room temperature. In some embodiments, the incubation comprises shaking the composition, for example, on a shaker at between about 100 and about 200 rpm. In some embodiments, the incubation is for between about 5 minutes and about 20 minutes. In some embodiments, the incubation is for about 10 to about 15 minutes. In some embodiments, the incubation is for no longer than 15 minutes. In some embodiments, the incubation is for no longer than 10 minutes. In some embodiments, the incubation is for about 5 minutes, about 10 minutes, or about 15 minutes. In some embodiments, the incubation is for about 10 minutes. In some embodiments, the transfection reagent comprises PEI.

In some embodiments, the volume of the composition comprising one or more polynucleotides containing genes necessary for producing the recombinant virus particle and a transfection reagent added to the culture is between about 5% and about 20% of the volume of the culture. In some embodiments, the volume of the composition added is between about 7% and about 15% of the volume of the culture. In some embodiments, the volume of the composition added is about 10% of the volume of the culture. In some embodiments, the one or more polynucleotides contain genes necessary for producing of recombinant AAV particles. In some embodiments, the transfection reagent comprises PEI. In some embodiments, the culture comprises HEK293 cells, such as HEK293 cells adapted for suspension culture.

In some embodiments, the culture has a volume of between about 400 liters and about 20,000 liters. In some embodiments, the culture has a volume of between about 500 liters and about 20,000 liters. In some embodiments, the culture has a volume of between about 700 liters and about 20,000 liters. In some embodiments, the culture has a volume of between about 1,000 liters and about 20,000 liters. In some embodiments, the culture has a volume of between about 400 liters and about 10,000 liters. In some embodiments, the culture has a volume of between about 500 liters and about 10,000 liters. In some embodiments, the culture has a volume of between about 700 liters and about 10,000 liters. In some embodiments, the culture has a volume of between about 1,000 liters and about 10,000 liters. In some embodiments, the culture has a volume of between about 400 liters' and about 5,000 liters. In some embodiments, the culture has a volume of between about 500 liters and about 5,000 liters. In some embodiments, the culture has a volume of between about 700 liters and about 5,000 liters. In some embodiments, the culture has a volume of between about 1,000 liters and about 5,000 liters. In some embodiments, the culture comprises HEK293 cells, such as HEK293 cells adapted for suspension culture.

In some embodiments, the culture has a volume of between about 200 liters and about 5,000 liters. In some embodiments, the culture has a volume of between about 200 liters and about 2,000 liters. In some embodiments, the culture has a volume of between about 200 liters and about 1,000 liters. In some embodiments, the culture has a volume of between about 200 liters and about 500 liters. In some embodiments, the culture comprises HEK293 cells, such as HEK293 cells adapted for suspension culture.

In some embodiments, the culture has a volume of about 200 liters. In some embodiments, the culture has a volume of about 300 liters. In some embodiments, the culture has a volume of about 400 liters. In some embodiments, the culture has a volume of about 500 liters. In some embodiments, the culture has a volume of about 750 liters. In some embodiments, the culture has a volume of about 1,000 liters. In some embodiments, the culture has a volume of about 2,000 liters. In some embodiments, the culture has a volume of about 3,000 liters. In some embodiments, the culture has a volume of about 5,000 liters. In some embodiments, the culture comprises HEK293 cells, such as HEK293 cells adapted for suspension culture.

In some embodiments, the culture comprises between about 2×10E+6 and about 10E+7 viable cell/ml. In some embodiments, the culture comprises between about 3×10E+6 and about 8×10E+6 viable cell/ml. In some embodiments, the culture comprises about 3×10E+6 viable cell/ml. In some embodiments, the culture comprises about 4×10E+6 viable cell/ml. In some embodiments, the culture comprises about 5×10E+6 viable cell/ml. In some embodiments, the culture comprises about 6×10E+6 viable cell/ml. In some embodiments, the culture comprises about 7×10E+6 viable cell/ml. In some embodiments, the culture comprises about 8×10E+6 viable cell/ml. In some embodiments, the culture comprises HEK293 cells, such as HEK293 cells adapted for suspension culture.

In some embodiments, the cells comprise mammalian cells or insect cells. In some embodiments, the cells comprise mammalian cells. In some embodiments, the cells comprise HEK293 cells, HEK derived cells, CHO cells, CHO derived cells, HeLa cells, SF-9 cells, BHK cells, Vero cells, and/or PerC6 cells. In some embodiments, the cells comprise HEK293 cells.

In some embodiments, the culture is maintained for between about 2 days and about 10 days after adding the composition comprising one or more polynucleotides containing genes necessary for producing the recombinant virus particle and a transfection reagent. In some embodiments, the culture is maintained for between about 5 days and about 14 days or more after adding the composition. In some embodiments, the culture is maintained for between about 2 days and about 7 days after adding the composition. In some embodiments, the culture is maintained for between about 3 days and about 5 days after adding the composition. In some embodiments, the culture is maintained for about 2 days, about 3 days, about 4 days, about 5 days, about 6 days, or about 7 days after adding the composition. In some embodiments, the culture is maintained for about 5 days after adding the composition. In some embodiments, the cell culture is maintained for about 6 days after adding the composition. In some embodiments, the cell culture is maintained under conditions that allow production of the rAAV particles for continuous harvest. In some embodiments, the culture comprises HEK293 cells, such as HEK293 cells adapted for suspension culture.

In some embodiments, a method disclosed herein increases production of the recombinant viral particle (e.g., rAAV particles) relative to a reference method comprising transfecting the cells in a cell culture that does not comprise dextran sulfate. In some embodiments, a method disclosed herein produces at least about 1.1 times, 1.2 times, 1.3 times, 1.4 times, 1.5 times, 1.6 times, 1.7 times, 1.8 times, 1.9 times or 2 times as many viral particles than a reference method comprising transfecting cells in a cell culture that does not comprise dextran sulfate. In some embodiments, a method disclosed herein produces at least about 10%, 20%, 30%, 40%, 50%, 60%, 70%, 80%, 90% or 100% more viral particles than a reference method comprising transfecting cells in a cell culture that does not comprise dextran sulfate. In some embodiments, a method disclosed herein produces at least about 10%, 20%, 30%, 40%, 50%, 60%, 70%, 80%, 90% or 100% more viral particles than a reference method comprising transfecting cells in a cell culture that does not comprise dextran sulfate. In some embodiments, a method disclosed herein produces at least about 10% more viral particles than the reference method. In some embodiments, a method disclosed herein produces at least about 20% more viral particles than the reference method. In some embodiments, a method disclosed herein produces at least about 20% more viral particles than the reference method. In some embodiments, a method disclosed herein produces at least about 20% more viral particles than the reference method. In some embodiments, a method disclosed herein produces at least about 70% more viral particles than the reference method. In some embodiments, a method disclosed herein produces at least about 100% more viral particles than the reference method. In some embodiments, a method disclosed herein increases recombinant virus production by at least about 50%, at least about 75%, or at least about 100%. In some embodiments, a method disclosed herein increases recombinant virus production by at least about two-fold, at least about three-fold, or at least about five-fold. In some embodiments, a method disclosed herein increases rAAV production by at least about two-fold. In some embodiments, the increase in production is determined by comparing the recombinant virus (e.g., rAAV) titers in the production cultures. In some embodiments, recombinant virus (e.g., rAAV) titer is measured as genome copy (GC) per milliliter of the production culture. In some embodiments, the recombinant virus is rAAV. In some embodiments, the rAAV particles comprise a capsid protein from an AAV capsid serotype selected from AAV8 and AAV9. In some embodiments, the rAAV particles have an AAV capsid serotype of AAV8. In some embodiments, the rAAV particles have an AAV capsid serotype of AAV9. In some embodiments, the rAAV particles have a capsid serotype selected from the group consisting of AAV.rh8, AAV.rh10, AAV.rh20, AAV.rh39, AAV.Rh74, AAV.RHM4-1, AAV.hu37, AAV.PHB, and AAV.7m8. In some embodiments, the rAAV particles have a capsid protein with high sequence homology to AAV8 or AAV9 such as, AAV.rh10, AAV.rh20, AAV.rh39, AAV.Rh74, AAV.RHM4-1, and AAV.hu37.

In some embodiments, a method disclosed herein increases production of rAAV particles while maintaining or improving the quality attributes of the rAAV particles and compositions comprising thereof. In some embodiments, the quality of rAAV particles and compositions comprising thereof is assessed by determining the concentration of rAAV particles (e.g., GC/ml), the percentage of particles comprising a copy of the rAAV genome; the ratio of particles without a genome, infectivity of the rAAV particles, stability of rAAV particles, concentration of residual host cell proteins, or concentration of residual host cell nucleic acids (e.g., host cell genomic DNA, plasmid encoding rep and cap genes, plasmid encoding helper functions, plasmid encoding rAAV genome). In some embodiments, the quality of rAAV particles produced by a method disclosed herein or compositions comprising thereof is the same as that of rAAV particles or compositions produced by a reference method comprising a single step of admixing, incubating and transferring the same volume of polynucleotide: transfection reagent complexes. In some embodiments, the quality of rAAV particles produced by a method disclosed herein or compositions comprising thereof is better than the quality of rAAV particles or compositions produced by a reference method comprising a single step of admixing, incubating and transferring the same volume of polynucleotide: transfection reagent complexes.

In some embodiments, a method disclosed herein produces between about 1×10e+10 GC/ml and about 1×10e+13 GC/ml rAAV particles. In some embodiments, a method disclosed herein produces between about 1×10e+10 GC/ml and about 1×10e+11 GC/ml rAAV particles. In some embodiments, a method disclosed herein produces between about 5×10e+10 GC/ml and about 1×10e+12 GC/ml rAAV particles. In some embodiments, a method disclosed herein produces between about 5×10e+10 GC/ml and about 1×10e+13 GC/ml rAAV particles. In some embodiments, a method disclosed herein produces between about 1×10e+11 GC/ml and about 1×10e+13 GC/ml rAAV particles. In some embodiments, a method disclosed herein produces between about 5×10e+10 GC/ml and about 5×10e+12 GC/ml rAAV particles. In some embodiments, a method disclosed herein produces between about 1×10e+11 GC/ml and about 5×10e+12 GC/ml rAAV particles. In some embodiments, a method disclosed herein produces more than about 1×10e+11 GC/ml rAAV particles. In some embodiments, a method disclosed herein produces more than about 5×10e+11 GC/ml rAAV particles. In some embodiments, a method disclosed herein produces more than about 1×10e+12 GC/ml rAAV particles. In some embodiments, the rAAV particles comprise a capsid protein from an AAV capsid serotype selected from AAV8 and AAV9. In some embodiments, the rAAV particles have an AAV capsid serotype of AAV8. In some embodiments, the rAAV particles have an AAV capsid serotype of AAV9. In some embodiments, the rAAV particles comprise a capsid protein from an AAV capsid serotype selected from the group consisting of AAV.rh8, AAV.rh10, AAV.rh20, AAV.rh39, AAV.Rh74, AAV.RHM4-1, AAV.hu37, AAV.PHB, and AAV.7m8. In some embodiments, the rAAV particles comprise a capsid protein with high sequence homology to AAV8 or AAV9 such as, AAV.rh10, AAV.rh20, AAV.rh39, AAV.Rh74, AAV.RHM4-1, and AAV.hu37.

In some embodiments, a method disclosed herein produces at least about 5×10e+10 GC/ml rAAV particles. In some embodiments, a method disclosed herein produces at least about 1×10e+11 GC/ml rAAV particles. In some embodiments, a method disclosed herein produces at least about 5×10e+11 GC/ml rAAV particles. In some embodiments, a method disclosed herein produces at least about 1×10e+12 GC/ml rAAV particles. In some embodiments, a method disclosed herein produces at least about 5×10e+12 GC/ml rAAV particles. In some embodiments, a method disclosed herein produces at least about 1×10e+13 GC/ml rAAV particles. In some embodiments, a method disclosed herein produces at least about 5×10e+13 GC/ml rAAV particles. In some embodiments, the rAAV particles comprise a capsid protein from an AAV capsid serotype selected from AAV8 and AAV9. In some embodiments, the rAAV particles have an AAV capsid serotype of AAV8. In some embodiments, the rAAV particles have an AAV capsid serotype of AAV9. In some embodiments, the rAAV particles comprise a capsid protein from an AAV capsid serotype selected from the group consisting of AAV.rh8, AAV.rh10, AAV.rh20, AAV.rh39, AAV.Rh74, AAV.RHM4-1, AAV.hu37, AAV.PHB, and AAV.7m8. In some embodiments, the rAAV particles comprise a capsid protein with high sequence homology to AAV8 or AAV9 such as, AAV.rh10, AAV.rh20, AAV.rh39, AAV.Rh74, AAV.RHM4-1, and AAV.hu37.

Numerous cell culture based systems are known in the art for production of rAAV particles, any of which can be used to practice a method disclosed herein. rAAV production cultures for the production of rAAV virus particles require; (1) suitable host cells, including, for example, human-derived cell lines such as HeLa, A549, or HEK293 cells and their derivatives (HEK293T cells, HEK293F cells), or mammalian cell lines such as Vero, CHO cells or CHO-derived cells; (2) suitable helper virus function, provided by wild type or mutant adenovirus (such as temperature sensitive adenovirus), herpes virus, baculovirus, or a plasmid construct providing helper functions; (3) AAV rep and cap genes and gene products; (4) a transgene (such as a therapeutic transgene) flanked by AAV ITR sequences; and (5) suitable media and media components to support rAAV production.

A skilled artisan is aware of the numerous methods by which AAV rep and cap genes, AAV helper genes (e.g., adenovirus E1a gene, E1b gene, E4 gene, E2a gene, and VA gene), and rAAV genomes (comprising one or more genes of interest flanked by inverted terminal repeats (ITRs)) can be introduced into cells to produce or package rAAV. The phrase "adenovirus helper functions" refers to a number of viral helper genes expressed in a cell (as RNA or protein) such that the AAV grows efficiently in the cell. The skilled artisan understands that helper viruses, including adenovirus and herpes simplex virus (HSV), promote AAV replication and certain genes have been identified that provide the essential functions, e.g. the helper may induce changes to the cellular environment that facilitate such AAV gene expression and replication. In some embodiments of a method disclosed herein, AAV rep and cap genes, helper genes, and rAAV genomes are introduced into cells by transfection of one or more plasmid vectors encoding the AAV rep and cap genes, helper genes, and rAAV genome.

Molecular biology techniques to develop plasmid or viral vectors encoding the AAV rep and cap genes, helper genes, and/or rAAV genome are commonly known in the art. In some embodiments, AAV rep and cap genes are encoded by one plasmid vector. In some embodiments, AAV helper genes (e.g., adenovirus E1a gene, E1b gene, E4 gene, E2a gene, and VA gene) are encoded by one plasmid vector. In some embodiments, the E1a gene or E1b gene is stably expressed by the host cell, and the remaining AAV helper genes are introduced into the cell by transfection by one viral vector. In some embodiments, the E1a gene and E1b gene are stably expressed by the host cell, and the E4 gene, E2a gene, and VA gene are introduced into the cell by transfection by one plasmid vector. In some embodiments, one or more helper genes are stably expressed by the host cell, and one or more helper genes are introduced into the cell by transfection by one plasmid vector. In some embodiments, the helper genes are stably expressed by the host cell. In some embodiments, AAV rep and cap genes are encoded by one viral vector. In some embodiments, AAV helper genes (e.g., adenovirus E1a gene, E1b gene, E4 gene, E2a gene, and VA gene) are encoded by one viral vector. In some embodiments, the E1a gene or E1b gene is stably expressed by the host cell, and the remaining AAV helper genes are introduced into the cell by transfection by one viral vector. In some embodiments, the E1a gene and E1b gene are stably expressed by the host cell, and the E4 gene, E2a gene, and VA gene are introduced into the cell by transfection by one viral vector. In some embodiments, one or more helper genes are stably expressed by the host cell, and one or more helper genes are introduced into the cell by transfection by one viral vector. In some embodiments, the AAV rep and cap genes, the adenovirus helper functions necessary for packaging, and the rAAV genome to be packaged are introduced to the cells by transfection with one or more polynucleotides, e.g., vectors. In some embodiments, a method disclosed herein comprises transfecting the cells with a mixture of three polynucleotides: one encoding the cap and rep genes, one encoding adenovirus helper functions necessary for packaging (e.g., adenovirus E1a gene, E1b gene, E4 gene, E2a gene, and VA gene), and one encoding the rAAV genome to be packaged. In some embodiments, the AAV cap gene is an AAV8 or AAV9 cap gene. In some embodiments, the AAV cap gene is an AAV.rh8, AAV.rh10, AAV.rh20, AAV.rh39, AAV.Rh74, AAV.RHM4-1, AAV.hu37, AAV.PHB, or AAV.7m8 cap gene. In some embodiments, the AAV cap gene encodes a capsid protein with high sequence homology to AAV8 or AAV9 such as, AAV.rh10, AAV.rh20, AAV.rh39, AAV.Rh74, AAV.RHM4-1, and AAV.hu37. In some embodiments, the vector encoding the rAAV genome to be packaged comprises a gene of interest flanked by AAV ITRs. In some embodiments, the AAV ITRs are from AAV1, AAV2, rAAV3, AAV4, AAV5, AAV6, AAV7, AAV8, AAV9, AAV10, AAV11, AAV12, AAV13, AAV14, AAV15, AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 or other AAV serotype.

Any combination of vectors can be used to introduce AAV rep and cap genes, AAV helper genes, and rAAV genome to a cell in which rAAV particles are to be produced or packaged. In some embodiments of a method disclosed herein, a first plasmid vector encoding an rAAV genome comprising a gene of interest flanked by AAV inverted terminal repeats (ITRs), a second vector encoding AAV rep and cap genes, and a third vector encoding helper genes can be used. In some embodiments, a mixture of the three vectors is co-transfected into a cell.

In some embodiments, a combination of transfection and infection is used by using both plasmid vectors as well as viral vectors.

In some embodiments, one or more of rep and cap genes, and AAV helper genes are constitutively expressed by the cells and does not need to be transfected or transduced into the cells. In some embodiments, the cell constitutively expresses rep and/or cap genes. In some embodiments, the cell constitutively expresses one or more AAV helper genes.

In some embodiments, the cell constitutively expresses E1a. In some embodiments, the cell comprises a stable transgene encoding the rAAV genome.

In some embodiments, AAV rep, cap, and helper genes (e.g., E1a gene, E1b gene, E4 gene, E2a gene, or VA gene) can be of any AAV serotype. Similarly, AAV ITRs can also be of any AAV serotype. For example, in some embodiments, AAV ITRs are from AAV1, AAV2, rAAV3, AAV4, AAV5, AAV6, AAV7, AAV8, AAV9, AAV10, AAV11, AAV12, AAV13, AAV14, AAV15, AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 or other AAV serotypes (e.g., a hybrid serotype harboring sequences from more than one serotype). In some embodiments, AAV cap gene is from AAV9 or AAV8 cap gene. In some embodiments, an AAV cap gene is from AAV1, AAV2, rAAV3, AAV4, AAV5, AAV6, AAV7, AAV8, AAV9, AAV10, AAV11, AAV12, AAV13, AAV14, AAV15, AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 or other AAV serotypes (e.g., a hybrid serotype harboring sequences from more than one serotype). In some embodiments, AAV rep and cap genes for the production of a rAAV particle is from different serotypes. For example, the rep gene is from AAV2 whereas the cap gene is from AAV9.

Any suitable media known in the art can be used for the production of recombinant virus particles (e.g., rAAV particles) according to a method disclosed herein. These media include, without limitation, media produced by Hyclone Laboratories and JRH including Modified Eagle Medium (MEM), Dulbecco's Modified Eagle Medium (DMEM), and Sf-900 II SFM media as described in U.S. Pat. No. 6,723,551, which is incorporated herein by reference in its entirety. In some embodiments, the medium comprises Dynamis™ Medium, FreeStyle™ 293 Expression Medium, or Expi293™ Expression Medium from Invitrogen/ThermoFisher. In some embodiments, the medium comprises Dynamis™ Medium. In some embodiments, a method disclosed herein uses a cell culture comprising a serum-free medium, an animal-component free medium, or a chemically defined medium. In some embodiments, the medium is an animal-component free medium. In some embodiments, the medium comprises serum. In some embodiments, the medium comprises fetal bovine serum. In some embodiments, the medium is a glutamine-free medium. In some embodiments, the medium comprises glutamine. In some embodiments, the medium is supplemented with one or more of nutrients, salts, buffering agents, and additives (e.g., antifoam agent). In some embodiments, the medium is supplemented with glutamine. In some embodiments, the medium is supplemented with serum. In some embodiments, the medium is supplemented with fetal bovine serum. In some embodiments, the medium is supplemented with poloxamer, e.g., Kolliphor® P 188 Bio. In some embodiments, a medium is a base medium. In some embodiments, the medium is a feed medium.

Recombinant virus (e.g., rAAV) production cultures can routinely be grown under a variety of conditions (over a wide temperature range, for varying lengths of time, and the like) suitable to the particular host cell being utilized. As is known in the art, virus production cultures include suspension-adapted host cells such as HeLa cells, HEK293 cells, HEK293 derived cells (e.g., HEK293T cells, HEK293F cells), Vero cells, CHO cells, CHO-K1 cells, CHO derived cells, EB66 cells, BSC cells, HepG2 cells, LLC-MK cells, CV-1 cells, COS cells, MDBK cells, MDCK cells, CRFK cells, RAF cells, RK cells, TCMK-1 cells, LLCPK cells, PK15 cells, LLC-RK cells, MDOK cells, BHK cells, BHK-21 cells, NS-1 cells, MRC-5 cells, WI-38 cells, BHK cells, 3T3 cells, 293 cells, RK cells, Per.C6 cells, chicken embryo cells and SF-9 cells which can be cultured in a variety of ways including, for example, spinner flasks, stirred tank bioreactors, and disposable systems such as the Wave bag system. Numerous suspension cultures are known in the art for production of rAAV particles, including for example, the cultures disclosed in U.S. Pat. Nos. 6,995,006, 9,783,826, and in U.S. Pat. Appl. Pub. No. 20120122155, each of which is incorporated herein by reference in its entirety. In some embodiments, the recombinant virus is recombinant AAV.

Any cell or cell line that is known in the art to produce a recombinant virus particles (e.g., rAAV particles) can be used in any one of the methods disclosed herein. In some embodiments, a method of producing recombinant virus particles (e.g., rAAV particles) or increasing the production of recombinant virus particles (e.g., a rAAV particles) disclosed herein uses HeLa cells, HEK293 cells, HEK293 derived cells (e.g., HEK293T cells, HEK293F cells), Vero cells, CHO cells, CHO-K1 cells, CHO derived cells, EB66 cells, LLC-MK cells, MDCK cells, RAF cells, RK cells, TCMK-1 cells, PK15 cells, BHK cells, BHK-21 cells, NS-1 cells, BHK cells, 293 cells, RK cells, Per.C6 cells, chicken embryo cells or SF-9 cells. In some embodiments, a method disclosed herein uses mammalian cells. In some embodiments, a method disclosed herein uses insect cells, e.g., SF-9 cells. In some embodiments, a method disclosed herein uses cells adapted for growth in suspension culture. In some embodiments, a method disclosed herein uses HEK293 cells adapted for growth in suspension culture. In some embodiments, the recombinant virus particles are recombinant AAV particles.

In some embodiments, a cell culture disclosed herein is a suspension culture. In some embodiments, a large scale suspension cell culture disclosed herein comprises HEK293 cells adapted for growth in suspension culture. In some embodiments, a cell culture disclosed herein comprises a serum-free medium, an animal-component free medium, or a chemically defined medium. In some embodiments, a cell culture disclosed herein comprises a serum-free medium. In some embodiments, suspension-adapted cells are cultured in a shaker flask, a spinner flask, a cellbag, or a bioreactor.

In some embodiments, a cell culture disclosed herein comprises a serum-free medium, an animal-component free medium, or a chemically defined medium. In some embodiments, a cell culture disclosed herein comprises a serum-free medium.

In some embodiments, a large scale suspension culture cell culture disclosed herein comprises a high density cell culture. In some embodiments, the culture has a total cell density of between about 1×10E+06 cells/ml and about 30×10E+06 cells/ml. In some embodiments, more than about 50% of the cells are viable cells. In some embodiments, the cells are Hela cells, HEK293 cells, HEK293 derived cells (e.g., HEK293T cells, HEK293F cells), Vero cells, or SF-9 cells. In further embodiments, the cells are HEK293 cells.

Methods disclosed herein can be used in the production of rAAV particles comprising a capsid protein from any AAV capsid serotype. In some embodiments, the rAAV particles comprise a capsid protein from an AAV capsid serotype selected from AAV1, AAV2, rAAV3, AAV4, AAV5, AAV6, AAV7, AAV8, AAV9, AAV10, AAV11, AAV12, AAV13, AAV14, AAV15, AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In some embodiments, the rAAV particles comprise a capsid protein that is a derivative, modification, or pseudotype of AAV1, AAV2, rAAV3, AAV4, AAV5, AAV6, AAV7, AAV8, AAV9, AAV10, AAV11, AAV12, AAV13, AAV14, AAV15, AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 capsid protein.

In some embodiments, the rAAV particles comprise a capsid protein from an AAV capsid serotype selected from AAV8 and AAV9. In some embodiments, the rAAV particles have an AAV capsid serotype of AAV8. In some embodiments, the rAAV particles have an AAV capsid serotype of AAV9.

In some embodiments, the rAAV particles comprise a capsid protein from an AAV capsid serotype selected from the group consisting of AAV.rh8, AAV.rh10, AAV.rh20, AAV.rh39, AAV.Rh74, AAV.RHM4-1, AAV.hu37, AAV.PHB, and AAV.7m8. In some embodiments, the rAAV particles comprise a capsid protein with high sequence homology to AAV8 or AAV9 such as, AAV.rh10, AAV.rh20, AAV.rh39, AAV.Rh74, AAV.RHM4-1, and AAV.hu37.

In some embodiments, the rAAV particles comprise a capsid protein that is a derivative, modification, or pseudotype of AAV8 or AAV9 capsid protein. In some embodiments, the rAAV particles comprise a capsid protein that has an AAV8 capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of AAV8 capsid protein.

In some embodiments, the rAAV particles comprise a capsid protein that is a derivative, modification, or pseudotype of AAV9 capsid protein. In some embodiments, rAAV particles comprise a capsid protein that has an AAV9 capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of AAV9 capsid protein.

In some embodiments, the rAAV particles comprise a capsid protein that has at least 80% or more identity, e.g., 85%, 85%, 87%, 88%, 89%, 90%, 91%, 92%, 93%, 94%, 95%, 96%, 97%, 98%, 99%, 99.5%, etc., i.e. up to 100% identity, to the VP1, VP2 and/or VP3 sequence of AAV.rh8, AAV.rh10, AAV.rh20, AAV.rh39, AAV.Rh74, AAV.RHM4-1, AAV.hu37, AAV.PHB, or AAV.7m8 capsid protein. In some embodiments, the rAAV particles comprise a capsid protein that has at least 80% or more identity, e.g., 85%, 85%, 87%, 88%, 89%, 90%, 91%, 92%, 93%, 94%, 95%, 96%, 97%, 98%, 99%, 99.5%, etc., i.e. up to 100% identity, to the VP1, VP2 and/or VP3 sequence of an AAV capsid protein with high sequence homology to AAV8 or AAV9 such as, AAV.rh10, AAV.rh20, AAV.rh39, AAV.Rh74, AAV.RHM4-1, and AAV.hu37.

In additional embodiments, the rAAV particles comprise a mosaic capsid. In additional embodiments, the rAAV particles comprise a pseudotyped rAAV particle. In additional embodiments, the rAAV particles comprise a capsid containing a capsid protein chimera of two or more AAV capsid serotypes.

rAAV Particles

The provided methods are suitable for use in the production of any isolated recombinant AAV particles. As such, the rAAV can be of any serotype, modification, or derivative, known in the art, or any combination thereof (e.g., a population of rAAV particles that comprises two or more serotypes, e.g., comprising two or more of rAAV2, rAAV8, and rAAV9 particles) known in the art. In some embodiments, the rAAV particles are AAV1, AAV2, rAAV3, AAV4, AAV5, AAV6, AAV7,AAV8, AAV9, AAV10, AAV11, AAV12, AAV13, AAV14, AAV15, AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 or other rAAV particles, or combinations of two or more thereof.

In some embodiments, rAAV particles have a capsid protein from an AAV serotype selected from AAV1, AAV1, AAV2, rAAV3, AAV4, AAV5, AAV6, AAV7, AAV8, AAV9, AAV10, AAV11, AAV12, AAV13, AAV14, AAV15, AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 or a derivative, modification, or pseudotype thereof. In some embodiments, rAAV particles comprise a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to e.g., VP1, VP2 and/or VP3 sequence of an AAV capsid serotype selected from AAV1, AAV1, AAV2, AAV3, AAV4, AAV5, AAV6, AAV7, AAV8, AAV9, AAV10, AAV11, AAV12, AAV13, AAV14, AAV15, AAV16, AAV.rh8, AAV.rh10, AAV.rh20, AAV.rh39, AAV.Rh74, AAV.RHM4-1, AAV.hu37, AAV.Anc80, rAAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16.

In some embodiments, rAAV particles comprise a capsid protein from an AAV capsid serotype selected from AAV1, AAV1, AAV2, rAAV3, AAV4, AAV5, AAV6, AAV7, AAV8, AAV9, AAV10, AAV11, AAV12, AAV13, AAV14, AAV15, AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16, or a derivative, modification, or pseudotype thereof. In some embodiments, rAAV particles comprise a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to e.g., VP1, VP2 and/or VP3 sequence of an AAV capsid serotype selected from AAV1, AAV1, AAV2, AAV3, AAV4, AAV5, AAV6, AAV7, AAV8, AAV9, AAV10, AAV11, AAV12, AAV13, AAV14, AAV15, AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16.

In some embodiments, rAAV particles comprise the capsid of Anc80 or Anc80L65, as described in Zinn et al., 2015, Cell Rep. 12 (6): 1056-1068, which is incorporated by reference in its entirety. In certain embodiments, the rAAV particles comprise the capsid with one of the following amino acid insertions: LGETTRP or LALGETTRP, as described in U.S. Pat. Nos. 9,193,956; 9,458,517; and 9,587,282 and US patent application publication no. 2016/0376323, each of which is incorporated herein by reference in its entirety. In some embodiments, rAAV particles comprise the capsid of AAV.7m8, as described in U.S. Pat. Nos. 9,193,956; 9,458,517; and 9,587,282 and US patent application publication no. 2016/0376323, each of which is incorporated herein by reference in its entirety. In some embodiments, rAAV particles comprise any AAV capsid disclosed in U.S. Pat. No. 9,585,971, such as AAV.PHP.B. In some embodiments, rAAV particles comprise any AAV capsid disclosed in U.S. Pat. No. 9,840,719 and WO 2015/013313, such as AAV.Rh74 and RHM4-1, each of which is incorporated herein by reference in its entirety. In some embodiments, rAAV particles comprise any AAV capsid disclosed in WO 2014/172669, such as AAV rh.74, which is incorporated herein by reference in its entirety. In some embodiments, rAAV particles comprise the capsid of AAV2/5, as described in Georgiadis et al., 2016, Gene Therapy 23:857-862 and Georgiadis et al., 2018, Gene Therapy 25:450, each of which is incorporated by reference in its entirety. In some embodiments, rAAV particles comprise any AAV capsid disclosed in WO 2017/070491, such as AAV2tYF, which is incorporated herein by reference in its entirety. In some embodiments, rAAV particles comprise the capsids of AAVLK03 or AAV3B, as described in Puzzo et al., 2017, Sci. Transl. Med. 29 (9): 418, which is incorporated by reference in its entirety. In some embodiments, rAAV particles comprise any AAV capsid disclosed in U.S. Pat. Nos. 8,628,966; 8,927,514; 9,923,120 and WO 2016/049230, such as HSC1, HSC2, HSC3, HSC4, HSC5, HSC6, HSC7, HSC8, HSC9, HSC10, HSC11, HSC12, HSC13, HSC14, HSC15, or HSC16, each of which is incorporated by reference in its entirety.

In some embodiments, rAAV particles comprise an AAV capsid disclosed in any of the following patents and patent applications, each of which is incorporated herein by reference in its entirety: U.S. Pat. Nos. 7,282,199; 7,906,111; 8,524,446; 8,999,678; 8,628,966; 8,927,514; 8,734,809; 9,284,357; 9,409,953; 9,169,299; 9,193,956; 9,458,517; and 9,587,282; US patent application publication nos. 2015/0374803; 2015/0126588; 2017/0067908; 2013/0224836; 2016/0215024; 2017/0051257; and International Patent Application Nos. PCT/US2015/034799; PCT/EP2015/053335. In some embodiments, rAAV particles have a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of an AAV capsid disclosed in any of the following patents and patent applications, each of which is incorporated herein by reference in its entirety: U.S. Pat. Nos. 7,282,199; 7,906,111; 8,524,446; 8,999,678; 8,628,966; 8,927,514; 8,734,809; 9,284,357; 9,409,953; 9,169,299; 9,193,956; 9,458,517; and 9,587,282; US patent application publication nos. 2015/0374803; 2015/0126588; 2017/0067908; 2013/0224836; 2016/0215024; 2017/0051257; and International Patent Application Nos. PCT/US2015/034799; PCT/EP2015/053335.

In some embodiments, rAAV particles have a capsid protein disclosed in Intl. Appl. Publ. No. WO 2003/052051 (see, e.g., SEQ ID NO: 2), WO 2005/033321 (see, e.g., SEQ ID NOs: 123 and 88), WO 03/042397 (see, e.g., SEQ ID NOs: 2, 81, 85, and 97), WO 2006/068888 (see, e.g., SEQ ID NOs: 1 and 3-6), WO 2006/110689, (see, e.g., SEQ ID NOs: 5-38) WO2009/104964 (see, e.g., SEQ ID NOs: 1-5, 7, 9, 20, 22, 24 and 31), WO 2010/127097 (see, e.g., SEQ ID NOs: 5-38), and WO 2015/191508 (see, e.g., SEQ ID NOs: 80-294), and U.S. Appl. Publ. No. 20150023924 (see, e.g., SEQ ID NOs: 1, 5-10), the contents of each of which is herein incorporated by reference in its entirety. In some embodiments, rAAV particles have a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of an AAV capsid disclosed in Intl. Appl. Publ. No. WO 2003/052051 (see, e.g., SEQ ID NO: 2), WO 2005/033321 (see, e.g., SEQ ID NOs: 123 and 88), WO 03/042397 (see, e.g., SEQ ID NOs: 2, 81, 85, and 97), WO 2006/068888 (see, e.g., SEQ ID NOs: 1 and 3-6), WO 2006/110689 (see, e.g., SEQ ID NOs: 5-38) WO2009/104964 (see, e.g., SEQ ID NOs: 1-5, 7, 9, 20, 22, 24 and 31), WO 2010/127097 (see, e.g., SEQ ID NOs: 5-38), and WO 2015/191508 (see, e.g., SEQ ID NOs: 80-294), and U.S. Appl. Publ. No. 20150023924 (see, e.g., SEQ ID NOs: 1, 5-10).

Nucleic acid sequences of AAV based viral vectors and methods of making recombinant AAV and AAV capsids are taught, for example, in U.S. Pat. Nos. 7,282,199; 7,906,111; 8,524,446; 8,999,678; 8,628,966; 8,927,514; 8,734,809; 9,284,357; 9,409,953; 9,169,299; 9,193,956; 9,458,517; and 9,587,282; US patent application publication nos. 2015/0374803; 2015/0126588; 2017/0067908; 2013/0224836; 2016/0215024; 2017/0051257; International Patent Application Nos. PCT/US2015/034799; PCT/EP2015/053335; WO 2003/052051, WO 2005/033321, WO 03/042397, WO 2006/068888, WO 2006/110689, WO2009/104964, WO 2010/127097, and WO 2015/191508, and U.S. Appl. Publ. No. 20150023924.

The provided methods are suitable for use in the production of recombinant AAV encoding a transgene. In certain embodiments, the transgene is from Tables 1A-1C. In some embodiments, the rAAV genome comprises a vector comprising the following components: (1) AAV inverted terminal repeats that flank an expression cassette; (2) regulatory control elements, such as a) promoter/enhancers, b) a poly A signal, and c) optionally an intron; and (3) nucleic acid sequences coding for a transgene. In other embodiments for expressing an intact or substantially intact monoclonal antibody (mAb), the rAAV genome comprises a vector comprising the following components: (1) AAV inverted terminal repeats that flank an expression cassette; (2) regulatory control elements, such as a) promoter/enhancers, b) a poly A signal, and c) optionally an intron; and (3) nucleic acid sequences coding for the light chain Fab and heavy chain Fab of the antibody, or at least the heavy chain or light chain Fab, and optionally a heavy chain Fc region. In still other embodiments for expressing an intact or substantially intact mAb, the rAAV genome comprises a vector comprising the following components: (1) AAV inverted terminal repeats that flank an expression cassette; (2) regulatory control elements, such as a) promoter/enhancers, b) a poly A signal, and c) optionally an intron; and (3) nucleic acid sequences coding for the heavy chain Fab of an anti-VEGF (e.g., sevacizumab, ranibizumab, bevacizumab, and brolucizumab), anti-EpoR (e.g., LKA-651), anti-ALK1 (e.g., ascrinvacumab), anti-C5 (e.g., tesidolumab and eculizumab), anti-CD105 (e.g., carotuximab), anti-CC1Q (e.g., ANX-007), anti-TNFα (e.g., adalimumab, infliximab, and golimumab), anti-RGMa (e.g., elezanumab), anti-TTR (e.g., NI-301 and PRX-004), anti-CTGF (e.g., pamrevlumab), anti-IL6R (e.g., satralizumab and sarilumab), anti-ILAR (e.g., dupilumab), anti-IL17A (e.g., ixekizumab and secukinumab), anti-IL-5 (e.g., mepolizumab), anti-IL12/IL23 (e.g., ustekinumab), anti-CD19 (e.g., inebilizumab), anti-ITGF7 mAb (e.g., etrolizumab), anti-SOST mAb (e.g., romosozumab), anti-pKal mAb (e.g., lanadelumab), anti-ITGA4 (e.g., natalizumab), anti-ITGA4B7 (e.g., vedolizumab), anti-BLyS (e.g., belimumab), anti-PD-1 (e.g., nivolumab and pembrolizumab), anti-RANKL (e.g., densomab), anti-PCSK9 (e.g., alirocumab and evolocumab), anti-ANGPTL3 (e.g., evinacumab*), anti-OxPL (e.g., E06), anti-fD (e.g., lampalizumab), or anti-MMP9 (e.g., andecaliximab); optionally an Fc polypeptide of the same isotype as the native form of the therapeutic antibody, such as an IgG isotype amino acid sequence IgG1, IgG2 or IgG4 or modified Fc thereof; and the light chain of an anti-VEGF (e.g., sevacizumab, ranibizumab, bevacizumab, and brolucizumab), anti-EpoR (e.g., LKA-651), anti-ALK1 (e.g., ascrinvacumab), anti-C5 (e.g., tesidolumab and eculizumab), anti-CD105 or anti-ENG (e.g., carotuximab), anti-CC1Q (e.g., ANX-007), anti-TNFα (e.g., adalimumab, infliximab, and golimumab), anti-RGMa (e.g., elezanumab), anti-TTR (e.g., NI-301 and PRX-004), anti-CTGF (e.g., pamrevlumab), anti-IL6R (e.g., satralizumab and sarilumab), anti-IL4R (e.g., dupilumab), anti-IL17A (e.g., ixekizumab and secukinumab), anti-IL-5 (e.g., mepolizumab), anti-IL12/IL23 (e.g., ustekinumab), anti-CD19 (e.g., inebilizumab), anti-ITGF7 mAb (e.g., etrolizumab), anti-SOST mAb (e.g., romosozumab), anti-pKal mAb (e.g., lanadelumab), anti-ITGA4 (e.g., natalizumab), anti-ITGA4B7 (e.g., vedolizumab), anti-BLyS (e.g., belimumab), anti-PD-1 (e.g., nivolumab and pembrolizumab), anti-RANKL (e.g., densomab), anti-PCSK9 (e.g., alirocumab and evolocumab), anti-ANGPTL3 (e.g., evinacumab), anti-OxPL (e.g., E06), anti-fD (e.g., lampalizumab), or anti-MMP9 (e.g., andecaliximab); wherein the heavy chain (Fab and optionally Fc region) and the light chain are separated by a self-cleaving furin (F)/F2A or flexible linker, ensuring expression of equal amounts of the heavy and the light chain polypeptides.

TABLE 1A

| Disease | Transgene |
|---|---|
| MPS I | alpha-L-iduronidase (IDUA) |
| MPS II (Hunter Syndrome) | iduronate-2-sulfatase (IDS) |
| ceroid lipofuscinosis (Batten disease) | (CLN1, CLN2, CLN10, CLN13), a soluble lysosomal protein (CLN5), a protein in the secretory pathway (CLN11), two cytoplasmic proteins that also peripherally associate with membranes (CLN4, CLN14), and many transmembrane proteins with different subcellular locations (CLN3, CLN6, CLN7, CLN8, CLN12) |
| MPS IIIa (Sanfilippo type A Syndrome) | heparan sulfate sulfatase (also called N-sulfoglucosamine sulfohydrolase (SGSH)) |
| MPS IIIB (Sanfilippo type B Syndrome) | N-acetyl-alpha-D-glucosaminidase (NAGLU) |
| MPS VI (Maroteaux-Lamy Syndrome) | arylsulfatase B |
| Gaucher disease (type 1, II and III) | Glucocerebrosidase, GBA1 |
| Parkinson's Disease | Glucocerebrosidase; GBA1 |
| Parkinson's Disease | dopamine decarboxylase |
| Pompe | acid maltase; GAA |
| Metachromatic leukodystrophy | Aryl sulfatase A |
| MPS VII (Sly syndrome) | beta-glucuronidase |
| MPS VIII | glucosamine-6-sulfate sulfatase |
| MPS IX | Hyaluronidase |
| Niemann-Pick disease | Sphingomyelinase |
| Niemann-Pick disease without sphingomyelinase deficiency | a npc1 gene encoding a cholesterol metabolizing enzyme |
| Tay-Sachs disease | Alpha subunit of beta-hexosaminidase |
| Sandhoff disease | both alpha and beta subunit of beta-hexosaminidase |
| Fabry Disease | alpha-galactosidase |
| Fucosidosis | Fucosidase (FUCA1 gene) |
| Alpha-mannosidosis | alpha-mannosidase |
| Beta-mannosidosis | Beta-mannosidase |
| Wolman disease | cholesterol ester hydrolase |
| Parkinson's disease | Neurturin |
| Parkinson's disease | glial derived growth factor (GDGF) |
| Parkinson's disease | tyrosine hydroxylase |
| Parkinson's disease | glutamic acid decarboxylase. |

TABLE 1A-continued

| Disease | Transgene |
|---|---|
| Parkinson's disease | fibroblast growth factor-2 (FGF-2) |
| Parkinson's disease | brain derived growth factor (BDGF) |
| No disease listed (Galactosialidosis (Goldberg syndrome)) | neuraminidase deficiency with betagalactosidase deficiency |
| Spinal Muscular Atrophy (SMA) | SMN |
| Friedreich's ataxia | Frataxin |
| Amyotrophic lateral sclerosis (ALS) | SOD1 |
| Glycogen Storage Disease 1a | Glucose-6-phosphatase |
| XLMTM | MTM1 |
| Crigler Najjar | UGT1A1 |
| CPVT | CASQ2 |
| Rett syndrome | MECP2 |
| Achromatopsia | CNGB3, CNGA3, GNAT2, PDE6C |
| Choroidermia | CDM |
| Danon Disease | LAMP2 |
| Cystic Fibrosis | CFTR |
| Duchenne Muscular Dystrophy | Mini-Dystrophin or Microdystrophin Gene |
| Limb Girdle Muscular Dystrophy Type 2C\|Gamma-sarcoglycanopathy | human-alpha-sarcoglycan |
| Advanced Heart Failure | SERCA2a |
| Rheumatoid Arthritis | TNFR: Fc Fusion Gene |
| Leber Congenital Amaurosis | GAA |
| Limb Girdle Muscular Dystrophy Type 2C\|Gamma-sarcoglycanopathy | gamma-sarcoglycan |
| Retinitis Pigmentosa | hMERTK |
| Age-Related Macular Degeneration | sFLT01 |
| Becker Muscular Dystrophy and Sporadic Inclusion Body Myositis | huFollistatin344 |
| Parkinson's Disease | GDNF |
| Metachromatic Leukodystrophy (MLD) | cuARSA |
| Hepatitis C | anti-HCV shRNA |
| Limb Girdle Muscular Dystrophy Type 2D | hSGCA |
| Human Immunodeficiency Virus Infections; HIV Infections (HIV-1) | PG9DP |
| Acute Intermittant Porphyria | PBGD |
| Leber's Hereditary Optical Neuropathy | P1ND4v2 |
| Alpha-1 Antitrypsin Deficiency | alpha1AT |
| Pompe Disease | hGAA |
| X-linked Retinoschisis | RS1 |
| Choroideremia | hCHM |
| Giant Axonal Neuropathy | JeT-GAN |
| X-linked Retinoschisis | hRS1 |
| Squamous Cell Head and Neck Cancer; Radiation Induced Xerostomia | hAQP1 |
| Hemophilia B | Factor IX |
| Homozygous FH | hLDLR |
| Dysferlinopathies | dysferlin transgene (e.g. rAAVrh74.MHCK7.DYSF.DV) |
| Hemophilia B | AAV6 ZFP nuclease |
| MPS I | AAV6 ZFP nuclease |
| Rheumatoid Arthritis | NF-kB.IFN-β |
| Batten/CLN6 | CLN6 |
| Sanfilippo Disease Type A | hSGSH |
| Osteoarthritis | 5IL-1Ra |
| Achromatopsia | CNGA3 |
| Achromatopsia | CNGB3 |
| Ornithine Transcarbamylase (OTC) Deficiency | OTC |
| Hemophilia A | Factor VIII |
| Mucopolysaccharidosis II | ZFP nuclease |
| Hemophilia A | ZFP nuclease |
| Wet AMD | anti-VEGF |
| X-Linked Retinitis Pigmentosa | RPGR |
| Mucopolysaccharidosis Type VI | hARSB |
| Leber Hereditary Optic Neuropathy | ND4 |
| X-Linked Myotubular Myopathy | MTM1 |
| Crigler-Najjar Syndrome | UGT1A1 |
| Achromatopsia | CNGB3 |
| Retinitis Pigmentosa | hPDE6B |
| X-Linked Retinitis Pigmentosa | RPGR |
| Mucopolysaccharidosis Type 3 B | hNAGLU |
| Duchenne Muscular Dystrophy | GALGT2 |
| Arthritis, Rheumatoid; Arthritis, Psoriatic; Ankylosing Spondylitis | TNFR: Fc Fusion Gene |
| Idiopathic Parkinson's Disease | Neurturin |
| Alzheimer's Disease | NGF |
| Human Immunodeficiency Virus | tgAAC09 |

TABLE 1A-continued

| Disease | Transgene |
|---|---|
| Infections; HIV Infections (HIV-1) | |
| Familial Lipoprotein Lipase Deficiency | LPL |
| Idiopathic Parkinson's Disease | Neurturin |
| Alpha-1 Antitrypsin Deficiency | hAAT |
| Leber Congenital Amaurosis (LCA) 2 | hRPE65v2 |
| Batten Disease; Late Infantile Neuronal Lipofuscinosis | CLN2 |
| Parkinson's Disease | GAD |
| Sanfilippo Disease Type A/ Mucopolysaccharidosis Type IIIA | N-sulfoglucosamine sulfohydrolase (SGSH) gene |
| Congestive Heart Failure | SERC2a |
| Becker Muscular Dystrophy and Sporadic Inclusion Body Myositis | Follistatin (e.g. rAAV.CMV.huFollistatin344) |
| Parkinson's Disease | hAADC-2 |
| Choroideremia | REP1 |
| CEA Specific AAV-DC-CTL Treatment in Stage IV Gastric Cancer | CEA |
| Gastric Cancer | MUC1-peptide-DC-CTL |
| Leber's Hereditary Optical Neuropathy | scAAV2-P1ND4v2 |
| Aromatic Amino Acid Decarboxylase Deficiency | hAADC |
| Hemophilia B | Factor IX |
| Parkinson's Disease | AADC |
| Leber Hereditary Optic Neuropathy | Genetic: GS010\|Drug: Placebo |
| SMA—Spinal Muscular Atrophy\|Gene Therapy | SMN |
| Hemophilia A | B-Domain Deleted Factor VIII |
| MPS I | IDUA |
| MPS II | IDS |
| CLN3-Related Neuronal Ceroid-Lipofuscinosis (Batten) | CLN3 |
| Limb-Girdle Muscular Dystrophy, Type 2E | hSGCB |
| Alzheimer Disease | APOE2 |
| Retinitis Pigmentosa | hMERKTK |
| Retinitis Pigmentosa | RLBP1 |
| Wet AMD or diabetic retinopathy | Anti-VEGF antibody or Anti-VEGF trap (e.g. one or more extracellular domains of VEGFR-1 and/or VEGFR-2; e.g. aflibercept) |

TABLE 1B

| ANTIGENS | | ANTIBODIES (TRANSGENE) | INDICATIONS |
|---|---|---|---|
| Nervous System Targets | Amyloid beta (Aβ or Abeta) peptides derived from APP | Solanezumab GSK933776 | Alzheimer's Disease |
| | Sortilin | AL-001 | Frontotemporal dementia (FTD) |
| | Tau protein | ABBV-8E12 UCB-0107 NI-105 (BIIB076) | Alzheimer's, Progressive supranuclear palsy, frontotemporal demential, chronic traumatic encephalopathy, Pick's complex, primary age-related taupathy |
| | Semaphorin-4D (SEMA4D) | VX15/2503 | Huntington's disease, juvenile Huntington's disease |
| | alpha-synuclein | Prasinezumab NI-202 (BIIB054) MED-1341 | Parkinson's disease, synucleinopathies |
| | superoxide dismutase-1 (SOD-1) | NI-204 | ALS, Alzheimer's Disease |
| | CGRP Receptor | eptinezumab, fremanezumab galcanezumab | Migraines, Cluster headaches |

TABLE 1B-continued

| ANTIGENS | | ANTIBODIES (TRANSGENE) | INDICATIONS |
|---|---|---|---|
| Ocular Anti-Angiogenic Targets | VEGF | Sevacizumab | diabetic retinopathy (DR), myopic choroidal neovascularization (mCNV), age-related macular degeneration (AMD), macular edema |
| | VEGF | ranibizumab (LUCENTIS ®) bevacizumab (AVASTIN ®) brolucizumab | Wet AMD |
| | erythropoietin receptor | LKA-651 | retinal vein occlusion (RVO), wet AMD, macular edema |
| | Amyloid beta (Aβ or Abeta) peptides derived from APP | Solanezumab GSK933776 | Dry AMD |
| | activin receptor like kinase 1 (ALK1) | ascrinvacumab | neovascular age-related macular degeneration |
| | complement component 5 (C5) | tesidolumab | dry AMD, uveitis |
| | endoglin (END or CD105) | carotuximab | wet AMD and other retinal disorders caused by increased vascularization |
| | complement component 1Q (C1Q) | ANX-007 | glaucoma |
| TNF-alpha | | adalimumab (HUMIRA ®) infliximab (REMICADE ®) golimumab | uveitis |
| Repulsive guidance molecule-A | | elezanumab | multiple sclerosis |
| Transthyretin (TTR) | | NI-301 PRX-004 | amyloidosis |
| Connective tissue growth factor (CTGF) | | pamrevlumab | fibrotic diseases, e.g. diabetic nephropathy, liver fibrosis, idiopathic pulmonary fibrosis |
| Neuromyelitis optica (NMO)/ Uveitis targets | interleukin receptor 6 (IL6R) | Satralizumab sarilumab | NMO, DR, DME, uveitis |
| | CD19 | inebilizumab | NMO |
| Integrin beta 7 | | etrolizumab | ulcerative colitis, Crohn's disease |
| Sclerostin | | romosozumab (EVENITY ®) | Osteoporosis, abnormal bone loss or weakness |

TABLE 1C

| ANTIGENS | | ANTIBODIES (TRANSGENE) | INDICATIONS |
|---|---|---|---|
| Nervous System Targets | Amyloid beta (Aβ or Abeta) peptides | Aducanumab crenezumab gantenerumab | Alzheimer's Disease |
| | Tau protein | anti-TAU | Alzheimer's, Progressive supranuclear palsy, frontotemporal demential, chronic traumatic |

TABLE 1C-continued

| ANTIGENS | | ANTIBODIES (TRANSGENE) | INDICATIONS |
|---|---|---|---|
| | | | encephalopathy, Pick's complex, primary age-related taupathy |
| | CGRP Receptor | erenumab (AIMOVIG ™) | Migraine |
| Interleukins or interleukin receptors | IL-17A | ixekizumab (TALTZ ®) secukinumab (COSENTYX ®) | Plaque psoriasis, psoriatic arthritis, ankylosing sponylitis |
| | IL-5 | mepolizumab (NUCALA ®) | Asthma |
| | IL-12/IL-23 | ustekinumab (STELARA ®) | Psoriasis & Crohn's disease |
| | IL-4R | dupilumab | Atopic dermatitis |
| | | vedolizumab (ENTYVIO ®) | Ulcerative colitis & Crohn's disease |
| Integrin | | Natalizumab (anti-integrin alpha 4) | Multiple sclerosis & Crohn's disease |
| Cardiovascular Targets | PCSK9 | alirocumab (PRALUENT ®) evolucomab (REPATHA ®) | HeFH & HoFH |
| | ANGPTL3 | evinacumab | HoFH & severe forms of dyslipidema |
| | Proinflammatory/ proatherogenic phospholipids | E06-scFv | Cardiovascular diseases such as atherosclerosis |
| RANKL | | denosumab (XGEVA ® and PROLIA ®) | Osteoporosis, increasing bone mass in breast and prostate cancer patients, & preventing skeletal-related events due to bone metastasis |
| PD-1, or PD-L1 or PD-L2 | | nivolumab (OPDIVO ®) pembrolizumab (KEYTRUDA ®) | Metastatic melanoma, lymphoma, non-small cell lung carcinoma |
| BLyS (B-lymphocyte stimulator, also known as B-cell activating factor (BAFF)) | | belimumab (BENLYSTA ®) | Systemic lupus erythromatosis |
| Ocular Targets | Factor D | lampalizumab | Dry AMD |
| | MMP9 | andecaliximab | Dry AMD |
| TNF-alpha | | adalimumab (HUMIRA ®) and infliximab (REMICADE ®) | Rheumatoid arthritis, psoriatic arthritis, askylosing spondylitis, Crohn's disease, plaque psoriasis, ulcerative colitis |
| Plasma Protein targets | C5, C5a | eculizumab (SOLIRIS ®) | Paroxysmal nocturnal hemoglobinuria, atypical hemolytic uremic syndrome, complement-mediated thrombotic microangiopathy |
| | Plasma kallikrein | lanadelumab | Hereditary angioedema (HAE) |

In some embodiments, the rAAV particles are rAAV viral vectors encoding an anti-VEGF Fab. In specific embodiments, the rAAV particles are rAAV8-based viral vectors encoding an anti-VEGF Fab. In more specific embodiments, the rAAV particles are rAAV8-based viral vectors encoding ranibizumab. In some embodiments, the rAAV particles are rAAV viral vectors encoding iduronidase (IDUA). In specific embodiments, the rAAV particles are rAAV9-based viral vectors encoding IDUA. In some embodiments, the rAAV particles are rAAV viral vectors encoding iduronate 2-sulfatase (IDS). In specific embodiments, the rAAV particles are rAAV9-based viral vectors encoding IDS. In some embodiments, the rAAV particles are rAAV viral vectors encoding a low-density lipoprotein receptor (LDLR). In specific embodiments, the rAAV particles are rAAV8-based viral vectors encoding LDLR. In some embodiments, the rAAV particles are rAAV viral vectors encoding tripeptidyl peptidase 1 (TPP1) protein. In specific embodiments, the rAAV particles are rAAV9-based viral vectors encoding TPP1. In some embodiments, the rAAV particles are rAAV viral vectors encoding non-membrane associated splice variant of VEGF receptor 1 (sFlt-1). In some embodiments, the rAAV particles are rAAV viral vectors encoding gamma-sarcoglycan, Rab Escort Protein 1 (REP1/CHM), retinoid isomerohydrolase (RPE65), cyclic nucleotide gated channel alpha 3 (CNGA3), cyclic nucleotide gated channel beta 3 (CNGB3), aromatic L-amino acid decarboxylase (AADC), lysosome-associated membrane protein 2 isoform B (LAMP2B), Factor VIII, Factor IX, retinitis pigmentosa GTPase regulator (RPGR), retinoschisin (RS1), sarcoplasmic reticulum calcium ATPase (SERCA2a), aflibercept, battenin (CLN3), transmembrane ER protein (CLN6), glutamic acid decarboxylase (GAD), Glial cell line-derived neurotrophic factor (GDNF), aquaporin 1 (AQP1), dystrophin, microdystrophin, myotubularin 1 (MTM1), follistatin (FST), glucose-6-phosphatase (G6Pase), apolipoprotein A2 (APOA2), uridine diphosphate glucuronosyl transferase 1A1 (UGT1A1), arylsulfatase B (ARSB), N-acetyl-alpha-glucosaminidase (NAGLU), alpha-glucosidase (GAA), alpha-galactosidase (GLA), beta-galactosidase (GLB1), lipoprotein lipase (LPL), alpha 1-antitrypsin (AAT), phosphodiesterase 6B (PDE6B), ornithine carbamoyltransferase 90TC), survival motor neuron (SMN1), survival motor neuron (SMN2), neurturin (NRTN), Neurotrophin-3 (NT-3/NTF3), porphobilinogen deaminase (PBGD), nerve growth factor (NGF), mitochondrially encoded NADH: ubiquinone oxidoreductase core subunit 4 (MT-ND4), protective protein cathepsin A (PPCA), dysferlin, MER proto-oncogene, tyrosine kinase (MERTK), cystic fibrosis transmembrane conductance regulator (CFTR), or tumor necrosis factor receptor (TNFR)-immunoglobulin (IgG1) Fc fusion.

In additional embodiments, rAAV particles comprise a pseudotyped AAV capsid. In some embodiments, the pseudotyped AAV capsids are rAAV2/8 or rAAV2/9 pseudotyped AAV capsids. Methods for producing and using pseudotyped rAAV particles are known in the art (see, e.g., Duan et al., J. Virol., 75:7662-7671 (2001); Halbert et al., J. Virol., 74:1524-1532 (2000); Zolotukhin et al., Methods 28:158-167 (2002); and Auricchio et al., Hum. Molec. Genet. 10:3075-3081, (2001).

In additional embodiments, rAAV particles comprise a capsid containing a capsid protein chimeric of two or more AAV capsid serotypes. In some embodiments, the capsid protein is a chimeric of 2 or more AAV capsid proteins from AAV serotypes selected from AAV1, AAV1, AAV2, AAV3, AAV4, AAV5, AAV6, AAV7, AAV8, AAV9, AAV10, AAV11, AAV12, AAV13, AAV14, AAV15, AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16.

In certain embodiments, a single-stranded AAV (ssAAV) can be used. In certain embodiments, a self-complementary vector, e.g., scAAV, can be used (see, e.g., Wu, 2007, Human Gene Therapy, 18 (2): 171-82, McCarty et al, 2001, Gene Therapy, Vol. 8, Number 16, Pages 1248-1254; and U.S. Pat. Nos. 6,596,535; 7,125,717; and 7,456,683, each of which is incorporated herein by reference in its entirety).

In some embodiments, the rAAV particles comprise a capsid protein from an AAV capsid serotype selected from AAV8 or AAV9. In some embodiments, the rAAV particles have an AAV capsid serotype of AAV8. In some embodiments, the rAAV particles have an AAV capsid serotype of AAV9.

In some embodiments, the rAAV particles comprise a capsid protein that is a derivative, modification, or pseudotype of AAV8 or AAV9 capsid protein. In some embodiments, the rAAV particles comprise a capsid protein that has an AAV8 capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of AAV8 capsid protein.

In some embodiments, the rAAV particles comprise a capsid protein that is a derivative, modification, or pseudotype of AAV9 capsid protein. In some embodiments, the rAAV particles comprise a capsid protein that has an AAV9 capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of AAV9 capsid protein.

In additional embodiments, the rAAV particles comprise a mosaic capsid. Mosaic AAV particles are composed of a mixture of viral capsid proteins from different serotypes of AAV. In some embodiments, the rAAV particles comprise a mosaic capsid containing capsid proteins of a serotype selected from AAV1, AAV2, AAV3, AAV4, AAV5, AAV6, AAV7, AAV8, AAV9, AAV10, AAV11, AAV12, AAV13, AAV14, AAV15, AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In some embodiments, the rAAV particles comprise a mosaic capsid containing capsid proteins of a serotype selected from AAV1, AAV2, AAV5, AAV6, AAV7, AAV8, AAV9, AAV10, AAVrh.8, AAVrh.10, AAVhu.37, AAVrh.20, and AAVrh.74.

In additional embodiments, the rAAV particles comprise a pseudotyped rAAV particle. In some embodiments, the pseudotyped rAAV particle comprises (a) a nucleic acid vector comprising AAV ITRs and (b) a capsid comprised of capsid proteins derived from AAVx (e.g., AAV1, AAV2, AAV3, AAV4, AAV5, AAV6, AAV7, AAV8, AAV9, AAV10, AAV11, AAV12, AAV13, AAV14, AAV15, AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16). In additional embodiments, the rAAV particles comprise a pseudotyped rAAV particle comprised of a capsid protein of an AAV serotype selected from AAV1, AAV2, AAV5, AAV6, AAV7, AAV8, AAV9, AAV10, AAVrh.8, and AAVrh.10, AAVhu.37, AAVrh.20, and AAVrh.74. In additional embodiments, the rAAV particles comprise a pseudotyped rAAV particle containing AAV8 capsid protein. In additional embodiments, the rAAV particles comprise a pseudotyped rAAV particle is comprised of AAV9 capsid protein. In some embodiments, the pseudotyped rAAV8 or rAAV9 particles are rAAV2/8 or rAAV2/9 pseudotyped particles. Methods for producing and using pseudotyped rAAV particles are known in the art (see, e.g., Duan et al., J. Virol., 75:7662-7671 (2001); Halbert et al., J. Virol., 74:1524-1532 (2000); Zolotukhin et al., Methods 28:158-167 (2002); and Auricchio et al., Hum. Molec. Genet. 10:3075-3081, (2001).

In additional embodiments, the rAAV particles comprise a capsid containing a capsid protein chimeric of two or more AAV capsid serotypes. In some embodiments, the rAAV particles comprise an AAV capsid protein chimeric of AAV8 capsid protein and one or more AAV capsid proteins from an AAV serotype selected from AAV1, AAV2, AAV3, AAV4, AAV5, AAV6, AAV7, AAV8, AAV9, AAV10, AAV11, AAV12, AAV13, AAV14, AAV15, AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In some embodiments, the rAAV particles comprise an AAV capsid protein chimeric of AAV8 capsid protein and one or more AAV capsid proteins from an AAV serotype selected from AAV1, AAV2, AAV5, AAV6, AAV7, AAV9, AAV10, rAAVrh.10, AAVrh.8, AAVrh. 10, AAVhu.37, AAVrh.20, and AAVrh.74. In some embodiments, the rAAV particles comprise an AAV capsid protein chimeric of AAV9 capsid protein the capsid protein of one or more AAV capsid serotypes selected from AAV1, AAV2, AAV3, AAV4, AAV5, AAV6, AAV7, AAV8, AAV9, AAV10, AAV11, AAV12, AAV13, AAV14, AAV15, AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In some embodiments, the rAAV particles comprise an AAV capsid protein chimeric of AAV9 capsid protein the capsid protein of one or more AAV capsid serotypes selected from AAV1, AAV2, AAV3, AAV4, AAV5, AA6, AAV7, AAV8, AAV9, AAVrh.8, AAVrh.10, AAVhu.37, AAVrh.20, and AAVrh.74.

Methods for Isolating rAAV Particles

In some embodiments, the disclosure provides methods for producing a composition comprising isolated recombinant adeno-associated virus (rAAV) particles, comprising isolating rAAV particles from a feed comprising an impurity (for example, rAAV production culture). In some embodiments, a method for producing a formulation comprising isolated recombinant adeno-associated virus (rAAV) particles disclosed herein comprises (a) isolating rAAV particles from a feed comprising an impurity (for example, rAAV production culture), and (b) formulating the isolated rAAV particles to produce the formulation.

In some embodiments, the disclosure further provides methods for producing a pharmaceutical unit dosage of a formulation comprising isolated recombinant adeno-associated virus (rAAV) particles, comprising isolating rAAV particles from a feed comprising an impurity (for example, rAAV production culture), and formulating the isolated rAAV particles.

Isolated rAAV particles can be isolated using methods known in the art. In some embodiments, methods of isolating rAAV particles comprises downstream processing such as, for example, harvest of a cell culture, clarification of the harvested cell culture (e.g., by centrifugation or depth filtration), tangential flow filtration, affinity chromatography, anion exchange chromatography, cation exchange chromatography, size exclusion chromatography, hydrophobic interaction chromatography, hydroxylapatite chromatography, sterile filtration, or any combination(s) thereof. In some embodiments, downstream processing includes at least 2, at least 3, at least 4, at least 5 or at least 6 of: harvest of a cell culture, clarification of the harvested cell culture (e.g., by centrifugation or depth filtration), tangential flow filtration, affinity chromatography, anion exchange chromatography, cation exchange chromatography, size exclusion chromatography, hydrophobic interaction chromatography, hydroxylapatite chromatography, and sterile filtration. In some embodiments, downstream processing comprises harvest of a cell culture, clarification of the harvested cell culture (e.g., by depth filtration), sterile filtration, tangential flow filtration, affinity chromatography, and anion exchange chromatography." In some embodiments, downstream processing comprises clarification of a harvested cell culture, sterile filtration, tangential flow filtration, affinity chromatography, and anion exchange chromatography. In some embodiments, downstream processing comprises clarification of a harvested cell culture by depth filtration, sterile filtration, tangential flow filtration, affinity chromatography, and anion exchange chromatography. In some embodiments, clarification of the harvested cell culture comprises sterile filtration. In some embodiments, downstream processing does not include centrifugation. In some embodiments, the rAAV particles comprise a capsid protein of the AAV8 serotype. In some embodiments, the rAAV particles comprise a capsid protein of the AAV9 serotype.

In some embodiments, a method of isolating rAAV particles produced according to a method disclosed herein comprises harvest of a cell culture, clarification of the harvested cell culture (e.g., by depth filtration), a first sterile filtration, a first tangential flow filtration, affinity chromatography, anion exchange chromatography (e.g., monolith anion exchange chromatography or AEX chromatography using a quaternary amine ligand), a second tangential flow filtration, and a second sterile filtration. In some embodiments, a method of isolating rAAV particles disclosed herein comprises harvest of a cell culture, clarification of the harvested cell culture (e.g., by depth filtration), a first sterile filtration, affinity chromatography, anion exchange chromatography (e.g., monolith anion exchange chromatography or AEX chromatography using a quaternary amine ligand), a tangential flow filtration, and a second sterile filtration. In some embodiments, a method of isolating rAAV particles produced according to a method disclosed herein comprises clarification of a harvested cell culture, a first sterile filtration, a first tangential flow filtration, affinity chromatography, anion exchange chromatography (e.g., monolith anion exchange chromatography or AEX chromatography using a quaternary amine ligand), a second tangential flow filtration, and a second sterile filtration. In some embodiments, a method of isolating. rAAV particles disclosed herein comprises clarification of a harvested cell culture, a first sterile filtration, affinity chromatography, anion exchange chromatography (e.g., monolith anion exchange chromatography or AEX chromatography using a quaternary amine ligand), tangential flow filtration, and a second sterile filtration. In some embodiments, a method of isolating rAAV. particles produced according to a method disclosed herein comprises clarification of a harvested cell culture by depth filtration, a first sterile filtration, a first tangential flow filtration, affinity chromatography, anion exchange chromatography (e.g., monolith anion exchange chromatography or AEX chromatography using a quaternary amine ligand), a second tangential flow filtration, and a second sterile filtration. In some embodiments, a method of isolating rAAV particles disclosed herein comprises clarification of a harvested cell culture by depth filtration, a first sterile filtration, affinity chromatography, anion exchange chromatography (e.g., monolith anion exchange chromatography or AEX chromatography using a quaternary amine ligand), tangential flow filtration, and a second sterile filtration. In some embodiments, the method does not include centrifugation. In some embodiments, clarification of the harvested cell culture comprises sterile filtration. In some embodiments, the rAAV particles comprise a capsid protein of the AAV8 serotype. In some embodiments, the rAAV particles comprise a capsid protein of the AAV9 serotype.

Numerous methods are known in the art for production of rAAV particles, including transfection, stable cell line production, and infectious hybrid virus production systems which include adenovirus-AAV hybrids, herpesvirus-AAV hybrids and baculovirus-AAV hybrids. rAAV production cultures for the production of rAAV virus particles all require; (1) suitable host cells, including, for example, human-derived cell lines such as HeLa, A549, or HEK293 cells and their derivatives (HEK293T cells, HEK293F cells), mammalian cell lines such as Vero, or insect-derived cell lines such as SF-9 in the case of baculovirus production systems; (2) suitable helper virus function, provided by wild type or mutant adenovirus (such as temperature sensitive adenovirus), herpes virus, baculovirus, or a plasmid construct providing helper functions; (3) AAV rep and cap genes and gene products; (4) a transgene (such as a therapeutic transgene) flanked by AAV ITR sequences; and (5) suitable media and media components to support rAAV production. Suitable media known in the art may be used for the production of rAAV vectors. These media include, without limitation, media produced by Hyclone Laboratories and JRH including Modified Eagle Medium (MEM), Dulbecco's Modified Eagle Medium (DMEM), and Sf-900 II SFM media as described in U.S. Pat. No. 6,723,551, which is incorporated herein by reference in its entirety.

rAAV production cultures can routinely be grown under a variety of conditions (over a wide temperature range, for varying lengths of time, and the like) suitable to the particular host cell being utilized. As is known in the art, rAAV production cultures include attachment-dependent cultures which can be cultured in suitable attachment-dependent vessels such as, for example, roller bottles, hollow fiber filters, microcarriers, and packed-bed or fluidized-bed bioreactors. rAAV vector production cultures may also include suspension-adapted host cells such as HeLa cells, HEK293 cells, HEK293 derived cells (e.g., HEK293T cells, HEK293F cells), Vero cells, CHO cells, CHO-K1 cells, CHO derived cells, EB66 cells, BSC cells, HepG2 cells, LLC-MK cells, CV-1 cells, COS cells, MDBK cells, MDCK cells, CRFK cells, RAF cells, RK cells, TCMK-1 cells, LLCPK cells, PK15 cells, LLC-RK cells, MDOK cells, BHK cells, BHK-21 cells, NS-1 cells, MRC-5 cells, WI-38 cells, BHK cells, 3T3 cells, 293 cells, RK cells, Per.C6 cells, chicken embryo cells or SF-9 cells which can be cultured in a variety of ways including, for example, spinner flasks, stirred tank bioreactors, and disposable systems such as the Wave bag system. In some embodiments, the cells are HEK293 cells. In some embodiments, the cells are HEK293 cells adapted for growth in suspension culture. Numerous suspension cultures are known in the art for production of rAAV particles, including for example, the cultures disclosed in U.S. Pat. Nos. 6,995,006, 9,783,826, and in U.S. Pat. Appl. Pub. No. 20120122155, each of which is incorporated herein by reference in its entirety.

In some embodiments, the rAAV production culture comprises a high density cell culture. In some embodiments, the culture has a total cell density of between about 1x10E+06 cells/ml and about 30x10E+06 cells/ml. In some embodiments, more than about 50% of the cells are viable cells. In some embodiments, the cells are HeLa cells, HEK293 cells, HEK293 derived cells (e.g., HEK293T cells, HEK293F cells), Vero cells, or SF-9 cells. In further embodiments, the cells are HEK293 cells. In further embodiments, the cells are HEK293 cells adapted for growth in suspension culture.

In additional embodiments of the provided method the rAAV production culture comprises a suspension culture comprising rAAV particles. Numerous suspension cultures are known in the art for production of rAAV particles, including for example, the cultures disclosed in U.S. Pat. Nos. 6,995,006, 9,783,826, and in U.S. Pat. Appl. Pub. No. 20120122155, each of which is incorporated herein by reference in its entirety. In some embodiments, the suspension culture comprises a culture of mammalian cells or insect cells. In some embodiments, the suspension culture comprises a culture of HeLa cells, HEK293 cells, HEK293 derived cells (e.g., HEK293T cells, HEK293F cells), Vero cells, CHO cells, CHO-K1 cells, CHO derived cells, EB66 cells, BSC cells, HepG2 cells, LLC-MK cells, CV-1 cells, COS cells, MDBK cells, MDCK cells, CRFK cells, RAF cells, RK cells, TCMK-1 cells, LLCPK cells, PK15 cells, LLC-RK cells, MDOK cells, BHK cells, BHK-21 cells, NS-1 cells, MRC-5 cells, WI-38 cells, BHK cells, 3T3 cells, 293 cells, RK cells, Per.C6 cells, chicken embryo cells or SF-9 cells. In some embodiments, the suspension culture comprises a culture of HEK293 cells.

In some embodiments, methods for the production of rAAV particles encompasses providing a cell culture comprising a cell capable of producing rAAV; adding to the cell culture a histone deacetylase (HDAC) inhibitor to a final concentration between about 0.1 mM and about 20 mM; and maintaining the cell culture under conditions that allows production of the rAAV particles. In some embodiments, the HDAC inhibitor comprises a short-chain fatty acid or salt thereof. In some embodiments, the HDAC inhibitor comprises butyrate (e.g., sodium butyrate), valproate (e.g., sodium valproate), propionate (e.g., sodium propionate), or a combination thereof.

In some embodiments, rAAV particles are produced as disclosed in WO 2020/033842, which is incorporated herein by reference in its entirety.

Recombinant AAV particles can be harvested from rAAV production cultures by harvest of the production culture comprising host cells or by harvest of the spent media from the production culture, provided the cells are cultured under conditions known in the art to cause release of rAAV particles into the media from intact host cells. Recombinant AAV particles can also be harvested from rAAV production cultures by lysis of the host cells of the production culture. Suitable methods of lysing cells are also known in the art and include for example multiple freeze/thaw cycles, sonication, microfluidization, and treatment with chemicals, such as detergents and/or proteases.

At harvest, rAAV production cultures can contain one or more of the following: (1) host cell proteins; (2) host cell DNA; (3) plasmid DNA; (4) helper virus; (5) helper virus proteins; (6) helper virus DNA; and (7) media components including, for example, serum proteins, amino acids, transferrins and other low molecular weight proteins. rAAV production cultures can further contain product-related impurities, for example, inactive vector forms, empty viral capsids, aggregated viral particles or capsids, mis-folded viral capsids, degraded viral particle.

In some embodiments, the rAAV production culture harvest is clarified to remove host cell debris. In some embodiments, the production culture harvest is clarified by filtration through a series of depth filters. Clarification can also be achieved by a variety of other standard techniques known in the art, such as, centrifugation or filtration through any cellulose acetate filter of 0.2 mm or greater pore size known in the art. In some embodiments, clarification of the harvested cell culture comprises sterile filtration. In some embodiments, the production culture harvest is clarified by centrifugation. In some embodiments, clarification of the production culture harvest does not included centrifugation.

In some embodiments, harvested cell culture is clarified using filtration. In some embodiments, clarification of the harvested cell culture comprises depth filtration. In some embodiments, clarification of the harvested cell culture further comprises depth filtration and sterile filtration. In some embodiments, harvested cell culture is clarified using a filter train comprising one or more different filtration media. In some embodiments, the filter train comprises a depth filtration media. In some embodiments, the filter train comprises one or more depth filtration media. In some embodiments, the filter train comprises two depth filtration media. In some embodiments, the filter train comprises a sterile filtration media. In some embodiments, the filter train comprises 2 depth filtration media and a sterile filtration media. In some embodiments, the depth filter media is a porous depth filter. In some embodiments, the filter train comprises Clarisolve® 20 MS, Millistak+® COHC, and a sterilizing grade filter media. In some embodiments, the filter train comprises Clarisolve® 20 MS, Millistak+® COHC, and Sartopore® 2 XLG 0.2 μm. In some embodiments, the harvested cell culture is pretreated before contacting it with the depth filter. In some embodiments, the pretreating comprises adding a salt to the harvested cell culture. In some embodiments, the pretreating comprises adding a chemical flocculent to the harvested cell culture. In some embodiments, the harvested cell culture is not pretreated before contacting it with the depth filter.

In some embodiments, the production culture harvest is clarified by filtration are disclosed in WO 2019/212921, which is incorporated herein by reference in its entirety.

In some embodiments, the rAAV production culture harvest is treated with a nuclease (e.g., Benzonase®) or endonuclease (e.g., endonuclease from *Serratia marcescens*) to digest high molecular weight DNA present in the production culture. The nuclease or endonuclease digestion can routinely be performed under standard conditions known in the art. For example, nuclease digestion is performed at a final concentration of 1-2.5 units/ml of Benzonase® at a temperature ranging from ambient to 37° C. for a period of 30 minutes to several hours.

Sterile filtration encompasses filtration using a sterilizing grade filter media. In some embodiments, the sterilizing grade filter media is a 0.2 or 0.22 μm pore filter. In some embodiments, the sterilizing grade filter media comprises polyethersulfone (PES). In some embodiments, the sterilizing grade filter media comprises polyvinylidene fluoride (PVDF). In some embodiments, the sterilizing grade filter media has a hydrophilic heterogeneous double layer design. In some embodiments, the sterilizing grade filter media has a hydrophilic heterogeneous double layer design of a 0.8 μm pre-filter and 0.2 μm final filter membrane. In some embodiments, the sterilizing grade filter media has a hydrophilic heterogeneous double layer design of a 1.2 μm pre-filter and 0.2 μm final filter membrane. In some embodiments, the sterilizing grade filter media is a 0.2 or 0.22 μm pore filter. In further embodiments, the sterilizing grade filter media is a 0.2 μm pore filter. In some embodiments, the sterilizing grade filter media is a Sartopore® 2 XLG 0.2 μm, Durapore™ PVDF Membranes 0.45 μm, or Sartoguard® PES 1.2 μm+0.2 μm nominal pore size combination. In some embodiments, the sterilizing grade filter media is a Sartopore® 2 XLG 0.2 μm.

In some embodiments, the clarified feed is concentrated via tangential flow filtration ("TFF") before being applied to a chromatographic medium, for example, affinity chromatography medium. Large scale concentration of viruses using TFF ultrafiltration has been described by Paul et al., Human Gene Therapy 4:609-615 (1993). TFF concentration of the clarified feed enables a technically manageable volume of clarified feed to be subjected to chromatography and allows for more reasonable sizing of columns without the need for lengthy recirculation times. In some embodiments, the clarified feed is concentrated between at least two-fold and at least ten-fold. In some embodiments, the clarified feed is concentrated between at least ten-fold and at least twenty-fold. In some embodiments, the clarified feed is concentrated between at least twenty-fold and at least fifty-fold. In some embodiments, the clarified feed is concentrated about twenty-fold. One of ordinary skill in the art will also recognize that TFF can also be used to remove small molecule impurities (e.g., cell culture contaminants comprising media components, serum albumin, or other serum proteins) form the clarified feed via diafiltration. In some embodiments, the clarified feed is subjected to diafiltration to remove small molecule impurities. In some embodiments, the diafiltration comprises the use of between about 3 and about 10 diafiltration volume of buffer. In some embodiments, the diafiltration comprises the use of about 5 diafiltration volume of buffer. One of ordinary skill in the art will also recognize that TFF can also be used at any step in the purification process where it is desirable to exchange buffers before performing the next step in the purification process. In some embodiments, the methods for isolating rAAV from the clarified feed disclosed herein comprise the use of TFF to exchange buffers.

Affinity chromatography can be used to isolate rAAV particles from a composition. In some embodiments, affinity chromatography is used to isolate rAAV particles from the clarified feed. In some embodiments, affinity chromatography is used to isolate rAAV particles from the clarified feed that has been subjected to tangential flow filtration. Suitable affinity chromatography media are known in the art and include without limitation, AVB Sepharose™, POROS™ CaptureSelect™ AAVX affinity resin, POROS™ CaptureSelect™ AAV9 affinity resin, and POROS™ CaptureSelect™ AAV8 affinity resin. In some embodiments, the affinity chromatography media is POROS™ CaptureSelect™ AAV9 affinity resin. In some embodiments, the affinity chromatography media is POROS™ CaptureSelect™ AAV8 affinity resin. In some embodiments, the affinity chromatography media is POROS™ CaptureSelect™ AAVX affinity resin.

Anion exchange chromatography can be used to isolate rAAV particles from a composition. In some embodiments, anion exchange chromatography is used after affinity chromatography as a final concentration and polish step. Suitable anion exchange chromatography media are known in the art and include without limitation, UNOsphere™ Q (Biorad, Hercules, Calif.), and N-charged amino or imino resins such as e.g., POROS™ 50 PI, or any DEAE, TMAE, tertiary or quaternary amine, or PEI-based resins known in the art (U.S. Pat. No. 6,989,264; Brument et al., Mol. Therapy 6 (5): 678-686 (2002); Gao et al., Hum. Gene Therapy 11:2079-2091 (2000)). In some embodiments, the anion exchange chromatography media comprises a quaternary amine. In some embodiments, the anion exchange media is a monolith anion exchange chromatography resin. In some embodiments, the monolith anion exchange chromatography media comprises glycidylmethacrylate-ethylenedimethacrylate or styrene-divinylbenzene polymers. In some embodiments, the monolith anion exchange chromatography media is selected from the group consisting of CIMmultus™ QA-1 Advanced Composite Column (Quaternary amine), CIMmultus™ DEAE-1 Advanced Composite Column (Diethylamino), CIM® QA Disk (Quaternary amine), CIM® DEAE, and CIM® EDA Disk (Ethylene diamino). In some embodiments, the monolith anion exchange chromatography media is CIMmultus™ QA-1 Advanced Composite Column (Quaternary amine). In some embodiments, the monolith anion exchange chromatography media is CIM® QA Disk (Quaternary amine). In some embodiments, the anion exchange chromatography media is CIM QA (BIA Separations, Slovenia). In some embodiments, the anion exchange chromatography media is BIA CIM® QA-80 (Column volume is 80 mL). One of ordinary skill in the art can appreciate that wash buffers of suitable ionic strength can be identified such that the rAAV remains bound to the resin while impurities, including without limitation impurities which may be introduced by upstream purification steps are stripped away.

In some embodiments, anion exchange chromatography is performed according to a method disclosed in WO 2019/241535, which is incorporated herein by reference in its entirety.

In some embodiments, a method of isolating rAAV particles comprises determining the vector genome titer, capsid titer, and/or the ratio of full to empty capsids in a composition comprising the isolated rAAV particles. In some embodiments, the vector genome titer is determined by quantitative PCR (qPCR) or digital PCR (dPCR) or droplet digital PCR (ddPCR). In some embodiments, the capsid titer is determined by serotype-specific ELISA. In some embodiments, the ratio of full to empty capsids is determined by Analytical Ultracentrifugation (AUC) or Transmission Electron Microscopy (TEM).

In some embodiments, the vector genome titer, capsid titer, and/or the ratio of full to empty capsids is determined by spectrophotometry, for example, by measuring the absorbance of the composition at 260 nm; and measuring the absorbance of the composition at 280 nm. In some embodiments, the rAAV particles are not denatured prior to measuring the absorbance of the composition. In some embodiments, the rAAV particles are denatured prior to measuring the absorbance of the composition. In some embodiments, the absorbance of the composition at 260 nm and 280 nm is determined using a spectrophotometer. In some embodiments, the absorbance of the composition at 260 nm and 280 nm is determined using a HPLC. In some embodiments, the absorbance is peak absorbance. Several methods for measuring the absorbance of a composition at 260 nm and 280 nm are known in the art. Methods of determining vector genome titer and capsid titer of a composition comprising the isolated recombinant rAAV particles are disclosed in WO 2019/212922, which is incorporated herein by reference in its entirety.

In additional embodiments the disclosure provides compositions comprising isolated rAAV particles produced according to a method disclosed herein. In some embodiment, the composition is a pharmaceutical composition comprising a pharmaceutically acceptable carrier.

As used herein the term "pharmaceutically acceptable means a biologically acceptable formulation, gaseous, liquid or solid, or mixture thereof, which is suitable for one or more routes of administration, in vivo delivery or contact. A "pharmaceutically acceptable" composition is a material that is not biologically or otherwise undesirable, e.g., the material may be administered to a subject without causing substantial undesirable biological effects. Thus, such a pharmaceutical composition may be used, for example in administering rAAV isolated according to the disclosed methods to a subject. Such compositions include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions. Pharmaceutical compositions can be formulated to be compatible with a particular route of administration or delivery, as set forth herein or known to one of skill in the art. Thus, pharmaceutical compositions include carriers, diluents, or excipients suitable for administration by various routes. Pharmaceutical compositions and delivery systems appropriate for rAAV particles and methods and uses of the invention are known in the art (see, e.g., Remington: The Science and Practice of Pharmacy (2003) 20th ed., Mack Publishing Co., Easton, Pa.; Remington's Pharmaceutical Sciences (1990) 18th ed., Mack Publishing Co., Easton, Pa.; The Merck Index (1996) 12th ed., Merck Publishing Group, Whitehouse, N.J.; Pharmaceutical Principles of Solid Dosage Forms (1993), Technonic Publishing Co., Inc., Lancaster, Pa.; Ansel and Stoklosa, Pharmaceutical Calculations (2001) 11th ed., Lippincott Williams & Wilkins, Baltimore, Md.; and Poznansky et al., Drug Delivery Systems (1980), R. L. Juliano, ed., Oxford, N.Y., pp. 253-315).

In some embodiments, the composition is a pharmaceutical unit dose. A "unit dose" refers to a physically discrete unit suited as a unitary dosage for the subject to be treated; each unit containing a predetermined quantity optionally in association with a pharmaceutical carrier (excipient, diluent, vehicle or filling agent) which, when administered in one or more doses, is calculated to produce a desired effect (e.g., prophylactic or therapeutic effect). Unit dose forms may be within, for example, ampules and vials, which may include a liquid composition, or a composition in a freeze-dried or lyophilized state; a sterile liquid carrier, for example, can be added prior to administration or delivery in vivo. Individual unit dose forms can be included in multi-dose kits or containers. Recombinant vector (e.g., AAV) sequences, plasmids, vector genomes, and recombinant virus particles, and pharmaceutical compositions thereof can be packaged in single or multiple unit dose form for ease of administration and uniformity of dosage. In some embodiments, the composition comprises rAAV particles comprising an AAV. capsid protein from an AAV capsid serotype selected from AAV1, AAV2, AAV3, AAV4, AAV5, AAV6, AAV7, AAV8, AAV9, AAV10, AAV11, AAV12, AAV13, AAV14, AAV15, AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In some embodiments, the AAV capsid serotype is AAV8. In some embodiments, the AAV capsid serotype is AAV9.

Methods of Producing a Recombinant Polypeptide

In one aspect, the disclosure provides a method of producing a recombinant polypeptide, comprising (a) providing a cell culture comprising cells suitable for producing the recombinant polypeptide, wherein the culture comprises between about 0.1 mg/L and about 10 mg/L dextran sulfate; (b) transfecting the cells by adding to the culture of a) a composition comprising one or more polynucleotides encoding the polypeptide and a transfection reagent; and (c) maintaining the cell culture comprising the transfected cells under conditions that allow the production of the recombinant polypeptide.

In some embodiments, the culture of a) comprises between about 0.5 mg/L and about 10 mg/L, between about 0.5 mg/L and about 5 mg/L, between about 0.5 mg/L and about 3 mg/L, between about 1 mg/L and about 10 mg/L, between about 1 mg/L and about 5 mg/L, between about 1 mg/L and about 4 mg/L, or between about 1 mg/L and about 3 mg/L dextran sulfate. In some embodiments, the culture of a) comprises between about 0.5 mg/L and about 5 mg/L dextran sulfate. In some embodiments, the culture of a) comprises between about 1 mg/L and about 5 mg/L dextran sulfate. In some embodiments, the culture of a) comprises between about 1 mg/L and about 3 mg/L dextran sulfate.

In some embodiments, the culture of a) comprises about 0.5 mg/L, about 1 mg/L, about 1.5 mg/L, about 2 mg/L, about 2.5 mg/L, about 3 mg/L, about 4 mg/L, or about 5 mg/L dextran sulfate. In some embodiments, the culture of a) comprises about 1 mg/L dextran sulfate. In some embodiments, the culture of a) comprises about 1.5 mg/L dextran sulfate. In some embodiments, the culture of a) comprises about 2 mg/L dextran sulfate. In some embodiments, the culture of a) comprises about 2.5 mg/L dextran sulfate. In some embodiments, the culture of a) comprises about 3 mg/L dextran sulfate. In some embodiments, the culture of a) comprises about 3.5 mg/L dextran sulfate. In some embodiments, the culture of a) comprises about 4 mg/L dextran sulfate.

In some embodiments, the culture of a) comprises about 2 mg/L dextran sulfate.

In some embodiments, the disclosure provides a method of producing a recombinant polypeptide, comprising (a) culturing cells suitable for producing the recombinant polypeptide in a cell culture, wherein the culture comprises a starting dextran sulfate concentration of between about 1 mg/L and about 20 mg/L and a final dextran sulfate concentration of between about 0.1 mg/L and about 10 mg/L; (b) transfecting the cells by adding to the culture of a) a composition comprising one or more polynucleotides encoding the polypeptide and a transfection reagent; and (c) maintaining the cell culture comprising the transfected cells under conditions that allow the production of the recombinant polypeptide.

In some embodiments, the starting dextran sulfate concentration is between about 1 mg/L and about 10 mg/L, between about 1 mg/L and about 5 mg/L, between about 2 mg/L and about 10 mg/L, between about 3 mg/L and about 10 mg/L, or between about 3 mg/L and about 5 mg/L dextran sulfate. In some embodiments, the starting dextran sulfate concentration is between about 1 mg/L and about 10 mg/L dextran sulfate. In some embodiments, the starting dextran sulfate concentration is between about 2 mg/L and about 10 mg/L dextran sulfate. In some embodiments, the starting dextran sulfate concentration is between about 3 mg/L and about 6 mg/L dextran sulfate.

In some embodiments, the starting dextran sulfate concentration is about 2 mg/L, about 3 mg/L, about 4 mg/L, about 5 mg/L, about 6 mg/L, about 7 mg/L, about 8 mg/L, about 9 mg/L, or about 10 mg/L dextran sulfate. In some embodiments, the starting dextran sulfate concentration is about 2 mg/L dextran sulfate. In some embodiments, the starting dextran sulfate concentration is about 3 mg/L dextran sulfate. In some embodiments, the starting dextran sulfate concentration is about 4 mg/L dextran sulfate. In some embodiments, the starting dextran sulfate concentration is about 5 mg/L dextran sulfate. In some embodiments, the starting dextran sulfate concentration is about 6 mg/L dextran sulfate. In some embodiments, the starting dextran sulfate concentration is about 7 mg/L dextran sulfate. In some embodiments, the starting dextran sulfate concentration is about 8 mg/L dextran sulfate.

In some embodiments, the starting dextran sulfate concentration is about 4 mg/L dextran sulfate.

In some embodiments, the final dextran sulfate concentration is between about 0.5 mg/L and about 10 mg/L, between about 0.5 mg/L and about 5 mg/L, between about 0.5 mg/L and about 3 mg/L, between about 1 mg/L and about 10 mg/L, between about 1 mg/L and about 5 mg/L, between about 1 mg/L and about 4 mg/L, or between about 1 mg/L and about 3 mg/L dextran sulfate. In some embodiments, the final dextran sulfate concentration is between about 0.5 mg/L and about 5 mg/L dextran sulfate. In some embodiments, the final dextran sulfate concentration is between about 1 mg/L and about 5 mg/L dextran sulfate. In some embodiments, the final dextran sulfate concentration is between about 1 mg/L and about 3 mg/L dextran sulfate.

In some embodiments, the final dextran sulfate concentration is about 0.5 mg/L, about 1 mg/L, about 1.5 mg/L, about 2 mg/L, about 2.5 mg/L, about 3 mg/L, about 4 mg/L, or about 5 mg/L dextran sulfate. In some embodiments, the final dextran sulfate concentration is about 1 mg/L dextran sulfate. In some embodiments, the final dextran sulfate concentration is about 1.5 mg/L dextran sulfate. In some embodiments, the final dextran sulfate concentration is about 2 mg/L dextran sulfate. In some embodiments, the final dextran sulfate concentration is about 2.5 mg/L dextran sulfate. In some embodiments, the final dextran sulfate concentration is about 3 mg/L dextran sulfate. In some embodiments, the final dextran sulfate concentration is about 3.5 mg/L dextran sulfate. In some embodiments, the final dextran sulfate concentration is about 4 mg/L dextran sulfate.

In some embodiments, the final dextran sulfate concentration is about 2 mg/L dextran sulfate.

In some embodiments, the starting dextran sulfate concentration is between about 1 mg/L and about 10 mg/L, between about 1 mg/L and about 5 mg/L, between about 2 mg/L and about 10 mg/L, between about 3 mg/L and about 10 mg/L, or between about 3 mg/L and about 5 mg/L dextran sulfate, and the final dextran sulfate concentration is between about 0.5 mg/L and about 10 mg/L, between about 0.5 mg/L and about 5 mg/L, between about 0.5 mg/L and about 3 mg/L, between about 1 mg/L and about 10 mg/L, between about 1 mg/L and about 5 mg/L, between about 1 mg/L and about 4 mg/L, or between about 1 mg/L and about 3 mg/L dextran sulfate. In some embodiments, the starting dextran sulfate concentration is between about 3 mg/L and about 6 mg/L dextran sulfate, and the final dextran sulfate concentration is between about 1 mg/L and about 3 mg/L dextran sulfate.

In some embodiments, the starting dextran sulfate concentration is about 2 mg/L, about 3 mg/L, about 4 mg/L, about 5 mg/L, about 6 mg/L, about 7 mg/L, about 8 mg/L, about 9 mg/L, or about 10 mg/L dextran sulfate, and the final dextran sulfate concentration is about 0.5 mg/L, about 1 mg/L, about 1.5 mg/L, about 2 mg/L, about 2.5 mg/L, about 3 mg/L, about 4 mg/L, or about 5 mg/L dextran sulfate.

In some embodiments, the starting dextran sulfate concentration is about 4 mg/L dextran sulfate, and the final dextran sulfate concentration is about 2 mg/L dextran sulfate.

In some embodiments, the one or more polynucleotides comprise a transgene. In some embodiments, the transgene comprises a regulatory element operatively connected to a polynucleotide encoding a polypeptide.

In some embodiments, the polypeptide comprises an antibody or antigen-binding fragment thereof, bispecific antibody, enzyme, fusion protein or Fc fusion protein. In some embodiments, the polypeptide comprises an antibody or antigen-binding fragment thereof. In some embodiments, the polypeptide comprises a fusion protein, e.g., an Fc fusion protein. In some embodiments, the polypeptide comprises an enzyme.

The terms "antibody" as used herein encompasses whole antibodies and antibody fragments including any functional domain of an antibody such as an antigen-binding fragment or single chains thereof, an effector domain, salvage receptor binding epitope, or portion thereof. A typical antibody comprises at least two heavy (H) chains and two light (L) chains interconnected by disulfide bonds. Each heavy chain is comprised of a heavy chain variable region (VH) and a heavy chain constant region. In some embodiments, the heavy chain constant region comprises three domains, CH1, CH2, and CH3. Each light chain is comprised of a light chain variable region (VL) and a light chain constant region. In some embodiments, the light chain constant region comprises one domain, C1. The VH and VL regions can be further subdivided into regions of hypervariablity, termed Complementarity Determining Regions (CDRs), interspersed with regions that are more conserved, termed framework regions (FW). Each VH and VL is composed of three CDRs and four FWs, arranged from amino-terminus to carboxy-terminus in the following order: FW1, CDR1, FW2, CDR2, FW3, CDR3, FW4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. Non-limiting types of antibodies of the present disclosure include typical antibodies, scFvs, and combinations thereof.

The term "antibody fragment" refers to a portion of an intact antibody and refers to any functional domain of an antibody such as an antigen-binding fragment or single chains thereof, an effector domain or a portion thereof. Examples of antibody fragments include, but are not limited to, Fab, Fab', F(ab') 2, and Fv fragments, linear antibodies, single chain antibodies, and multi-specific antibodies formed from antibody fragments. "Antibody fragment" as used herein comprises an antigen-binding site or epitope binding site.

As used herein, the term, "Fc region" or simply "Fc" is understood to mean the carboxyl-terminal portion of an immunoglobulin chain constant region, preferably an immunoglobulin heavy chain constant region, or a portion thereof. For example, an immunoglobulin Fc region may comprise (1) a CH1 domain, a CH2 domain, and a CH3 domain, (2) a CH1 domain and a CH2 domain, (3) a CH1 domain and a CH3 domain, (4) a CH2 domain and a CH3 domain, or (5) a combination of two or more domains and an immunoglobulin hinge region. In some embodiments, Fc region comprises at least an immunoglobulin hinge region a CH2 domain and a CH3 domain, and preferably lacks the CH1 domain. In some embodiments, the class of immunoglobulin from which the heavy chain constant region is derived is IgG (Igγ) (γ subclasses 1, 2, 3, or 4). Other classes of immunoglobulin, IgA (Igα), IgD (Igδ), IgE (Igε) and IgM (Igu), can be used. The choice of particular immunoglobulin heavy chain constant region sequences from certain immunoglobulin classes and subclasses to achieve a particular result is considered to be within the level of skill in the art. In some embodiments, the portion of the DNA construct encoding the immunoglobulin Fc region preferably comprises at least a portion of a hinge domain, and preferably at least a portion of a CH3 domain of Fc gamma or the homologous domains in any of IgA, IgD, IgE, or IgM. Furthermore, it is contemplated that substitution or deletion of amino acids within the immunoglobulin heavy chain constant regions may be useful in the practice of the methods and compositions disclosed herein. One example would be to introduce amino acid substitutions in the upper CH2 region to create an Fc variant with reduced affinity for Fc receptors (Cole, J. Immunol. 159:3613 (1997)).

Various recombinant expression systems suitable for the production of recombinant polypeptides in particular host cells are known to one of skill in the art. It is understood that any recombinant expression system can be used for producing a recombinant polypeptide in accordance with a method disclosed herein.

Any suitable transfection reagent known in the art for transfecting a cell can be used for producing a recombinant polypeptide in accordance with a method disclosed herein. In some embodiments, the transfection reagent comprises a cationic organic carrier. See, e.g., Gigante et al., Medchemcomm 10 (10): 1692-1718 (2019); Damen et al. Medchemcomm 9 (9): 1404-1425 (2018), each of which is incorporated herein by reference in its entirety. In some embodiments, the cationic organic carrier comprises a lipid, for example, DOTMA, DOTAP, helper lipids (Dope, cholesterol), and combinations thereof. In some embodiments, the cationic organic carrier comprises a multivalent cationic lipid, for example, DOSPA, DOGS, and mixtures thereof. In some embodiments, the cationic organic carrier comprises bipolar lipids, or bolaamphiphiles (bolas). In some embodiments, the cationic organic carrier comprises bioreducible and/or dimerizable lipids. In some embodiments, the cationic organic carrier comprises gemini surfactants. In some embodiments, the cationic organic carrier comprises Lipofectin™, Transfectam™, Lipofectamine™, Lipofectamine 2000™, or Lipofectamin PLUS 2000™. In some embodiments, the cationic organic carrier comprises a polymer, for example, poly (L-Lysine) (PLL), polyethylenimine (PEI), polysaccharides (chitosan, dextran, cyclodextrine (CD)), Poly [2-(dimethylamino)ethyl methacrylate] (PDMAEMA), and dendrimers (polyamidoamine (PAMAM), poly(propylene imine) (PPI)). In some embodiments, the cationic organic carrier comprises a peptide, for example, peptides rich in basic amino-acids (CWL18), cell penetrating peptides (CPPs) (Arg-rich peptides (octaarginine, TAT)), nuclear localization signals (NLS) (SV40) and targeting (RGD). In some embodiments, the cationic organic carrier comprises a polymers (e.g., PEI) combined with a cationic liposome. Paris et al., Molecules 25 (14): 3277 (2020), which is incorporated herein by reference in its entirety. In some embodiments, the transfection reagent comprises calcium phosphate, highly branched organic compounds (dendrimers), cationic polymers (e.g., DEAE dextran or polyethylenimine (PEI)), lipofection.

In some embodiments, the transfection reagent comprises poly (L-Lysine) (PLL), polyethylenimine (PEI), linear PEI, branched PEI, dextran, cyclodextrine (CD), Poly [2-(dimethylamino) ethyl methacrylate] (PDMAEMA), polyamidoamine (PAMAM), poly(propylene imine) (PPI)), or mixtures thereof. In some embodiments, the transfection reagent comprises polyethylenimine (PEI), linear PEI, branched PEI, or mixtures thereof. In some embodiments, the transfection reagent comprises polyethylenimine (PEI). In some embodiments, the transfection reagent comprises linear PEI. In some embodiments, the transfection reagent comprises branched PEI. In some embodiments, the transfection reagent comprises polyethylenimine (PEI) having a molecular weight between about 5 and about 25 kDa. In some embodiments, the transfection reagent comprises PEGylated polyethylenimine (PEI). In some embodiments, the transfection reagent comprises modified polyethylenimine (PEI) to which hydrophobic moieties such cholesterol, choline, alkyl groups and some amino acids were attached.

Any cell culture system known in the art can be used for producing a recombinant polypeptide in accordance with a method disclosed herein. In some embodiments, the cell culture is a suspension cell culture. In some embodiments, the cell culture is an adherent cell culture. In some embodiments, the cell culture comprises adherent cells grown attached to microcarriers or macrocarriers in stirred bioreactors. In some embodiments, the cell culture is a perfusion culture. In some embodiments, the cell culture is an alternating tangential flow (ATF) supported high-density perfusion culture.

In some embodiments, the cells comprise mammalian cells or insect cells. In some embodiments, the cells comprise mammalian cells. In some embodiments, the cells comprise HEK293 cells, HEK derived cells, CHO cells, CHO derived cells, HeLa cells, SF-9 cells, BHK cells, Vero cells, and/or PerC6 cells. In some embodiments, the cells comprise HEK293 cells.

In some embodiments, the cells comprise suspension-adapted cells. In some embodiments, the cells comprise suspension-adapted HeLa cells, HEK293 cells, HEK293 derived cells (e.g., HEK293T cells, HEK293F cells), Vero cells, CHO cells, CHO-K1 cells, CHO derived cells, EB66 cells, BSC cells, HepG2 cells, LLC-MK cells, CV-1 cells, COS cells, MDBK cells, MDCK cells, CRFK cells, RAF cells, RK cells, TCMK-1 cells, LLCPK cells, PK15 cells, LLC-RK cells, MDOK cells, BHK cells, BHK-21 cells, NS-1 cells, MRC-5 cells, WI-38 cells, BHK cells, 3T3 cells, 293 cells, RK cells, Per.C6 cells, chicken embryo cells or SF-9 cells. In some embodiments, the cells comprise suspension-adapted HEK293 cells, HEK293 derived cells (e.g., HEK293T cells, HEK293F cells), CHO cells, CHO-K1 cells, or CHO derived cells. In some embodiments, the cells comprise suspension-adapted HEK293 cells. In some embodiments, the cells comprise suspension-adapted CHO cells.

In some embodiments, the cell culture has a volume of between about 50 liters and about 20,000 liters. In some embodiments, the cell culture has a volume between about 50 liters and about 5,000 liters. In some embodiments, the cell culture has a volume between about 50 liters and about 2,000 liters. In some embodiments, the cell culture has a volume between about 50 liters and about 1,000 liters. In some embodiments, the cell culture has a volume between about 50 liters and about 500 liters.

Without being bound by any particular theory, methods disclosed herein increase the efficiency of transfection such that cells transfected according to a method disclosed herein produce more recombinant polypeptide than control cells transfected in a cell culture not comprising dextran sulfate.

In some embodiments, a method disclosed herein produces at least about a 10%, at least about a 20%, at least about a 30%, at least about a 40%, or at least about a 50% more recombinant polypeptide than a control method using a cell culture that does not comprise dextran sulfate. Methods of measuring recombinant polypeptide production are well known in the art. In some embodiments, recombinant polypeptide production is measured using Western blotting, ELIS assay or a functional assay (e.g., an assay to measure the catalytic activity of the recombinantly expressed polypeptide).

In some embodiments, a method of producing a recombinant polypeptide disclosed herein further comprises isolating the polypeptide. Various methods for isolating a recombinantly expressed polypeptide are known to one of skill in the art. It is understood that any of the known methods for isolating a recombinantly expressed polypeptide can be used in accordance with a method disclosed herein. In some embodiments, methods of isolating a recombinantly expressed polypeptide comprises harvest of a cell culture, clarification of the harvested cell culture (e.g., by centrifugation or depth filtration), tangential flow filtration, affinity chromatography, anion exchange chromatography, cation exchange chromatography, size exclusion chromatography, hydrophobic interaction chromatography, hydroxylapatite chromatography, sterile filtration, or any combination(s) thereof. In some embodiments, downstream processing includes at least 2, at least 3, at least 4, at least 5 or at least 6 of: harvest of a cell culture, clarification of the harvested cell culture (e.g., by centrifugation or depth filtration), tangential flow filtration, affinity chromatography, anion exchange chromatography, cation exchange chromatography, size exclusion chromatography, hydrophobic interaction chromatography, hydroxylapatite chromatography, and sterile filtration.

EXAMPLES

Example 1—Dextran Sulfate Surprisingly Increases AAV Production in a Transient Transfection Based System The present inventors surprisingly found that dextran sulfate is capable of increasing AAV titers in a transient transfection based production method. Alternating tangential flow (ATF) supported high-density perfusion culture technology was tested to produce seed cells for large scale transient transfection-based AAV production cultures. Recombinant AAV production was 5-fold reduced when suspension-adapted HEK cells from high-density perfusion reactors were used to seed production cultures. A potential reason for the drop in titer was the increased clumping of seed cells produced in a high-density perfusion culture, which could result in a variability in seeding densities and growth rates and inaccurate transfection reagent concentrations. While cell culture additives, such as dextran sulfate, were known to reduce clumping, their use was not considered a viable option in the production of cells for transient transfection because these agents are known to interfere with transient transfection. For example, Geng et al. (2007) at page 55 concludes that dextran sulfate completely inhibits PEI mediated transfection. Similarly, a recently published "Guide for DNA Transfection in iCELLis® 500 and iCELLis 500+ Bioreactors for Large Scale Gene Therapy Vector Manufacturing" by PALL® Biotech teaches at page 9 that dextran sulfate inhibits PEI mediated transfection.

Figure 2:
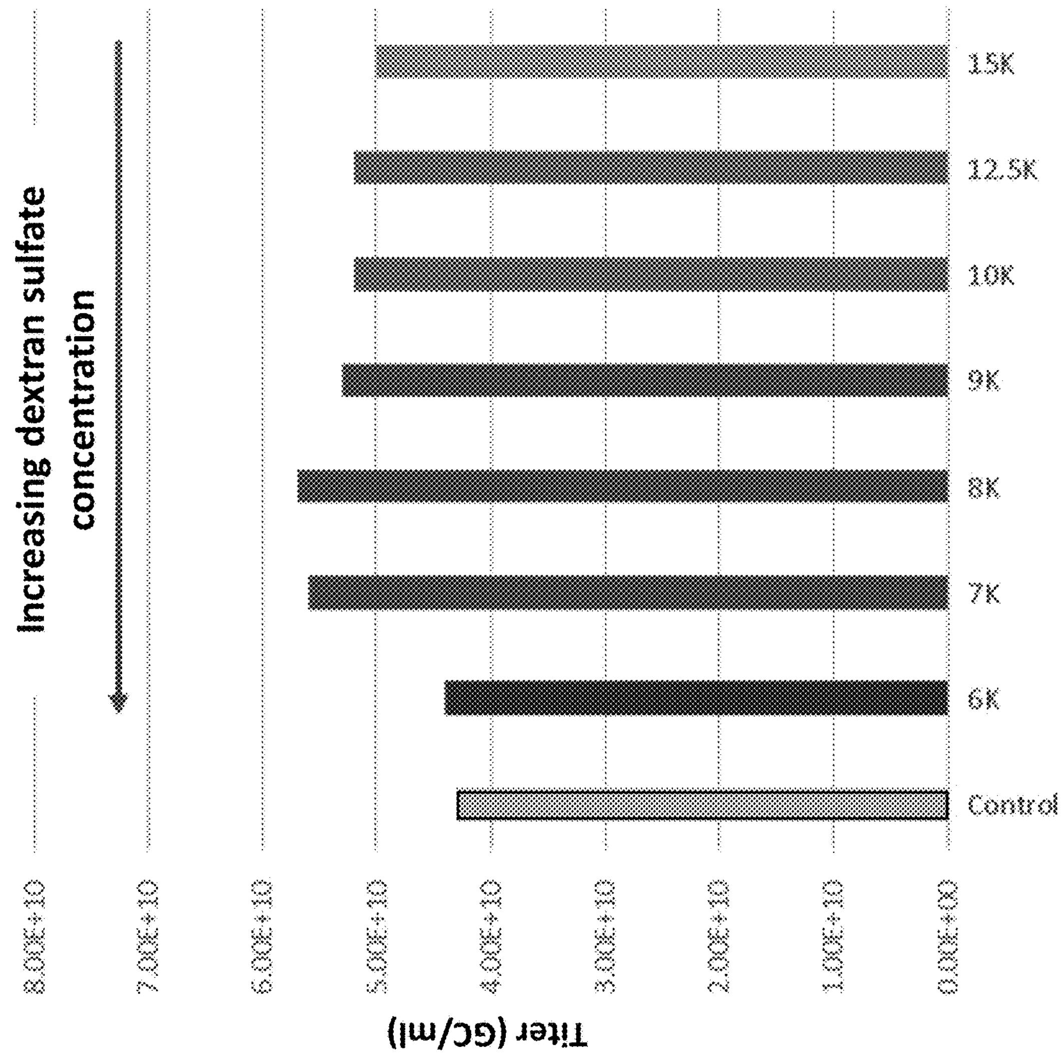
FIG. 2. Initial shake flask screen of dextran sulfate for use prior to and during transfection. 6K, 7K, 8K, 9K, 10K, 12K and 15K indicate the dilution factor of 25 g/L dextran sulfate stock solution present at the time of transfection and correspond to a concentration of 4.2 mg/L, 3.6 mg/L, 3.1 mg/L, 2.8 mg/L, 2.5 mg/L, 2.1 mg/L and 1.7 mg/L respectively.

In spite of the teachings that dextran sulfate inhibits transfection, the present inventors tested the effect of dextran sulfate on AAV titer in a transient transfection-based AAV production system. Recombinant AAV was produced via transient transfection of HEK293 cells. Briefly, HEK293 cells were expanded for 48 hrs in 250 ml shake flasks in medium comprising 0.3 to 10 mg/L dextran sulfate. The cells were transfected with a mixture of polyethylenimine (PEI) and 3 plasmids encoding adeno-virus helper functions, transgene and AAV Cap/Rep. Transfected cultures were maintained for 5 days following transfection to allow AAV production. AAV titer in the culture supernatants was determined using PCR based methods. Titers obtained using a recombinant AAV8 comprising transgene 1 and transgene 2 are shown in FIGS. 1 and 2, respectively. Surprisingly, the presence of dextran sulfate at a concentration between 0.652 mg/L and 2.5 mg/L (FIG. 1) and between 1.7 mg/L and 3.6 mg/L resulted in increased AAV titer. This finding was unexpected given the clear teachings of the prior art that dextran sulfate inhibits transient transfection, which is in accord with the finding that dextran sulfate at 10 mg/L or higher (FIG. 1) inhibited AAV production. Dextran sulfate had no significant effect on AAV titer when used at 0.313 mg/L (FIG. 1).

Figure 3:
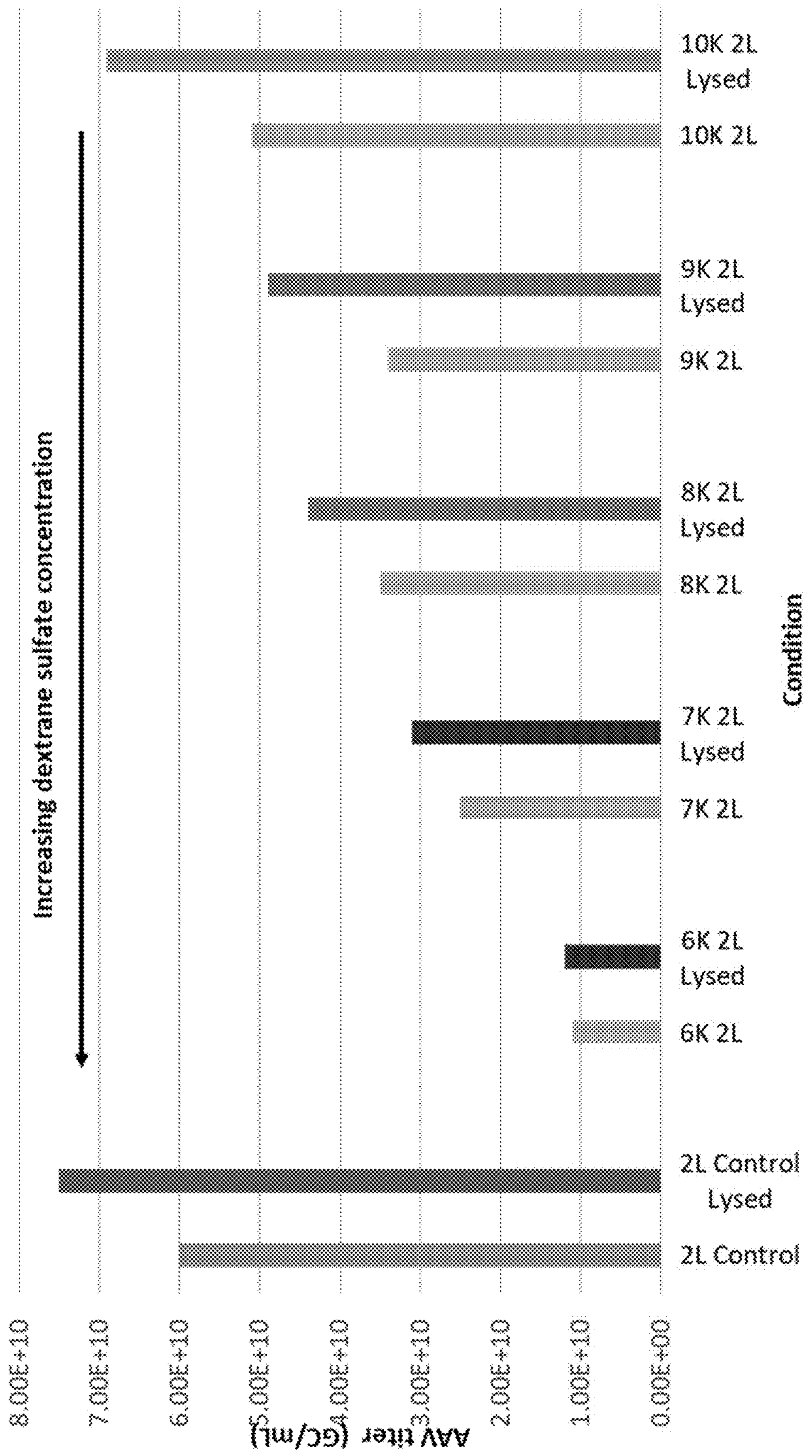
FIG. 3. Bench scale 2 L dextran sulfate titration for transfection: genome titer. 6K, 7K, 8K, 9K and 10K indicate the dilution factor of 25 g/L dextran sulfate stock solution present at the time of transfection and correspond to a concentration of 4.2 mg/L, 3.6 mg/L, 3.1 mg/L, 2.8 mg/L, and 2.5 mg/L, respectively.
Figure 4:
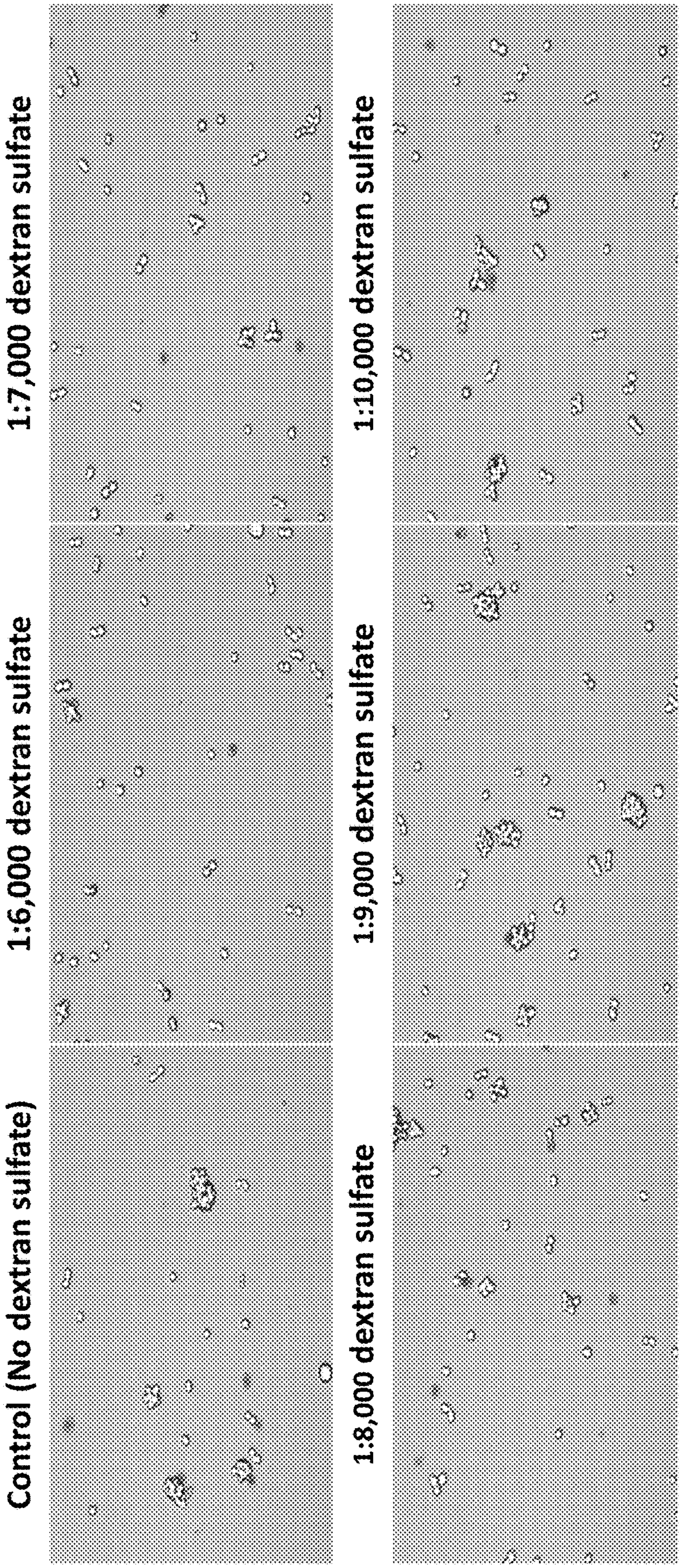
FIG. 4. Bench scale 2 L dextran sulfate titration for transfection: cell imaging. 1:6,000, 1:7,000, 1:8,000, 1:9,000 and 1:10,000 indicate the dilution factor of 25 g/L dextran sulfate stock solution present at the time of transfection and correspond to a concentration of 4.2 mg/L, 3.6 mg/L, 3.1 mg/L, 2.8 mg/L, and 2.5 mg/L, respectively.
Figure 5:
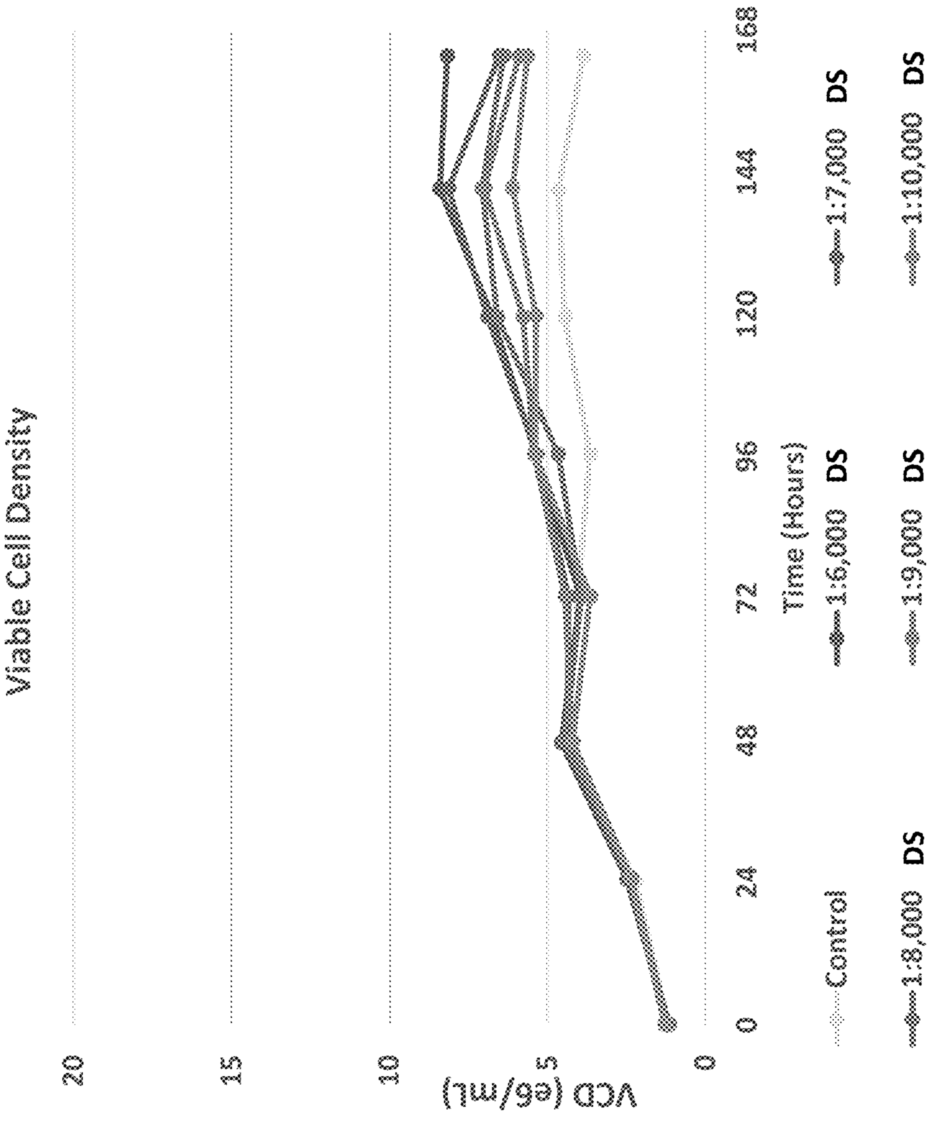
FIG. 5. Bench scale 2 L dextran sulfate titration for transfection: viable cell density. 1:6,000, 1:7,000, 1:8,000, 1:9,000 and 1:10,000 indicate the dilution factor of 25 g/L dextran sulfate stock solution present at the time of transfection and correspond to a concentration of 4.2 mg/L, 3.6 mg/L, 3.1 mg/L, 2.8 mg/L, and 2.5 mg/L, respectively.
Figure 6:
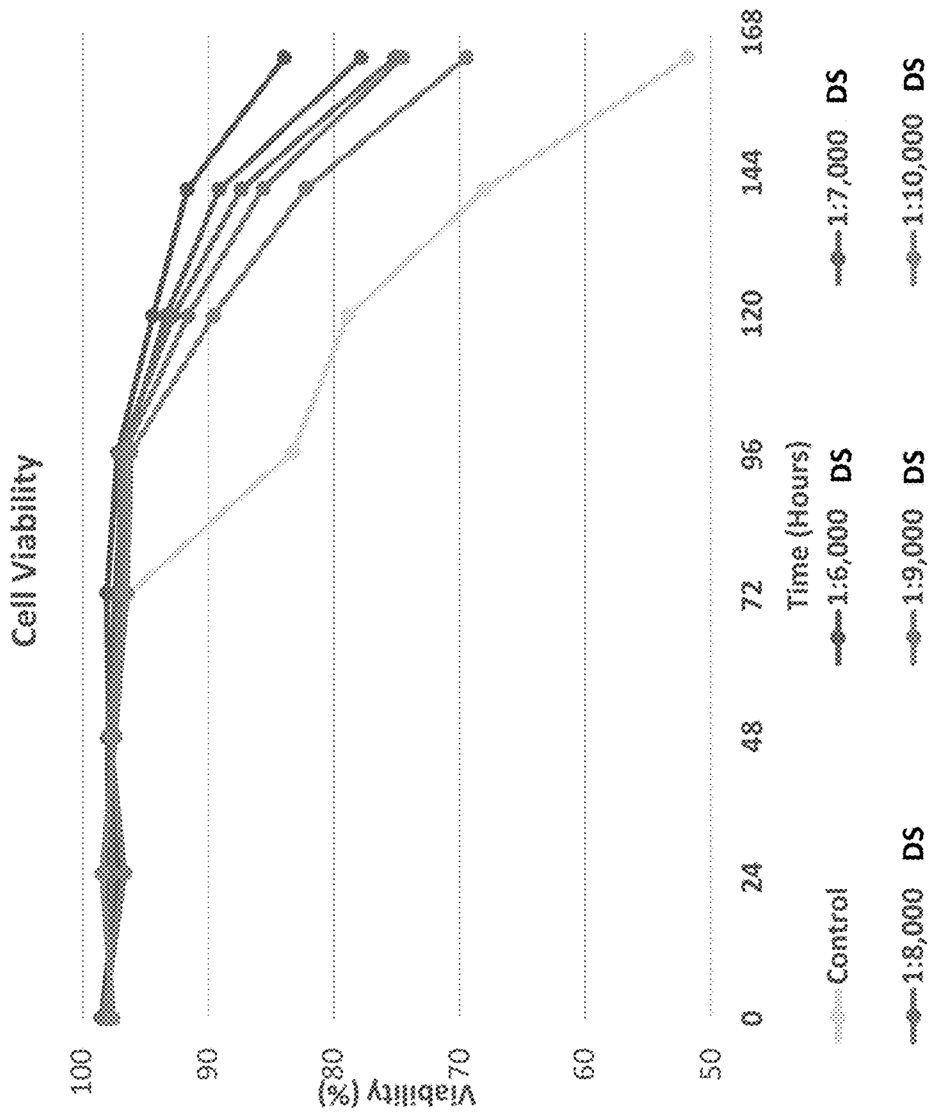
FIG. 6. Bench scale 2 L dextran sulfate titration for transfection: cell viability. 1:6,000, 1:7,000, 1:8,000, 1:9,000 and 1:10,000 indicate the dilution factor of 25 g/L dextran sulfate stock solution present at the time of transfection and correspond to a concentration of 4.2 mg/L, 3.6 mg/L, 3.1 mg/L, 2.8 mg/L, and 2.5 mg/L, respectively.

Example 2—Effect of Dextran Sulfate on AAV Titer in Bench Scale 2 L Reactors The effect of dextran sulfate on transfection based AAV production in bench scale reactors was studied. Recombinant AAV8 comprising transgene 2 was produced via transient transfection of HEK293 cells. Briefly, HEK293 cells were expanded for 3 days in 2 L reactors in medium comprising dextran sulfate at various concentrations. The cells were transfected with a mixture of polyethylenimine (PEI) and 3 plasmids encoding adeno-virus helper functions, transgene and AAV Cap/Rep. Transfected cultures were maintained for 4 days following transfection to allow AAV production. AAV particles were recovered either from the culture supernatant, or from the culture following lysis of the cells. FIG. 3. Viable cell density and cell viability was determined daily. FIGS. 5 and 6. Cell morphology was assessed at day 4 (FIG. 4). Dextran sulfate concentration ranges from 2.5 to 4.2 mg/L were not inhibitory to transfection in 2 L reactors and were beneficial to cell morphology including increased viability and viable cell density.

Figure 7:
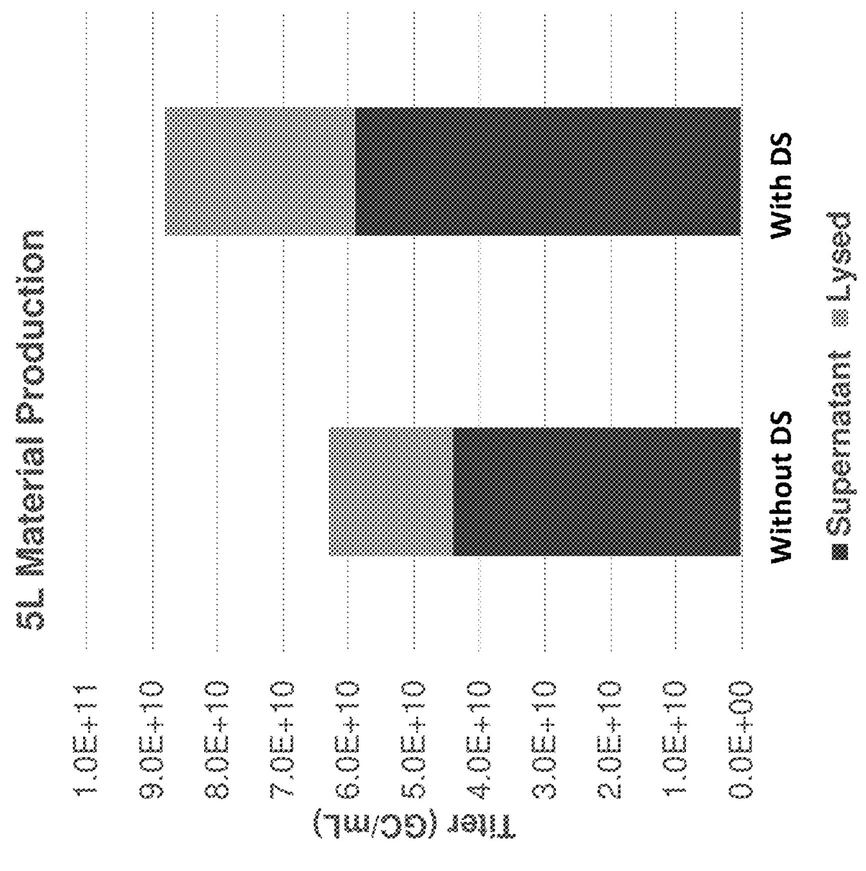
FIG. 7. AAV8 production in bench scale 5 L reactor using dextran sulfate during transfection at a concentration of 2 mg/L.

Example 3—Effect of Dextran Sulfate on AAV Titer in Bench Scale 5 L Reactors The effect of dextran sulfate on transfection based AAV production in bench scale reactors was studied. Recombinant AAV8 comprising transgene 2 was produced via transient transfection of HEK293 cells. Briefly, HEK293 cells were expanded for three days in 5 L reactors in medium comprising dextran sulfate at 4 mg/l. Prior to transfection, the culture was diluted 1:1 with fresh medium to provide a dextran sulfate concentration of 2 mg/L. The cells were transfected with a mixture of polyethylenimine (PEI) and 3 plasmids encoding adeno-virus helper functions, transgene and AAV Cap/Rep. Transfected cultures were maintained for four days following transfection to allow AAV production. AAV particles were recovered either from the culture supernatant, or from the culture following lysis of the cells. AAV supernatant or lysis titer was increased an average of 35 to 40%, respectively with the inclusion of dextran sulfate. FIG. 7.

Example 4—Effect of Dextran Sulfate on AAV Titer in Different Culture Media

Figure 8:
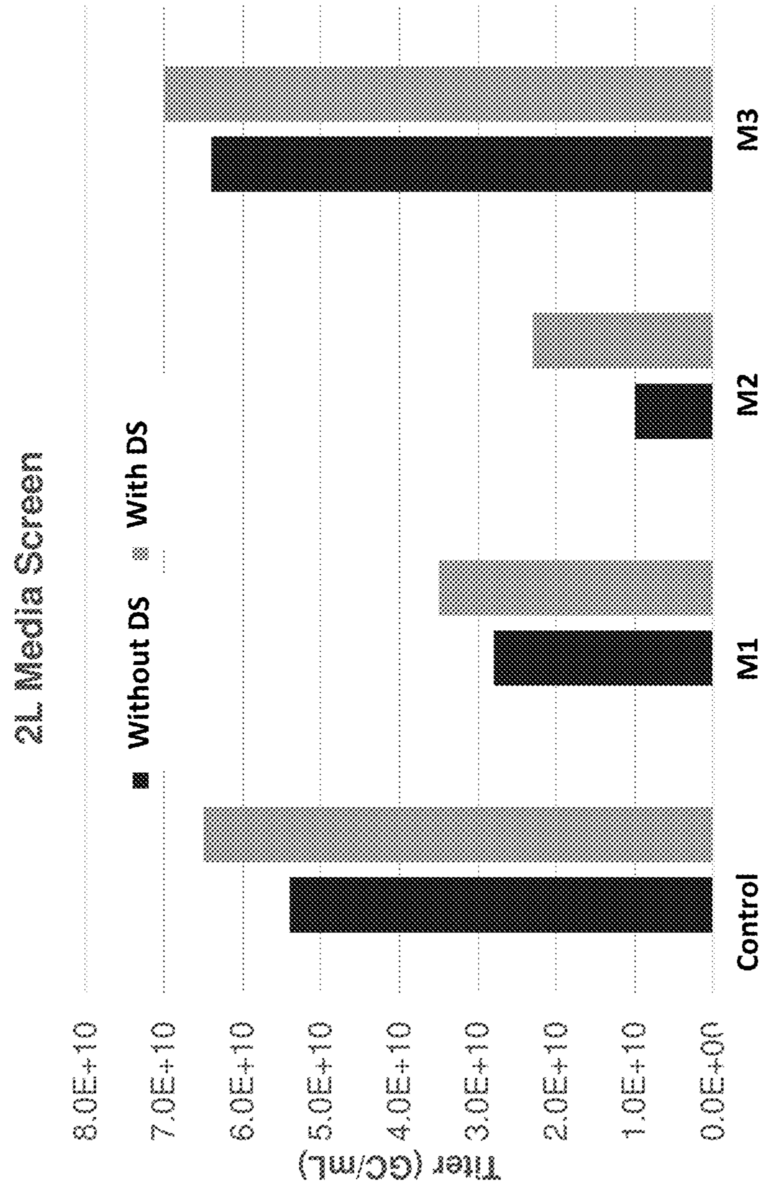
FIG. 8. AAV8 production in 2 L bench scale reactors using different commercial media. Dextran sulfate was present at 2 mg/L during transfection.

The effect of dextran sulfate on transfection based AAV production in different commercially available culture media (M1, M2, and M3 in FIG. 8) was studied. Recombinant AAV8 comprising transgene 2 was produced via transient transfection of HEK293 cells. Briefly, HEK293 cells were expanded for 3 days in 2 L reactors in different culture media comprising dextran sulfate at 4 mg/L. Prior to transfection, the cultures were diluted 1:1 with fresh medium to provide a dextran sulfate concentration of 2 mg/L. The cells were transfected with a mixture of polyethylenimine (PEI) and 3 plasmids encoding adeno-virus helper functions, transgene and AAV Cap/Rep. Transfected cultures were maintained for 4 days following transfection to allow AAV production. AAV particles were recovered either from the culture supernatant, or from the culture following lysis of the cells. FIG. 8. For the M1, M2 and M3 media, inclusion of dextran sulfate in the culture increased titer recovered from the lysis of cells by 25%, 130%, and 10%, respectively.

Figure 9:
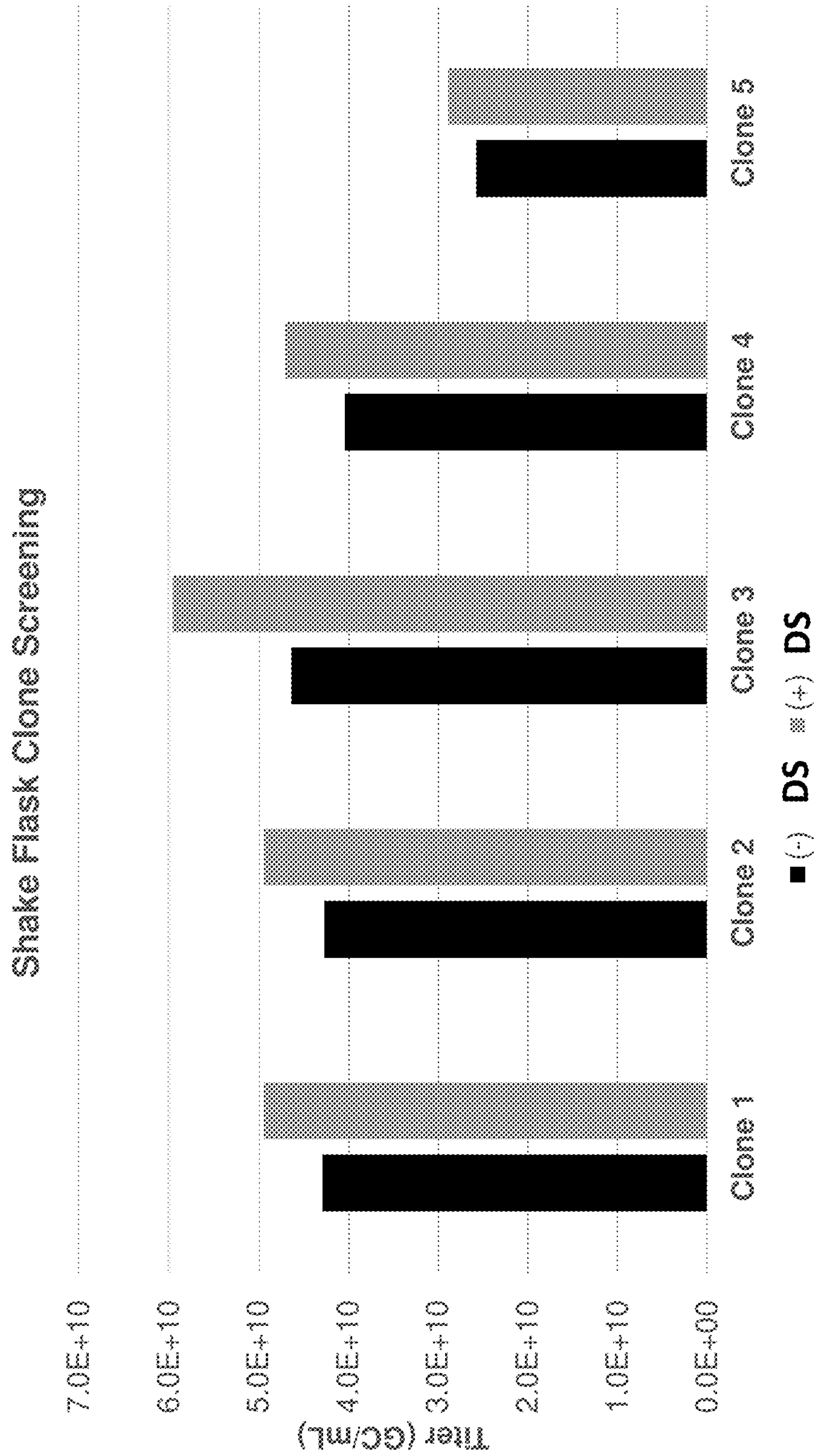
FIG. 9. AAV8 production in shake flasks using different host cell clones. Dextran sulfate was present at 2 mg/L during transfection.

Example 5—Effect of Dextran Sulfate on AAV Titer Using Different Host Cell Clones The effect of dextran sulfate on transfection based AAV production using different HEK293 host cell clones was studied. Recombinant AAV8 comprising transgene 2 was produced via transient transfection of different HEK293 cell clones. Briefly, HEK293 cell clones were expanded for 3 days in shake flasks in culture media comprising dextran sulfate at 4 mg/L. Prior to transfection, the cultures were diluted 1:1 with fresh medium to provide a dextran sulfate concentration of 2 mg/L. The cells were transfected with a mixture of polyethylenimine (PEI) and 3 plasmids encoding adeno-virus helper functions, transgene and AAV Cap/Rep. Transfected cultures were maintained for 4 days following transfection to allow AAV production. AAV particles were recovered from the culture supernatant. FIG. 9. AAV8 titer was increased with the inclusion of dextran sulfate in all five HEK cell clones studied. AAV8 titer was increased by an average of 18% with the inclusion of dextran sulfate across the five different HEK cell clones.

Figure 10:
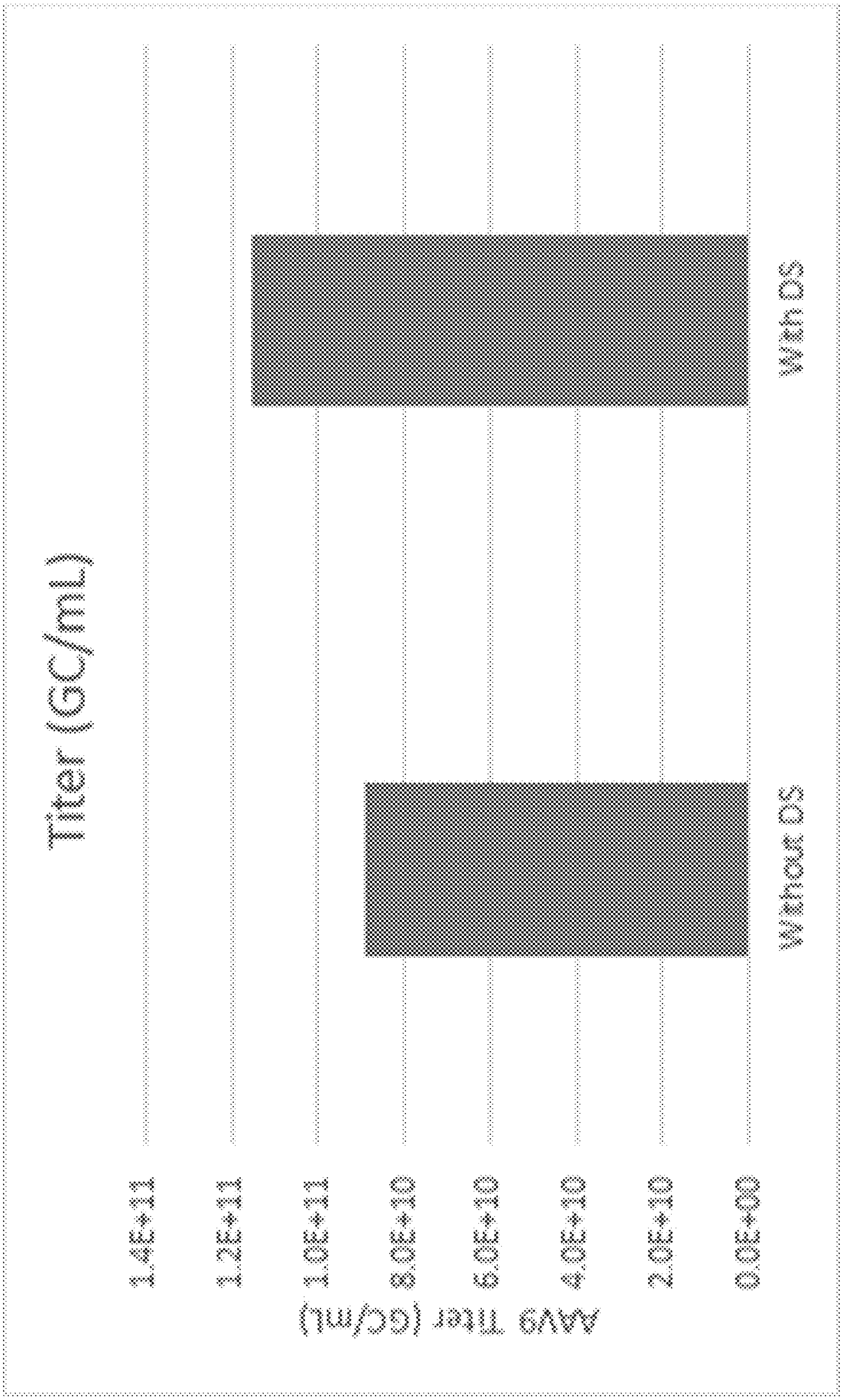
FIG. 10. AAV9 production in bench scale 5 L reactor using dextran sulfate during transfection FIG. 11. Inclusion of dextran sulfate in high-density seed train prior to transfection increases AAV titer.

Example 6—Effect of Dextran Sulfate on AAV9 Titer in Bench Scale 5 L Reactors The effect of dextran sulfate on transfection based AAV9 production in bench scale reactors was studied. Recombinant AAV9 comprising transgene 3 was produced via transient transfection of HEK293 cells. Briefly, HEK293 cells were expanded for three days in 5 L reactors in medium comprising dextran sulfate at 4 mg/L concentration. Prior to transfection, the cultures were diluted 1:1 with fresh medium to provide a dextran sulfate concentration of 2 mg/L. The cells were transfected with a mixture of polyethylenimine (PEI) and 3 plasmids encoding adeno-virus helper functions, transgene and AAV Cap/Rep. Transfected cultures were maintained for five days following transfection to allow AAV production. FIG. 10. AAV9 supernatant titer was increased by an average of 30% with the inclusion of dextran sulfate.

Example 7—Effect of Dextran Sulfate on AAV Titer when Used Both During Seed Cell Train Prior to Transfection and Production Culture (Transgene 3)

Figure 11:
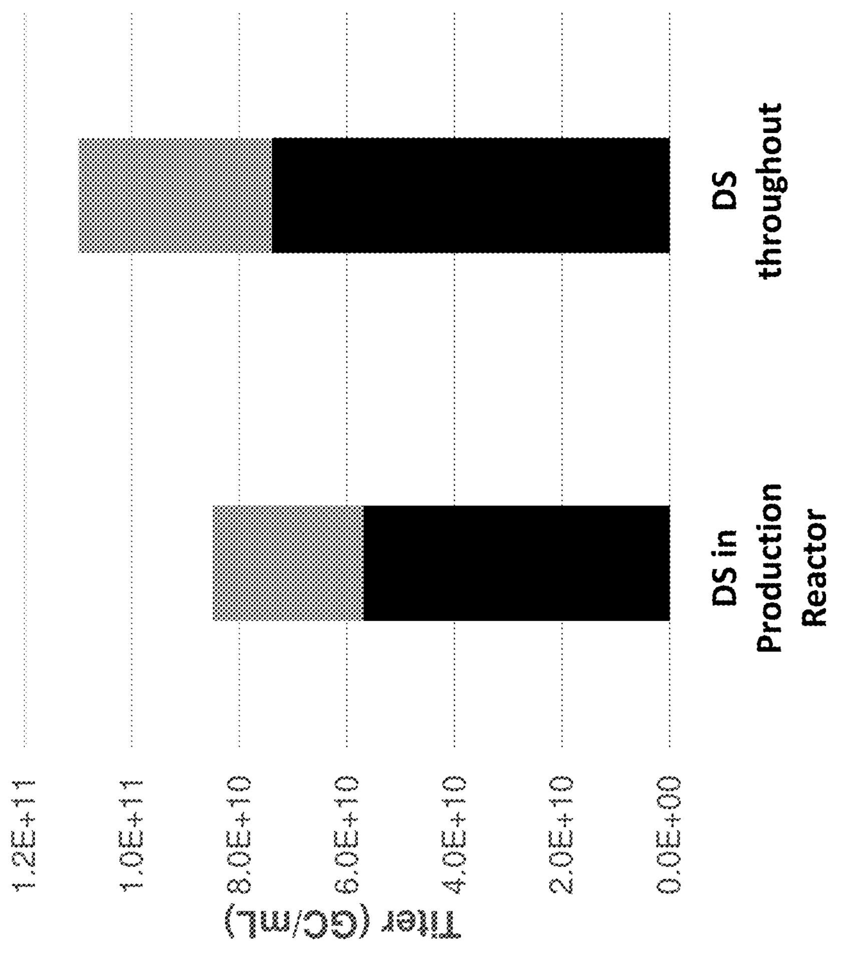

Recombinant AAV9 comprising transgene 3 was produced via transient transfection of HEK293 cells in a 200 L production culture. HEK cells were expanded using a seed train comprising a high-density perfusion culture step in the presence of 4 mg/L dextran sulfate. A 200 L production cultures was inoculated with the HEK seed cells and, prior to transfection, dextran sulfate concentration was adjusted to 2 mg/L in the production culture. The cells were transfected with a mixture of polyethylenimine (PEI) and 3 plasmids encoding adeno-virus helper functions, transgene and AAV Cap/Rep. Transfected cultures were maintained for five days following transfection to allow AAV production. AAV particles were recovered either from the culture supernatant (black bar in FIG. 11), or from the culture following lysis of the cells (grey bar in FIG. 11). A control production culture was inoculated with HEK seed cells expanded in the absence of dextran sulfate. FIG. 11. AAV9 titer was increased by 30% when dextran sulfate was used during both seed cell expansion and the transfection of production culture.

Example 8—Effect of Dextran Sulfate on AAV Titer when Used Both During Seed Train Prior to Transfection and Production Culture (Transgene 1)

Figure 12:
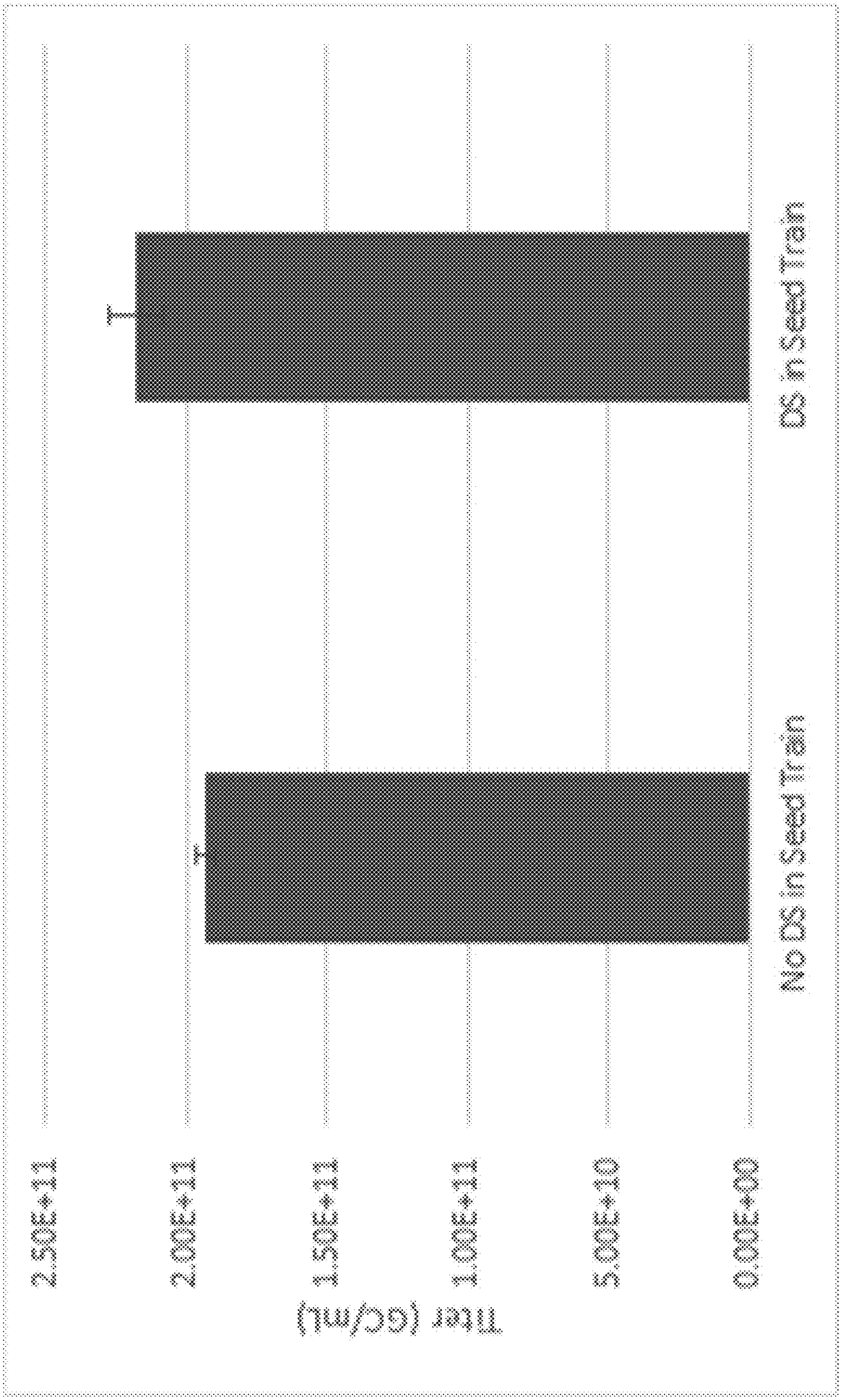
FIG. 12. Inclusion of dextran sulfate in seed train prior to transfection increases AAV titer.

The effect of dextran sulfate in the seed train for transfection based AAV production in bench scale reactors was studied. Recombinant AAV8 comprising transgene 1 was produced via transient transfection of HEK293 cells. Briefly, HEK293 cells were expanded for five passages (18 days) in medium with or without dextran sulfate. Cells were then expanded for three days in triplicate 2 L reactors in medium (seed train) with 4 mg/L or without (0) dextran sulfate. Prior to transfection, the culture was diluted 1:1 with fresh medium to provide cultures with dextran sulfate concentration of 2 mg/L or 0, respectively. The cells were transfected with a mixture of polyethylenimine (PEI) and 3 plasmids encoding adeno-virus helper functions, transgene and AAV Cap/Rep. Transfected cultures were maintained for four days following transfection to allow AAV production. AAV particles were recovered from the culture following lysis of the cells. AAV lysis titer was increased an average of 10 to 15%, with the inclusion of dextran sulfate in the seed train and production cultures (statistical significance $p<0.05$). FIG. 12.

While the disclosed methods have been described in connection with what is presently considered to be the most practical and preferred embodiments, it is to be understood that the methods encompassed by the disclosure are not to be limited to the disclosed embodiments, but on the contrary, is intended to cover various modifications and equivalent arrangements included within the spirit and scope of the appended claims.

All publications, patents, patent applications, internet sites, and accession numbers/database sequences including both polynucleotide and polypeptide sequences cited herein are hereby incorporated by reference herein in their entirety for all purposes to the same extent as if each individual publication, patent, patent application, internet site, or accession number/database sequence were specifically and individually indicated to be so incorporated by reference.

What is claimed is:

1. A method of transfecting mammalian cells, comprising:

a) providing a suspension cell culture comprising the cells, wherein the culture comprises between about 1 mg/L and about 3 mg/L dextran sulfate; and b) transfecting the cells by adding to the culture of (a) a composition comprising one or more polynucleotides and a transfection reagent, wherein the transfection reagent comprises a polymer.

2. A method of producing a recombinant polypeptide, comprising:

a) providing a suspension cell culture comprising mammalian cells suitable for producing the recombinant polypeptide, wherein the culture comprises between about 1 mg/L and about 3 mg/L dextran sulfate;

b) transfecting the cells by adding to the culture of a) a composition comprising one or more polynucleotides encoding the polypeptide and a transfection reagent; and c) maintaining the cell culture comprising the transfected cells under conditions that allow the production of the recombinant polypeptide, wherein the transfection reagent comprises a polymer.

3. The method of claim 2, wherein the polypeptide is an antibody or antigen-binding fragment thereof, bispecific antibody, enzyme, fusion protein or Fc fusion protein.

4. A method of producing a recombinant virus particle, comprising:

a) providing a suspension cell culture comprising mammalian cells suitable for producing the recombinant virus particle, wherein the culture comprises between about 1 mg/L and about 3 mg/L dextran sulfate;

b) transfecting the cells by adding to the culture of a) a composition comprising one or more polynucleotides containing genes necessary for producing the recombinant virus particle and a transfection reagent; and c) maintaining the cell culture comprising the transfected cells under conditions that allow the production of the recombinant virus particle, wherein the transfection reagent comprises a polymer.

5. The method of claim 4, wherein the culture of a) comprises about 2 mg/L dextran sulfate.

6. The method of claim 4, wherein the cell culture comprises suspension adapted cells.

7. The method of claim 4, wherein the cells comprise HEK293 cells, HEK derived cells, CHO cells, CHO derived cells, HeLa cells, SF-9 cells, BHK cells, and/or Vero cells, or combinations thereof.

8. The method of claim 4, wherein the cells comprise HEK293 cells.

9. The method of claim 4, wherein the cells comprise CHO cells or CHO-K1 cells.

10. The method of claim 4, wherein the transfection reagent comprises a polymer, wherein the polymer comprises poly (L-Lysine) (PLL), polyethylenimine (PEI), a polysaccharide, Poly[2-(dimethylamino)ethyl methacrylate] (PDMAEMA), a dendrimer, or a combination thereof.

11. The method of claim 4, wherein the transfection reagent comprises polyethylenimine (PEI).

12. The method of claim 4, wherein the cell culture has a volume of between about 50 liters and about 20,000 liters.

13. The method of claim 12, wherein the cell culture has a volume between about 50 liters and about 5,000 liters.

14. The method of claim 4, wherein the recombinant virus particle is an rAAV particle.

15. The method of claim 14, wherein the rAAV particle comprises a capsid protein of a AAV1, AAV2, AAV3, AAV4, AAV5, AAV6, AAV7, AAV8, AAV9, AAV10, AAV11, AAV12, AAV13, AAV14, AAV15, AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 serotype.

16. The method of claim 14, further comprising recovering the rAAV particles.

17. The method of claim 14, wherein the cell culture produces at least about 1.1 times as many rAAV particles measured as GC/ml than a reference method in which the suspension cell culture comprising the cells does not comprise dextran sulfate.

18. The method of claim 14, wherein the one or more polynucleotide encode a) an rAAV genome to be packaged, b) adenovirus helper functions necessary for packaging, c) an AAV rep protein sufficient for packaging, and d) an AAV cap proteins sufficient for packaging.

19. The method of claim 18, wherein the one or more polynucleotide comprises a polynucleotide encoding the rAAV genome, a polynucleotide encoding the AAV rep protein and the AAV cap proteins, and a polynucleotide encoding the adenovirus helper functions.

20. The method of claim 19, wherein the adenovirus helper functions comprise at least one of an adenovirus E1a gene, E1b gene, E4 gene, E2a gene, and VA gene.

* * * * *